US008968756B2

(12) United States Patent
Fang et al.

(10) Patent No.: US 8,968,756 B2
(45) Date of Patent: Mar. 3, 2015

(54) FABRICATION OF BISCROLLED FIBER USING CARBON NANOTUBE SHEET

(75) Inventors: Shaoli Fang, Richardson, TX (US); Marcio Dias Lima, Richardson, TX (US); Xavier N. Lepro-Chavez, Richardson, TX (US); Javier Carretero-Gonzalez, Dallas, TX (US); Elizabeth Castillo-Martinez, Dallas, TX (US); Raquel Ovalle-Robles, Sachse, TX (US); Carter Sebastian Haines, Murphy, TX (US); David Michael Novitski, Richardson, TX (US); Mohammad H. Haque, Dallas, TX (US); Chihye Lewis-Azad, Dallas, TX (US); Mikhail Kozlov, Dallas, TX (US); Anvar A. Zakhidov, McKinney, TX (US); Ray H. Baughman, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 129 days.

(21) Appl. No.: 13/322,880

(22) PCT Filed: May 27, 2010

(86) PCT No.: PCT/US2010/036378
§ 371 (c)(1),
(2), (4) Date: Nov. 28, 2011

(87) PCT Pub. No.: WO2011/005375
PCT Pub. Date: Jan. 13, 2011

(65) Prior Publication Data
US 2012/0100203 A1    Apr. 26, 2012

Related U.S. Application Data

(60) Provisional application No. 61/181,601, filed on May 27, 2009.

(51) Int. Cl.
*A01N 25/34* (2006.01)
*H01M 4/133* (2010.01)
(Continued)

(52) U.S. Cl.
CPC .................. *H01M 4/133* (2013.01); *D01F 9/12* (2013.01); *H01M 4/131* (2013.01);
(Continued)

(58) Field of Classification Search
CPC ......................................................... D01F 9/12
USPC ....................................................... 424/402
See application file for complete search history.

(56) References Cited

U.S. PATENT DOCUMENTS 6,782,892 B2    8/2004  Li et al.
2008/0170982 A1    7/2008  Zhang et al.

FOREIGN PATENT DOCUMENTS

WO    WO 2007015710 A2 *    2/2007
WO    WO2007015710 A3 *    2/2007

OTHER PUBLICATIONS

M. Zhang et al., "Strong, Transparent, Multifunctional, Carbon Nanotube Sheets," Science, vol. 309; p. 1215-11219; (2005).
(Continued)

*Primary Examiner* — Benjamin Packard
(74) *Attorney, Agent, or Firm* — Greenberg Traurig, LLP; Ross Spencer Garsson

(57) ABSTRACT

Fabrication of yarns or other shaped articles from materials in powder form (or nanoparticles or nanofibers) using carbon nanotube/nanofiber sheet as a platform (template). This includes methods for fabricating biscrolled yarns using carbon nanotube/nanofiber sheets and biscrolled fibers fabricated thereby.

20 Claims, 29 Drawing Sheets

(51) Int. Cl.
*D01F 9/12* (2006.01)
*H01M 4/131* (2010.01)
*H01M 4/1391* (2010.01)
*H01M 4/1393* (2010.01)
*H01M 4/58* (2010.01)
*H01M 4/587* (2010.01)
*H01M 4/96* (2006.01)
*D02G 3/16* (2006.01)
*A61L 15/18* (2006.01)
*A61L 17/04* (2006.01)
*H01M 8/00* (2006.01)
*H01M 10/0525* (2010.01)

(52) U.S. Cl.
CPC ......... *H01M 4/1391* (2013.01); *H01M 4/1393* (2013.01); *H01M 4/5825* (2013.01); *H01M 4/587* (2013.01); *H01M 4/96* (2013.01); *H01M 8/00* (2013.01); *H01M 10/0525* (2013.01); *Y02E 60/122* (2013.01); *Y02E 60/50* (2013.01); *D02G 3/16* (2013.01); *D10B 2101/122* (2013.01); *A61L 15/18* (2013.01); *A61L 17/04* (2013.01); *A61L 2300/108* (2013.01); *A61L 2300/418* (2013.01); *A61L 2400/12* (2013.01)
USPC ......................................................... 424/402

(56) References Cited

OTHER PUBLICATIONS

X. Zhang et al., "Ultrastrong, Stiff, and Lightweight Carbon-Nanotube Fibers," Advanced Materials 19; pp. 4189-4201; (2007).
Y. Li et al.; "Direct Spinning of Carbon Nanotube Fibers from Chemical Vapor Deposition Synthesis," Science, vol. 304; pp. 276-278; (2004).
Y. Wu et al.; "Superconducting MgB2 Nanowires," Advanced Materials, 13, No. 19; pp. 1487-1489; (2001).
D. Whang et al.; "Large-Scale Hierarchical Organization of Nanowire Arrays for Integrated Nanosystems," Nano Letters, vol. 3, No. 9; pp. 1256-1259; (2003).
N. Li et al.; "Bismuth Nanotubes: A Rational Low-Temperature Synthetic Route," J. Am. Chem. Soc. 123; pp. 9904-9905; (2001).
L. M. Viculis et al.; "A Chemical Route to Carbon Nanoscrolls," Science, vol. 299; p. 1361; Feb. 28, 2003.
Z.L. Wang; "Nanobelts, Nanowires, and Nanodiskettes of Semiconducting Oxides—From Materials to Nanodevices," Advanced Materials 15; pp. 432-436 (2003).
X.D. Wang et al.; "Rectangular Porous ZnO—ZnS Nanocables and ZnS Nanotubes," Advanced Materials 14, No. 23; pp. 1732-1735 (2002).
W. L. Hughes et al.; "Nanobelts as nanocantilevers," Applied Physics Letters, vol. 82, No. 17; pp. 2886-2888; Apr. 28, 2003.
J.W. Liu et al. "Synthesis of Carbon Nanotubes and Nanobelts through a Medial-Reduction Method," Journal of Physical Chemistry B 107, pp. 6329-6332 (2003).
Y.B. Li et al.; "Mg2Zn11—MgO belt-like nanocables," Chemical Physics Letters 375; pp. 102-105 (2003).
D.V. Kosynkin et al.; "Longitudinal unzipping of carbon nanotubes to form graphene nanoribbons," Nature, vol. 458; pp. 872-876; Apr. 16, 2009.
W. Takahima et al.; "Amperometric phenol biosensor based on covalent immobilization of tyrosinase onto an electrochemically prepared novel copolymer poly (n-3-aminopropyl pyrrole-co-pyrrole) film," Sensors and Actuators B 99; pp. 271-277; (2004).

C. H. Yen et al.; "Deposition of Platinum Nanoparticles on Carbon Nanotubes by Supercritical Fluid Method," Journal of Nanoscience and Nanotechnology; vol. 5; pp. 1852-1857; (2005).
C.A. Lawrence, Fundamentals of Spun Yarn Technology, CRC Press, 2002.
J. Nagamatsu et al.; "Superconductivity at 39 K in magnesium diboride," Nature, vol. 410; p. 63; Mar. 1, 2001.
E. Yoo et al., "Large reversible Li storage of grapheme nanosheet families for use in rechargeable lithium ion batteries", Nanoletters, vol. 8, No. 8; pp. 2277-2282; (2008).
S. M. Paek et al., "Enhanced Cyclic performance and Lithium storage capacity of SnO2/grapheme nanoporous electrodes with three-dimensionally delaminated flexible structure", Nano Letters, vol. 9, No. 1; pp. 72-75; (2009).
D. V. Kosynkin et al.; "Longitudinal unzipping of carbon nanotubes to form graphene nanoribbons," Nature, vol. 458, 872-876; Apr. 16, 2009.
L. Jiao et al.; "Narrow graphene nanoribbons from carbon nanotubes," Nature, vol. 458; pp. 877-880; Apr. 16, 2009.
L. Jiao et al.; "Facile synthesis of high-quality graphene nanoribbons," Nature Nanotechnology, vol. 5; pp. 321-325; (2010).
J. Chmiola et al.; "Anomalous Increase in Carbon Capacitance at Pore Sizes Less Than 1 Nanometer," Science, vol. 313; pp. 1760-1763; Sep. 22, 2006.
Y. Gogotsi et al.; "Nanoporous carbide-derived carbon with tunable pore size," Nature Materials, vol. 2; pp. 591-594; (2003).
A. B. Dalton et al.; "Super-tough carbon-nanotube fibres," Nature, vol. 423; p. 703 (2003).
S. Kundu et al.; "Electrocatalytic Activity and Stability of Nitrogen-Containing Carbon Nanotubes in the Oxygen Reduction Reaction," J. Phys. Chem. C 113; pp. 14302-14310; (2009).
Matheson et al.; "Influence of Nitrogen Doping on Oxygen Reduction Electrocatalysis at Carbon Nanofiber Electrodes," J. Phys. Chem. B 109; pp. 4707-4716; (2005).
Y. Shao et al.; "Nitrogen-doped carbon nanostructures and their composites as catalytic materials for proton exchange membrane fuel cell," Applied Catalysis B: Environmental, 79; pp. 89-99; (2008).
R. Krupke et al.; "Thin Films of Metallic Carbon Nanotubes Prepared by Dielectrophoresis," Advanced Materials, 18; pp. 1468-1470; (2006).
A. K. Pal et al.; "Electrodeposited carbon nanotube thin films," Thin Solid Films 476; pp. 288-294; (2005).
P. Poulin et al.; "Films and fibers of oriented single wall nanotubes," Carbon 40; pp. 1741-1749; (2002).
A.R. Boccaccini et al.; "Electrophoretic deposition of carbon nanotubes," Carbon 44; pp. 3149-3160; (2006).
D.V. Kosinkyn et al.; "Longitudinal unzipping of carbon nanotubes to form graphene nanoribbons," Nature, vol. 458; pp. 872-877; (2009).
M. Terrones et al.; "Novel nanoscale gas containers: encapsulation of N2 in CNx nanotubes," Chem. Commun. 23; pp. 2335-2336; (2000).
S. Kundu et al.; "Electrocatalytic Activity and Stability of Nitrogen-Containing Carbon Nanotubes in the Oxygen Reduction Reaction," J. Phys. Chem C, 113; pp. 14302-14310; (2009).
V.E. Ebron et al.; "Fuel-Powered Artificial Muscles," Science, vol. 311; pp. 1580-1583; (2006).
M. Monthioux; "Filing single-wall carbon nanotubes," Carbon, 40; pp. 1809-1823; (2002).
Jeremy Sloan et al.; "Crystallisation inside fullerene related structures," J. Mater. Chem.; pp. 1089-1095; (1997).
United States International Searching Authority; International Search Report & Written Opinion for PCT/U2010/036378; Dec. 20, 2010; Alexandria, VA.

* cited by examiner 2701  2702

FABRICATION OF BISCROLLED FIBER USING CARBON NANOTUBE SHEET

CROSS-REFERENCE TO RELATED PATENT APPLICATION

This Application for Patent is the 35 U.S.C. §371 U.S. National Application of International Application No. PCT/US2010/036378, filed May 27, 2010, which claims the benefit of priority from U.S. Provisional Patent Application Ser. No. 61/181,601, filed May 27, 2009, entitled "Fabrication of Biscrolled Fiber Using Carbon Nanotube Sheet," which provisional patent application is commonly assigned to the assignee of the present invention, and which disclosure is considered part of and is incorporated by reference in its entirety in the disclosure of this application.

GOVERNMENT INTEREST

This work was supported by Air Force Office of Scientific Research grant FA9550-09-1-0384, Office of Naval Research MURI grant N00014-08-1-0654, Air Force Grant AOARD-10-4067, NSF grant DMI-0609115, and Robert A. Welch Foundation grant AT-0029. The U.S. government may have certain rights in the invention.

FIELD OF INVENTION

The present invention is related to fabrication of fibers (yarns) or other shaped articles from materials in powder form (or nanoparticles or nanofibers) using carbon nanotube/nanofiber sheet as a platform (template). Embodiments of the present invention relate to methods for fabricating biscrolled fibers using carbon nanotube/nanofiber sheets and biscrolled fibers fabricated thereby.

BACKGROUND OF INVENTION

Multifunctional yarns are required for diverse applications, like clothing that protects emergency responders and provides sensing, communication, energy harvesting, and storage capabilities. Fabrics from such yarns could provide electrodes for high performance batteries, supercapacitors, and fuel cells that might be imbedded in vehicle shells. Despite important advances, critical problems remain: (1) most multifunctional materials are unspinnable using known technologies, (2) nanopowder and nanofiber functionality often degrades when accessible surface area decreases during processing, and (3) coating nanoparticles or nanofibers on yarns after yarn spinning can severely decrease loading levels and durability.

A generically applicable method is needed for configuring functional nanoparticles, nanofibers, and nanoribbons as the major component of weavable yarns that can perform, for example, as superconductors; battery electrodes; ferromagnets; catalytic convertors; carriers of biological and biopharmaceutical materials; photocatalysts and photosensitizers for photovoltaic cells and photoelectrolysis cells for hydrogen production; hydrogen storage containers; and active oxygen generators for self-cleaning and destruction of biological threats.

A problem hindering the applications of these powder materials is the need for methods for converting these powder (or nanoparticles or nanofibers) into yarns with ultra-high loading of the powder component to effectively utilize the properties of the powder materials. Solid-state-spun carbon nanotube (CNT) sheet as described in U.S. Patent Appl. Publ. No. 2008/0170982, published Jul. 17, 2008 ("the '982 Application"), is a novel aerogel material that can support load many times of its own mass and be easily converted into yarns or other shaped articles.

Present invention embodiments provide a novel approach that convert up to 99 weight percent of one or more other functional materials into yarns using twist-based spinning of carbon nanotube sheets. CNT sheets of multiwalled nanotubes (MWNTs), few walled nanotubes (FWNTs), or single walled nanotubes (SWNTs) are used as a platform (providing the mechanical support) for collecting and confining the particle materials, forming a bilayered sheet structure. Then the bilayered sheet ribbon is scrolled into a biscrolled yarn, which is designated the guest@host. The biscrolling method is capable of incorporating large amount of other materials onto CNT sheet, achieving ultra-high loading of the particle materials and maintaining the grain size of the material. As a result, the properties of the biscrolled yarns predominantly come from the deposited guest component other than from CNT sheet. For example, biscrolled yarns have been demonstrated as superconductors; battery electrodes; supercapacitors; carriers of biological and biopharmaceutical materials; photocatalysts for self-cleaning textiles, etc.

SUMMARY OF INVENTION

The present invention includes fabrication of biscrolled fiber using carbon nanotube sheet.

In general, in one aspect, the invention features a method that includes forming a nanofiber sheet or nanofiber sheet stack as a sheet platform for particle material deposition. The method further includes depositing particle material onto the sheet platform to form a bilayered sheet structure. The method further includes scrolling the bilayered sheet structure into a biscrolled yarn.

A "nanofiber sheet" is a sheet having any shape (especially including rectangular shape, wedge shape or distorted wedge shape) that includes nanofibers.

This term "sheet" can be used in the same sense as the term "web."

"Particle material" includes particles that have any shape, like fiber shape, plate shape, and round or oblong shape.

The term "bilayered" means that layers comprising nanofiber sheet and particle material can be separately observed, though some interpenetration of these layers typically occurs. Included in the term "bilayered" are layers that comprise more than two layers that have distinguishably different average compositions. (Such more than two layers can be provided, for instance, by depositing different host materials on opposite sides of a sheet platform.)

The term "scrolled" means that bilayers are wrapped in scroll fashion (especially helical scroll fashion) no matter the degree of structural perfection achieved by such scrolling.

The meaning of these terms (including "nanofiber sheet," "particle material," "bilayered," and "scrolled") are further reflected herein, including in the context in which these terms are utilized.

Implementations of the invention can include one or more of the following features:

The method can further include densifying the biscrolled yarn using liquid absorption and subsequent evaporation.

The method can further include introducing a twist during formation of the biscrolled yarn.

The sheet platform can further include carbon nanotubes.

The sheet platform can further predominately consist of carbon nanotubes on a weight basis. The biscrolled yarn can have a specific strength of at least about 50 M Pa/(g/cm$^3$).

The carbon nanotubes in the sheet platform can be predominately oriented in the same in-plane direction.

The carbon nanotube sheet platform can be (a) a carbon nanotube sheet wedge that results from direct twist-based spinning from a carbon nanotube forest or (b) a self-suspended nanotube sheet or sheet stack obtained by sheet draw from a carbon nanotube forest.

The sheet platform can include different sheets in a sheet stack. The different sheets can include the carbon nanotubes, which are in-plane aligned. The direction of the in-plane alignment of the carbon nanotubes in these different sheets can differ.

The sheet platform can be free-standing.

The sheet platform can be supported on a substrate that can be removed after the depositing of the particle material.

The particle material can include at least about 50 weight percent of the biscrolled yarn. The particle materials can include at least about 80 weight percent of the biscrolled yarn. The particle material can include at least about 90 weight percent of the biscrolled yarn.

The method can further include removing the carbon nanotube sheet. The step of removing the carbon nanotube sheet can occur after the particle material is made coherent.

The particle material can include nanoparticles. The nanoparticles can be in powder form. The nanoparticles can include nanofibers. The nanofibers can include nitrogen doped nanotubes or graphene ribbons.

The particle material comprises a superconductor or components that can be converted to a superconductor by processing the biscrolled yarn.

The particle material can include a catalyst.

The particle material can include a biologically active material.

The particle material can include $TiO_2$.

The method of Claim 3, further including that the step of making the particle material can be coherent. The step of making the particle material coherent can be sintering, melting, or combinations thereof.

The step of depositing particle material can include the use of an ink jet printing process.

The method can further include using particle material that can be liquid dispersed, and depositing the particle material from a liquid dispersed state. The depositing the particle material from a liquid dispersed state can include a filtration method.

The step of depositing the particle material can include a liquid-free deposition method. The liquid-free deposition method can be: electrostatic deposition, electron beam evaporation, sputtering, chemical vapor deposition (CVD), dry powder airbrush deposition, deposition of gas-dispersed guest nanoparticles immediately after their formation by reaction of gases, or a combination thereof.

The step of depositing the particle material can include a liquid state or quasi-liquid state deposition method. The liquid state or quasi-liquid state deposition method can be electrophoretic deposition, filtration deposition using the nanotube sheet stack as a filter to capture guest nanoparticles, solution drop casting, ink-jet printing, or a combination thereof.

The step of depositing particle material can include deposition of nanoparticles from a supercritical fluid.

The step of depositing particle material can include profiling distribution of the particle material. The step of profiling the distribution of the particle material can include preferentially positioning the particle material on one side of the sheet platform. The step of preferentially positioning the particle material can result in preferential distribution of the particle material in either the core or shell of the biscrolled yarn. The step of profiling the distribution of the particle material can include preferentially locating the particle material to increase accessibility of light to the particle material. The step of preferentially locating the particle material can allow the biscrolled yarn to be operable for a function of a dye-based electrochemical solar cell, light enabled textile cleaning, destruction of a biological threat, destruction of a chemical threat, or a combination thereof. The particle material can include $TiO_2$.

The step of depositing particle material can include depositing a first type of particle material and a second type of particle material onto the carbon nanotube sheet platform. The first type of particle material can be deposited on a first side of the carbon nanotube sheet platform. The second type of particle material can be deposited on a second side of the carbon nanotube sheet platform.

The step of depositing particle material can include depositing the particle material on two sides of the carbon nanotube sheet platform. The same type of particle material can be deposited on the two sides of a carbon nanotube sheet platform.

The step of depositing the particle material can be performed by a process that patterns the particle material on the carbon nanotube sheet platform. The process that patterns the particle material can be an ink jet printing process.

The particle material can include high surface carbon materials obtained by reaction of carbides. The biscrolled yarn can be operable as a supercapacitor yarn.

In general, in another aspect, the invention features a biscrolled yarn produced by the above method.

In general, in another aspect, the invention features a method that includes selecting a biscrolled yarn. The method further includes using the biscrolled yarn as or in a superconducting yarn, a superconducting yarn application, an energy storage application, an electrode, an electrode application; a catalyst, a catalyst application; a multi-functional textile, a multi-functional textile application, a biomedical application, a shape memory alloy actuator, a shape memory alloy actuator application, a dye-based electrochemical solar cell, light enabled textile cleaning, destruction of a biological threat, destruction of a chemical threat, or a combination thereof.

Implementations of the invention can include one or more of the following features:

The biscrolled yarn can be used as a superconducting yarn. The superconducting yarn can be used for a superconductor application. The biscrolled yarn can include boron and magnesium.

The biscrolled yarn can be used for energy storage applications.

The biscrolled yarn can be used as the electrode material in a supercapacitor.

The biscrolled yarn can be used as the electrode material in a battery.

The biscrolled yarn can be used as a high performance electrode.

The biscrolled yarn can be used for a high performance electrode application.

The biscrolled yarn can be used as a catalyst.

The biscrolled yarn can be used for a catalyst application.

The biscrolled yarn can be used as a multi-functional textile.

The biscrolled yarn can be used for a multi-functional textile application.

The biscrolled yarn can be used for a biomedical application. The biomedical application can be an implantable biometric sensor, a suture, an external biometric sensor, a hemostatic compressive dressing, a hemostatic non-absorbable suture, a drug delivery agent, a 3-dimensional tissue engineering in vitro, a 3-dimensional tissue engineering in vivo, or a combinations thereof.

The biscrolled yarn can be used as a shape memory alloy actuator.

The biscrolled yarn can be used for a shape memory alloy actuator application.

The biscrolled yarn can be used for a dye-based electrochemical solar cell.

The biscrolled yarn can be used for a light enabled textile cleaning.

The biscrolled yarn can be used for destruction of a biological threat.

The biscrolled yarn can be used for destruction of a chemical threat.

In general, in another aspect, the invention features an apparatus operable for using the biscrolled yarn in one of the applications identified in the above method.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
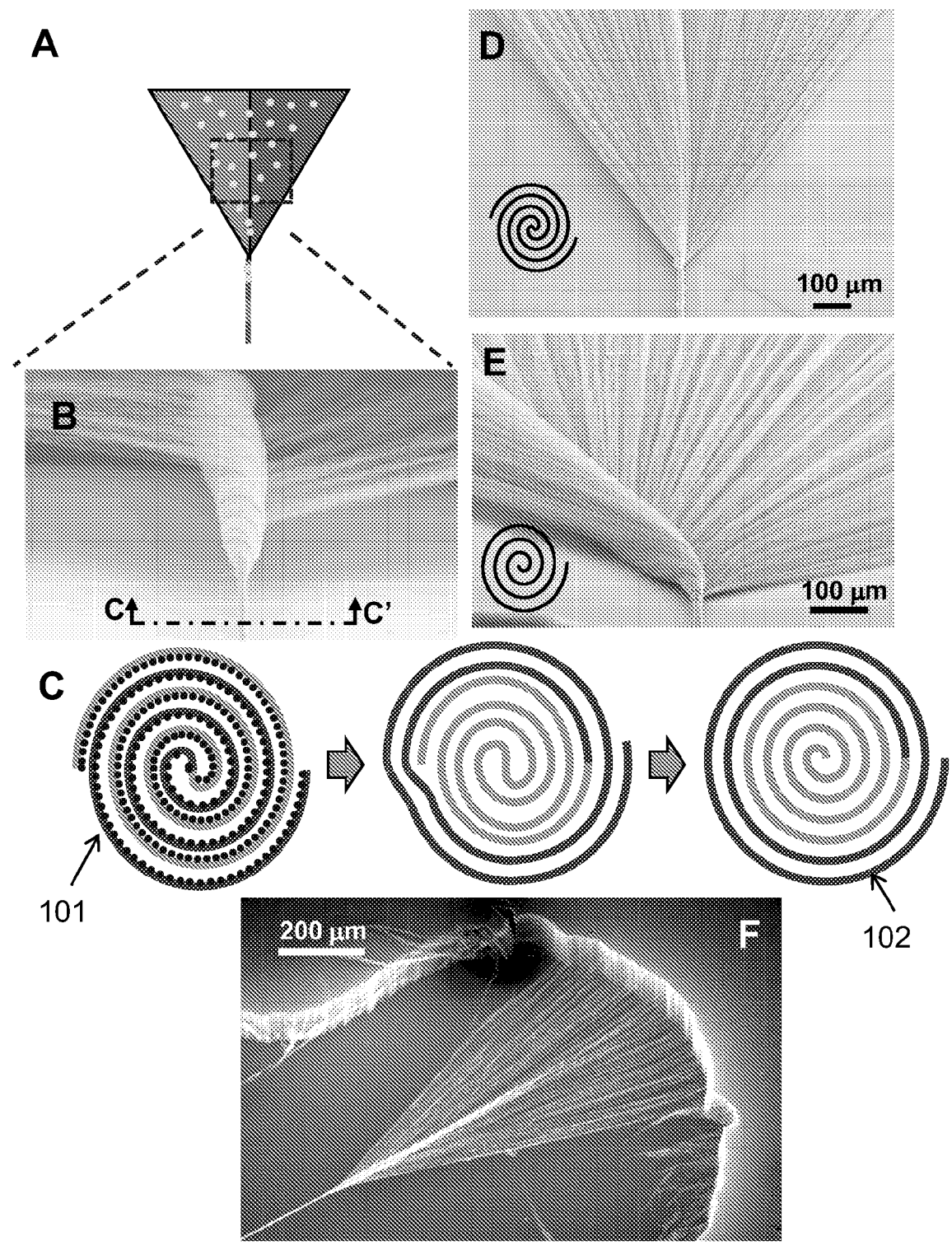
FIGS. 1A-1F show: (1A) a schematic illustration of the biscrolling process with the guest material (dots) deposited on the spinning wedge of the host; (1B) a Scanning Electron Microscope (SEM) image of Fermat scrolling from a twist-produced spinning wedge drawn from a CNT forest; (1C) a schematic illustration of transition from a Fermat scroll 101 to an Archimedean scroll 102; (1D) a SEM image of a largely symmetric twist-produced spinning wedge with pleats, which was drawn from a CNT forest; (1E) a SEM image showing a highly unbalanced Fermat scroll that is, to a good approximation, an Archimedean scroll; and (1F) a SEM image of Fermat scroll formation from a largely pleat-free spinning wedge drawn from a CNT forest.

The present invention is directed to configure functional nanoparticles, nanofibers, and nanoribbons as the major component of weavable yarns that can perform, for example, as superconductors; battery and fuel cell electrodes; antennas; catalytic convertors; hydrogen storage media, and carriers of biological and biopharmaceutical materials.

Embodiments of the present invention involves twist-based spinning of carbon nanotube sheets (the host) that are overlaid with up to about 99 weight percent of one or more other functional materials (the guest). Whether the overlaid functional material comprises nanoparticles, nanofibers or larger guests, the sheet-derived helices in the resulting yarns contain this functional material in a complex three-dimensionally extended spiral, or a combination of spirals, whose structure critically depends upon twist and geometrical and mechanical parameters. As used herein, these yarns containing host and guest scrolls are referred to as biscrolled yarns. The abbreviation guest@host can be used to designate the biscrolled yarn type.

While provided results extend biscrolling to other host nanofibers, including host nanofibers other than carbon nanotubes, the predominately deployed host scrolls of invention embodiments are from drawable multiwalled carbon nanotube (MWNT) forests made by chemical vapor deposition (CVD). [M. Zhang et al., *Science* 309, 1215 (2005) ("Zhang 2005"); and the '982 Application].

1. Host Materials and Properties

The host material for biscrolling can preferably comprise a network of interconnected nanofibers. Various nanofibers and nanofiber syntheses and fabrication processes can be usefully deployed, as can be mixtures of different nanofiber types and mixtures of nanofibers with other materials.

Undensified and densified carbon nanofiber aerogel sheets provide especially useful host materials of invention embodiments, as have been described in the '982 Application and Zhang 2005. The CNT sheets can be in the forms of free-standing sheets or those on a substrate. The substrate can be optionally removed after guest particle deposition. These free-standing sheets and those on a substrate can be either densified or undensified. A particularly convenient method for causing sheet densification is by using surface tension effects due to the process of liquid infiltration and subsequent liquid evaporation.

While various types of carbon nanotube networks can be deployed as host for embodiments of the invention, aerogel sheets will first be described that can be drawn from forests of carbon multiwalled nanotubes (MWNTs), carbon few wall nanotubes (FWNTs), and carbon single wall nanotubes (SWNTs). Unless otherwise indicated, the carbon nanotube host used in described experiments to make biscrolled yarns was synthesized by forest growth, and drawn from a nanotube forest (as described in the '982 Application and Zhang 2005).

Carbon nanotube sheets are drawn from forests of approximately parallel nanotubes, overlaid with the guest, and then twist spun using methods, such as like those methods used for making pure carbon nanotube yarns (as described in the '982 Application). These as-produced carbon nanotube sheets have remarkable structure and properties that pertain to biscrolling. [Zhang 2005].

While these sheets are aerogels having a carbon network density of ~1.5 mg/cm$^3$ (close to that of air), these sheets have a specific strength (i.e., strength normalized to density of up to 144 MPa/(g/cm$^3$), which is above that of ultra-high-strength steel plate. Sheet areal density is very low (typically 1 μg/cm$^2$ to 3 μg/cm$^2$), and densification decreases sheet thickness to as low as ~50 nm and increases sheet specific strength to ~560 MPa/(g/cm$^3$). [Zhang 2005]. The densified aerogel sheets obtained by the twist-based spinning process provide the strong webs needed for confinement of guest materials in a helically scrolled gallery. The high electrical conductivities for the densified sheets, as well as gallery thicknesses that can approach the smallest dimension of the host particles, means charge collection is facilitated for poorly conducting multifunctional guests. FWNT and SWNT forests can be similarly processed into nanofiber sheets and yarns [X. Zhang et al., *Advanced Materials* 19, 4189-4201 (2007)], so they can also be used as host for invention embodiments.

In addition to ordinary MWNTs or SWNTs or FWNTs that have circular or approximately circular cross-sections, SWNTs or FWNTs that have sufficiently large diameters to collapse into ribbons are also useful in embodiments of the present invention, both as host and guest.

Such collapsed nanotubes can be provided by chemical vapor deposition in the gas phase and subsequently assembled as oriented sheets having arbitrarily small thicknesses [U.S. Patent Application Publication No. 2005/0006801, published Jan. 13, 2005]. Also, chemical vapor deposition in the gas phase of MWNTs, SWNTs, and FWNTs and subsequent assembly as oriented sheets having arbitrarily small thicknesses has been described. [PCT Int. Pub. No. WO 2009/029341 A2, published Mar. 5, 2009; Y. Li et al., *Science* 304, 276 (2004)]. These sheet fabrication methods, where the nanotubes (or other nanofibers) are grown by CVD in the gas phase, are useful for producing fabricated host or guest materials for embodiments of the present invention.

It is not required that nanofibers include carbon to be useful for embodiments of the present invention, and various processes are well known in the art for making nanofibers that are not carbon based. Some examples are the growth of superconducting $MgB_2$ nanowires by the reaction of single crystal B nanowires with the vapor of Mg [Y. Wu et al., *Advanced Materials* 13, 1487 (2001)], the growth of superconducting lead nanowires by the thermal decomposition of lead acetate in ethylene glycol [Y. Wu et al., *Nano Letters* 3, 1163-1166 (2003) ("Wu 2003")], and the synthesis of lead nanowires by templating lead within channels in porous membranes or steps on silicon substrates (Wu 2003). The latter methods and various other methods of producing metallic nanowires of types suitable for the practice of invention embodiments are described in Wu 2003, and are elaborated in associated references. Y. Li and coworkers have shown how to make bismuth nanotubes. [N. Li et al., *J. Am. Chem. Soc.* 123, 9904-9905 (2001)]. While all of these nanofibers can be used as guests in biscrolled yarns, the most useful host nanofibers are those that can be configured as sheets having high specific strength, most preferably above about 50 MPa/(g/cm$^3$). The reason is that high sheet strength enables the effective confinement of guest particles in the scrolled corridors of guest, as well as high strength for the biscrolled yarn.

Insulating or poorly conducting nanofibers are also suitable for embodiments of the present invention as long as these nanofibers form an interconnected network.

Nanofibers that are scrolled on the nanometer scale are also useful for embodiments of the present invention. These nanoscrolls are individual sheets or a thin stack of sheets of a layered material that automatically wind to make a scroll (which is structurally analogous to a jelly roll). Almost any sheet-like material can self-assemble into scrolls—as long as the lateral sheet dimension is sufficiently large that the energy gain from non-covalent binding between layers of the scroll can compensate for the elastic energy cost of forming the scroll.

Since scrolls can be made by simply exfoliating materials that are presently made in high volume at low cost, yarns of embodiments of the present invention can also be made at low cost. Methods of synthesizing nanoscrolls of a host of layered materials are known, and these methods can be used for the practice in embodiments of the present invention. [See L. M. Viculis et al., *Science* 299, 1361-1361 (2003); Z. L. Wang, *Advanced Materials* 15, 432-436 (2003); X. D. Wang et al., *Advanced Materials* 14, 1732 (2002); W. L. Hughes et al., *Applied Physics Letters* 82, 2886-2888 (2003); J. W. Liu et al., *Journal of Physical Chemistry B* 107, 6329-6332 (2003); and Y. B. Li et al., *Chemical Physics Letters* 375, 102-105 (2003)].

Nanofibers that are ribbons of graphene sheets are useful as both guests and hosts in embodiments of the present invention. One preferred method for making the graphene ribbons as high aspect ratio nanofibers is by using the known unzipping of carbon nanotubes. [D. V. Kosynkin et al., *Nature* 458, 872-826 (2009)].

Nanofibers and particles of organic electronically conducting polymers are useful as guests for embodiments of the present invention. Some examples are rubber elastic polypyrrole, polyaniline, or polythiophene that contain sulfonated poly(styrene-ethylene/butylene-styrene) as a polymeric dopant [Q. Xue et al., Chinese Patent CN 1410486A (2003)] and polyaniline doped with the di-2-butoxy-2-ethoxy-ethyl ester of sulfosuccinic acid [W. Takahima et al., *Sensors and Actuators B* 99, 601 (2004)]. Examples of useful elastic conducting polymers of polypyrrole and tri-block polyelectrolyte are found in B. Chu et al., *Proceedings of the American Chemical Society* (2006)].

Biscrolling has been extended to electrically insulating hosts: arrays of hollow $SiO_2$ and $Si_3N_4$ nanotubes as described in Example 19. Individual carbon nanotubes and nanotube bundles in free-standing, forest-drawn MWNT sheets were conformably coated with ~10 nm thickness of $SiO_2$ or $Si_3N_4$ produced by plasma-enhanced CVD. Free-standing nanotube sheets were subsequently obtained by removing the carbon nanotube cores (by combustion in air at high temperature or in ozone at room temperature). Both the ceramic coated carbon nanotube sheets and the thereby derived ceramic nanotube sheets can be twist spun to make a yarn, and both can be overlaid with other functional materials to enable the spinning of biscrolled yarns.

As an example, a $Si_3N_4$ coated carbon nanotube sheet was biscrolled with 3.7 wt. % Pt nanoparticles (deposited by e-beam evaporation) to make a mechanically robust yarn. Relevant for application of the ceramic-coated carbon nanotubes as host for biscrolled yarn, conformally coating the carbon nanotubes with ~10 nm thickness of $SiO_2$ does not significantly effect in-plane sheet conductance or the conductance of twisted yarns.

2. Deposition Methods for Guest Materials

The biscrolling methods of embodiments of the present invention involve deposition of the guest material onto (1) a carbon nanotube sheet wedge that results from direct twist-based spinning from a forest or (2) a self-suspended nanotube sheet or sheet stack obtained by sheet draw from a forest. Various host nanofiber web can also be usefully deployed as described in Section 1 above. Deposition of guest materials can be accomplished using all conventional methods that can result in a layered stack of guest and host.

In some embodiments of the present invention, liquid-free deposition is preferably used. Electrostatic deposition of guest onto the nanotube web (i.e., sheet or sheet wedge) from a carrier gas using an electrostatic powder coating gun is fast and controllable—attraction between charged guest particles and the grounded or oppositely charged target web helps in creating a uniformly deposited layer of guest particles over the deposition area (as described in Example 10).

Other liquid-free biscrolling processes involve deposition of the guest material by electron beam evaporation (as described in Example 4), sputtering, chemical vapor deposition (CVD), plasma-enhanced CVD (as described in Example 6), dry powder airbrush deposition (as described in Example 9), or deposition of gas-dispersed guest nanoparticles immediately after their formation by reaction of gases (as described in Example 8).

Liquid state and quasi-liquid-state guest deposition also work, such as electrophoretic deposition (as described Example 2); solution filtration-based deposition using the nanotube sheet stack as a filter to capture guest nanoparticles (as described in Example 3); drop casting (as described in Example 1), and ink-jet printing (as described in Example 7).

Ink jet printing of guest is effective even for self-supported individual nanotube sheets having such low areal density as 1 $\mu g/cm^2$ and can be conveniently used to provide patterned depositions of one or more guest materials—thereby leading to engineered variation in guest composition along the yarn length and along the yarn diameter.

In the filtration method, (a) solid-state-fabricated nanotube sheet strips were placed on top of filter paper; (b) liquid-dispersed nanoparticles/nanofibers were deposited on top of the nanotube strips by filtration; (c) the filter paper substrate was dissolved by a solvent; and (d) twist-based spinning on the bilayer ribbon stack was accomplished in the liquid bath (as described in Example 11). This method can be practiced for any guest nanomaterials that can be liquid dispersed, such as by ultrasonication.

Other methods can be effectively used for guest deposition on a nanofiber host web. For example, the deposition of platinum nanoparticles from a supercritical fluid on carbon nanotubes has been described for other purposes. [C. H. Yen et al.; *Journal of Nanoscience and Nanotechnology* 5, 1852-1857 (2005)].

3. Biscrolling Methods

It has been demonstrated that various methods (both liquid-free and liquid state) can be deployed to deposit guest materials onto the host webs. These bilayered ribbons can be subsequently twisted to make yarns. Similarly, it has been shown that guest material can be continuously deposited onto ribbon (or wedge) drawn from a nanotube forest, and can be subsequently twisted to make yarn. All twist-based spinning methods also work for embodiments of the present invention (as described in the '982 Application).

Various known methods of twist insertion can be used for introducing twist during spinning into yarns. Such methods include, but are not limited to, ring spinning, mule spinning, cap spinning, open-end spinning, vortex spinning, and false twist spinning technologies. [See E. Oxtoby, Spun Yarn Technology, Butterworths, 1987 and C. A. Lawrence, Fundamentals of Spun Yarn Technology, CRC Press, 2002]. Mule spinning has the disadvantage of being a batch process (spin then wind-on), but has the advantage of not requiring rings or travelers. Twist-based spinning methods, rather than false twist methods, are generally preferred for embodiments of the present invention.

Example 11 shows that the bilayer ribbon stack formed on filter paper can be converted into biscrolled yarn using twist-based spinning in liquid bath. The nanoparticles/nanofibers can be deposited on top of the nanotube strips by various deposition methods (both liquid-free and liquid state); the filter paper substrate is dissolved by a solvent; and twist-based spinning on the bilayer ribbon stack is accomplished in the liquid bath. An advantage of this method is that it can be practiced for any guest nanomaterials. A disadvantage of this method is that eventual removal of the liquid from the biscrolled yarn causes yarn densification, which can distort the shape of the yarn cross-section and lead to irregular spiral corridors for guest containment. Upscale for continuous production of biscrolled yarns for commercial applications would likely favor the absence of liquids for both guest deposition and twist-based spinning.

In some embodiments of the present invention, another preferable method of spinning bilayered ribbons into biscrolled yarns is to employ a direct spinning method that twists as it winds the spun yarn onto a bobbin. The apparatus is outlined schematically in the '982 Application. Advantages of this direct spinning method include that the coincidence between the spinning and yarn axes eliminates the spinning balloon and the yarn does not make contact with any surfaces until after the twist is inserted, by which time it has sufficient cohesion to be handled without disruption. The twist level can be set independently of the wind-on by running the wrap and twist drives independently of each other using variable speed motors.

False twist spinning as described in the '982 Application, can also be deployed for the embodiments of the present invention.

4. Structure of Biscrolled Yarns

Figure 2:
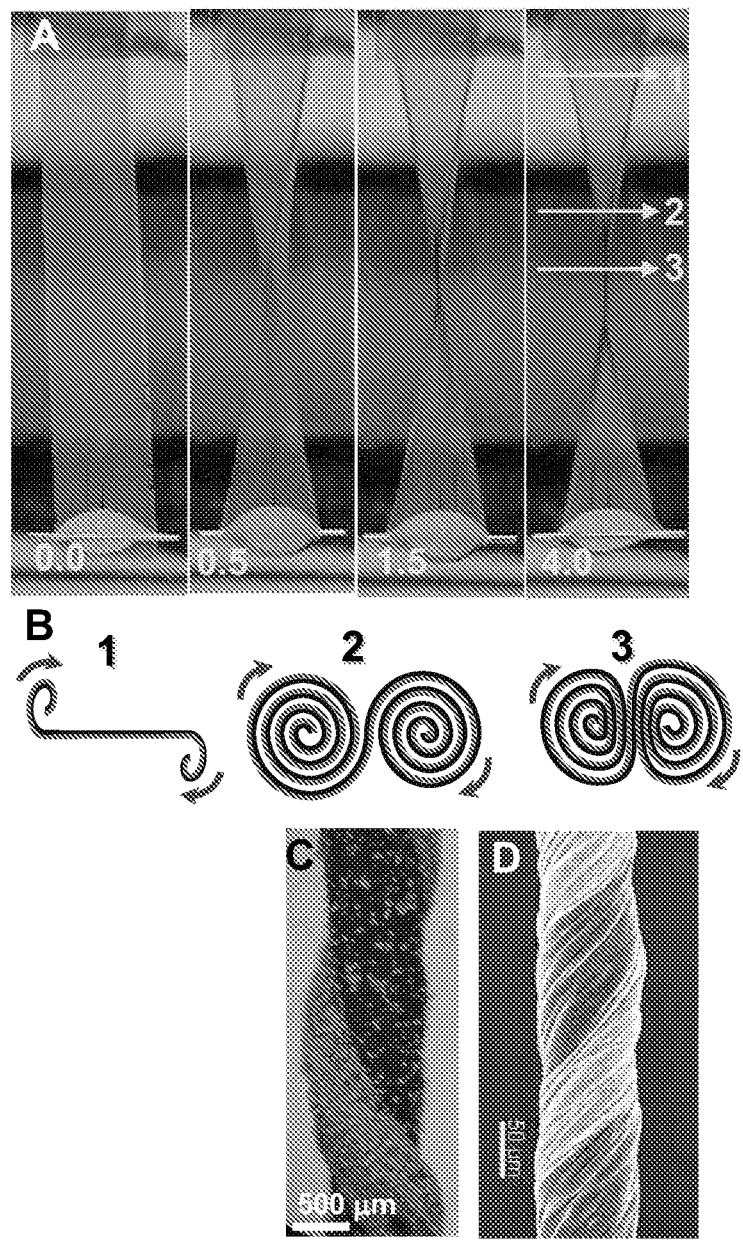
FIGS. 2A-2D show: (2A) images of twisting process in liquid where the numbers at the bottom (i.e. 0, 0.5, 1.5, and 4.0) indicate the number of turns of inserted twist; (2B) schematic illustration of cross-sectional structure at the locations indicated in (2A); (2C) image of biscrolled CNT yarn having red pigment as guest; and (2D) SEM image of biscrolled titanium@MWNT yarn.

The biscrolled yarns provide fascinating structural complexity and diversity (FIGS. 1-3), which were characterized during and after spinning using optical and scanning electron microscopies.

Different yarn topologies were observed for different spinning conditions and resulting structural parameters (like the "wedge angle", the total apex angle where the wedge converges to yarn, the width of the spinning wedge base, and the symmetry of stresses applied during spinning). These observed topologies (see FIGS. 1-3) are related to Archimedean and Fermat spirals and more complicated interconnected spirals. Accordingly, ignoring the radial dependence of interlayer spacings within the scroll, the extreme limits of the topologies that were observe for both biscrolled and guest-free yarns were named by the inventors as Archimedean, Fermat, and Archimedean pair scrolls.

"Archimedean" means that a sheet edge is buried deep in a scroll.

"Archimedean pair" means that the opposite sheet edges are buried in different interconnected Archimedean scrolls.

For an ideal "Fermat scroll," sheet edges are exterior to the scroll, though asymmetric formation of a Fermat scroll as a result of asymmetric applied stress on the spinning wedge can drag one sheet edge to an internal location. If this sheet edge is fully displaced to scroll center, such unbalanced Fermat scroll becomes an Archimedean scroll, as schematically illustrated in FIG. 1C.

These designations provide a starting point for understanding the more complex and interesting observed cross-sectional structures of biscrolled yarns.

FIG. 1A shows a schematic illustration of the biscrolling process with the guest material (dots) deposited on the spinning wedge of the host. FIG. 1B shows a Scanning Electron Microscope (SEM) image of Fermat scrolling from a twist-produced spinning wedge drawn from a CNT forest. The transition from a Fermat scroll 101 to an Archimedean scroll 102 is schematically illustrated in FIG. 1C. FIG. 1D shows a SEM image of a largely symmetric twist-produce spinning wedge with pleats, which was drawn from a CNT forest. FIG. 1E is a SEM image showing a highly unbalanced Fermat scroll that is, to a good approximation, an Archimedean scroll. FIG. 1F shows a SEM image of Fermat scroll formation from a largely pleat-free spinning wedge drawn from a CNT forest.

In FIG. 2A, images of a twisting process in liquid are shown where the numbers at the bottom (i.e. 0, 0.5, 1.5, and 4.0) indicate the number of turns of inserted twist. FIG. 2B shows a schematic illustration of cross-sectional structure at the locations (1, 2, and 3) indicated in FIG. 2A. FIG. 2C is an image of a biscrolled CNT yarn having red pigment yarn as guest. FIG. 2D shows a SEM image of a biscrolled titanium@MWNT yarn.

Figure 3:
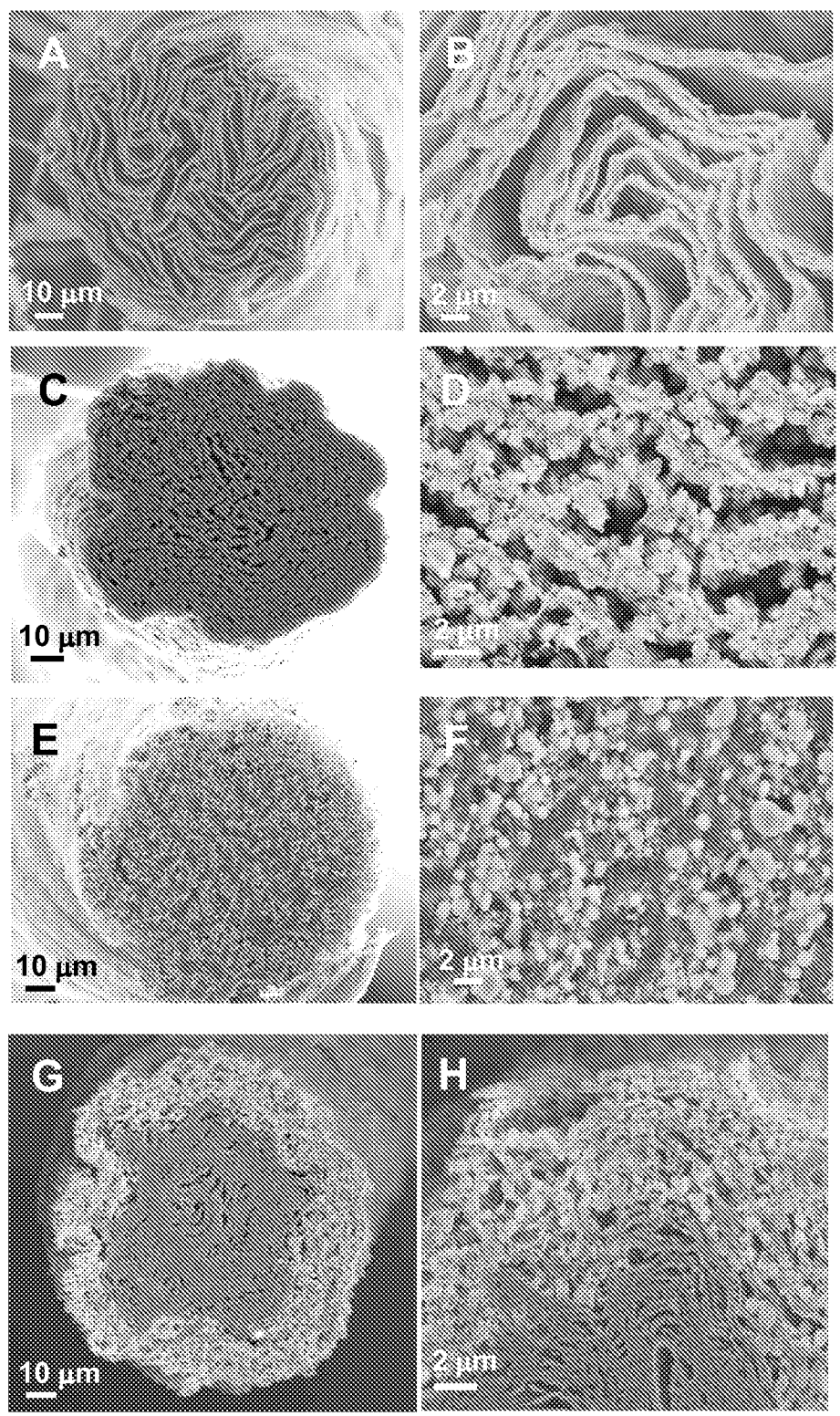
FIGS. 3A-3H show SEM images of the cross-sections obtained by cutting biscrolled yarns using a focused ion beam: (3A) biscrolled titanium@MWNT yarn prepared using the process described in Example 4 and Example 11; (3B) higher magnification of (3A); (3C) biscrolled $TiO_2$@MWNT yarn prepared using the process described in Example 3 and Example 11; (3D) higher magnification of (3C); (3E) biscrolled $TiO_2$@MWNT yarn prepared using the process described in Example 8; (3F) higher magnification of (3E); (3G) biscrolled $TiO_2$@MWNT yarn prepared using patterned filtration (described in Example 3), then twisted into an Archimedean scroll; and (3H) higher magnification of (3G). The darker inner area is MWNTs and lighter outer area is $TiO_2$/MWNTs.

FIGS. 3A-3H show SEM images of the cross-sections obtained by cutting biscrolled yarns using a focused ion beam. FIGS. 3A-3B are SEM images of a biscrolled titanium@MWNT yarn prepared using the process described in Example 4 and Example 11. FIGS. 3C-3D are SEM images of a biscrolled $TiO_2$@MWNT yarn prepared using the process described in Example 3 and Example 11. FIGS. 3E-3F are SEM images of a biscrolled $TiO_2$@MWNT yarn prepared using the process described in Example 8. FIGS. 3G-3H are SEM images of a biscrolled $TiO_2$@MWNT yarn prepared using patterned filtration (described in Example 3), then twisted in Archimedean scroll. In the SEM images of FIG. 3, the darker area is MWNTs and lighter area is $TiO_2$/MWNTs.

The results of this embodiment of the present invention indicate differences that arise between continuous twist-based spinning from a nanotube forest sidewall (via a twist-produced spinning wedge) and formation of yarn by twisting a preformed rectangular nanotube sheet between end supports.

In ideal Fermat biscrolling (or scrolling for a guest-free yarn), the twist process starts from the center of a spinning wedge, as shown in FIGS. 1A-1D. The edges of the spinning wedge wrap (i.e., scroll) in opposite directions about the thereby formed center core, so that a helically extended spiral is formed in which wedge edges are exterior to the scroll. Asymmetry in the stress applied to opposite sides of the spinning wedge can displace the center of the Fermat scroll from the center of the spinning wedge, so that one side of the spinning wedge twists on top of one edge of the Fermat scroll, thereby burying this edge in an unbalanced Fermat scroll. (See FIG. 1C). If the spinning core reaches a wedge side (see FIG. 1E), an unbalanced Fermat scroll can become an Archimedean scroll. Use of a large wedge angle shifts tensile stresses and resulting twist accumulation to wedge edges, which facilitates transition from Fermat scroll formation to edge-based Archimedean scroll formation.

Increasing the wedge angle and the spinning wedge base width introduces pleats (i.e., folds) for all scroll types, whose amplitude increases during convergence of the spinning wedge to yarn, except near wedge apex where twist can partially relieve width-direction strain. The origin of these pleats is the same as for an initially flat hanging curtain, with fixed top-end supports, that is bunched together at the bottom to form a wedge—pleats form with amplitude that increases from unstrained top to bunched bottom, so as to fit the initial sheet width into a decreasing wedge width (FIG. 1D-1E). Pleat formation during forest spinning can be avoided by using a very narrow wedge base width and small wedge angle, like observed for conversion of a 500 μm wide forest sidewall width into a 4 μm diameter yarn using a wedge angle of about 38° (FIG. 1F).

For twist-based spinning directly from a nanotube forest, the wedge angle is determined by relative rates of draw and twist.

Spinning a given length of rectangular sheet strip under constant load is more complicated than dynamically stabilized continuous spinning from a forest-derived wedge. Twist of a rectangular sheet between end supports starts with sheet folding that is origami-like, except that plastic deformation of sheet area occurs, which repeats during subsequent rotations to form a new system of folds until a spinning wedge is obtained. The wedge angle then increases with increasing twist.

FIG. 2A shows a case where Archimedean scrolls form at both wedge edges, even though the wedge angle is small. The predominance of Archimedean scroll formation for twisting a short rectangular sheet or sheet stack in air or in liquids is likely a result of the propagation of twist along the wedge edges, where tensile stresses are higher because of the constrain of the fixed end supports.

The above edge-generated scrolls having opposite handedness, which are either Archimedean scrolls or highly unbalanced Fermat scrolls, are ultimately twisted together like for a two ply yarn. FIGS. 2A-2D. Though both Archimedean scrolls volumetrically include guest, the guest is exterior to the scroll surface for one scroll and interior for the second. Hence, when the two Archimedean scrolls are ultimately twisted together as the spinning wedge converges to yarn, the observed barber-pole-like structure results FIGS. 2C-2D.

On the other hand, applying sufficiently unequal loads to opposite sides of the bilayered sheet results in observation of only one Archimedean scroll, and the surface of the yarn shows only a single side of the original bilayer-stack. The side forming the external surface of this yarn can be changed by changing the side of the sheet that is most stressed or by changing from clockwise or counterclockwise twist.

The following results were observed: While twisting a bilayered rectangular sheet between rigid end supports resulted in either single Archimedean or dual Archimedean scrolls (depending, respectively, on whether asymmetric or symmetric forces were applied during twist), Fermat scrolling had not been observed for these spinning conditions. However, if one end of the rectangular sheet was attached to a suitable non-rigid support, like a forest side-wall, the spinning wedge attached to this support, which arises during twist, can produce a Fermat scroll (for symmetric spinning) or a single Archimedean scroll, as well as states between these extremes (but not a dual Archimedean scroll). Continuous wedge-based spinning from a forest sidewall also produced these types of scrolls.

As shown in FIG. 3, SEM microscopy of the cross-sections obtained by cutting biscrolled yarns using a focused Ga ion beam, revealed irregularity in the corridor structure that confines the guest particles. This raises the question as to why the observed galleries of host and guest in FIGS. 3A-3H are so complicated and irregular when the images in FIGS. 1-2 clearly show that scrolling and biscrolling is structurally related to three-dimensional extension of Fermat, Archimedean, or dual Archimedean spiral geometries.

One partial answer of this question for the most investigated structure (FIGS. 1A-1B) is that macroscopic observations during spinning indicates complex plying of two Archimedean scrolls to form the biscrolled yarn, which is consistent with the barber-pole-like structure for the same yarn, as shown in FIG. 2D.

Another likely partial answer is in the initial formation of low-density, biscrolled core structure, nanotube scroll layers are unable to easily glide with respect to neighboring guest layers during further twist that results in the final densified yarn structure. Since the sheet is very weak orthogonal to the nanotube orientation direction, resulting partial local separation of the nanotubes in this orthogonal direction can produce holes in the scrolled sheets, which appear as occasional breaks in the scroll for any given cross-section. Additional irregularity likely results from the observed pleating caused by non-uniform stress across the spinning wedge, non-uniformities in guest particles size and their aggregation within the guest layer, differences in the stresses applied to opposite sides of the spinning wedge, and yarn shape distortion caused by twist in a liquid bath and the resulting yarn densification caused by surface tension during subsequent evaporation of the liquid.

When the uniform coating of guest on one side of a sheet or sheet wedge was replaced with a coating of guest that was only on fraction of the sheet surface (such as adjacent to one sheet edge) and twist was applied asymmetrically so that formation of a single Archimedean scroll was macroscopically observed, a core-shell structure was observed where the guest was only in the corridors of the core or shell (depending in part on the wedge half that was preferentially stressed). This is illustrated in the yarn structure shown in FIGS. 3G-3H, for one-side deposition of particles of $TiO_2$ on only 15% of rectangular sheet area used for spinning. Deploying a single Archimedean scroll that starts from the $TiO_2$-free side of the wedge, an inner core of uncoated nanotube sheet is co-axially surrounded by an outer sheath that has $TiO_2$ particles in its corridors.

This ability to profile guest distribution in the biscrolled fiber is very useful. For example, preferential location of $TiO_2$ on the shell can increase accessibility of light to functional guests, for example for the application of $TiO_2$ biscrolled yarns for dye-based electrochemical solar cells and for the use of $TiO_2$ guest in biscrolled yarns for light enabled textile cleaning or destruction of biological or chemical threats.

The capabilities of the biscrolling process of the present invention for achieving needed performance is additionally increased by the convenient ability to deposit the same or different guest on one or both sides of the host web (sheet or spinning wedge), and to accomplish this in a convenient patterned manner, such as by ink jet printing.

5. Mechanical Properties of Biscrolled Yarns

Long carbon nanotube length can be important for achieving useful mechanical properties of biscrolled yarns and effective confinement of guest materials. An individual nanotube (presently ~400 µm long) can wrap though many spiral revolutions for thin yarns (which can have diameters below 10 µm). Also, extensive nanotube bundling and self-weaving within biscrolled sheets though bundle forking and recombination with other forks can increase the ability of scrolled nanotube sheets to confine a guest.

$TiO_2$@MWNT biscrolled yarns of the present invention were prepared using the filtration method, as well as by other deposition methods. In the filtration method $TiO_2$ powder was suspended in 1% SDS solution and filtration-deposited onto a two-layer CNT sheet stack that was placed on a cellulose nitrate membrane. Another layer of CNT sheet was then overlaid on top of the $TiO_2$ layer to confine the guest material. The rectangular $TiO_2$@MWNT sheet stack (6 mm×30 mm) was cut from the membrane and immersed in acetone to dissolve the membrane. The free standing $TiO_2$@MWNT sheet stack was then twisted along its length axis using a magnetic stirrer located under the acetone bath, which coupled to a steel rod that is glued to the sheet stack.

Biscrolled $TiO_2$@MWNT yarns with guest weight concentrations of 0%, 24%, 62%, and 93% were prepared using the above procedure, and then tested for mechanical properties.

The mass of these biscrolled yarns were measured using a microbalance. Specific mechanical properties were determined from measurements of force versus strain at 4%/minute engineering strain rate using a tensile test apparatus (Favimat 37617).

Figure 4:
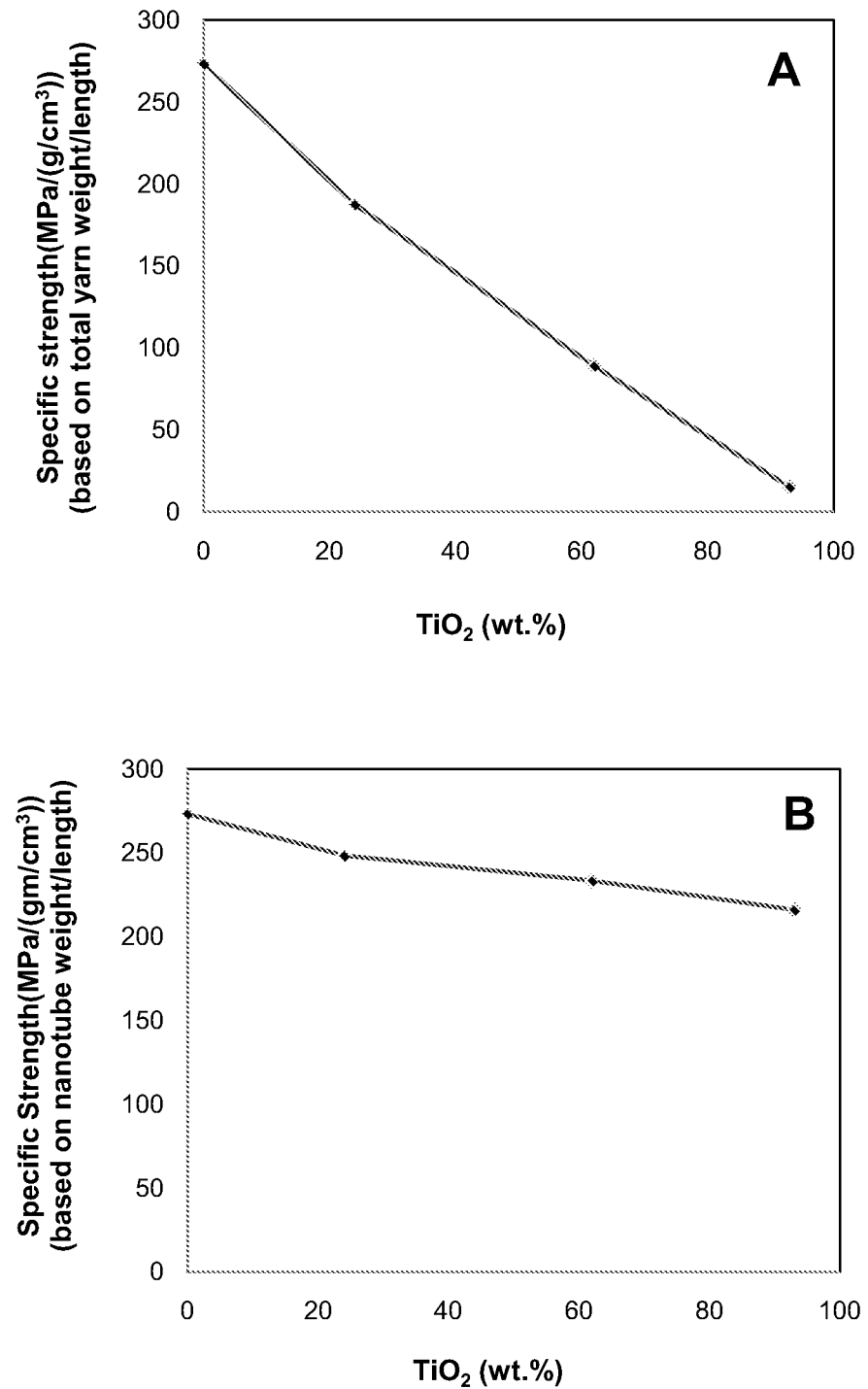
FIGS. 4A-4B show (4A) a graph plotting yarn specific breaking strengths versus $TiO_2$ weight concentration; and (4B) a graph plotting MWNT-normalized specific breaking strengths versus $TiO_2$ weight concentration. These results are for biscrolled TiO2@MWNT yarns made using filtration-based deposition of $TiO_2$ powder.

FIG. 4A shows a graph plotting specific yarn breaking strengths versus $TiO_2$ weight concentration. The guest-free nanotube yarn has a specific strength of 273 MPa/(g/cm$^3$), which is comparable to that of a densified MWNT sheet stack. As the $TiO_2$ concentration increases, the specific breaking strength of the $TiO_2$@MWNT biscrolled yarn decreases approximately proportionally. See FIG. 4A.

This suggests that the guest component ($TiO_2$) did not contribute to the mechanical strength of the biscrolled $TiO_2$@MWNT yarn, which is expected because of the powder nature of the $TiO_2$.

More surprisingly, even high concentrations of $TiO_2$ did not dramatically degrade the nanotube contribution to biscrolled yarn specific strength. This is indicated in FIG. 4B, which is a graph in which the yarn breaking force normalized to CNT mass/length (rather than total yarn mass/length) was plotted versus $TiO_2$ concentration. Since the CNT-normalized specific breaking strengths showed small dependency on $TiO_2$ concentration, this confirmed that the contribution of the scrolled CNT network to yarn strength was little effected by even high $TiO_2$ concentrations.

6. Applications of Biscrolled Yarns

The broad applications potential of biscrolling is suggested by the following described demonstrations in which scrolled nanotube sheets confined the following functional materials in the spiral corridors of yarns: superconductors, graphene ribbons, $TiO_2$ for destruction of biological threats, high performance battery redox materials, and biological agents. These demonstrations indicate retention or acquisition of guest functionality, and the ability of small amounts of nanotubes to contain massive amounts of functional materials in yarn sacks. Because of the very high thermal and chemical stability of the carbon nanotube containers for biscrolled nanotube yarns, extreme thermal and non-oxidizing chemical environments can be used after yarn fabrication to convert guest components to desired functional components.

(a) Biscrolled Yarns for Superconductor Application

The biscrolling process of embodiments of the present invention enables construction of superconducting yarns. It has been demonstrated that superconducting yarn can be obtained by biscrolling a mixture of boron and magnesium guest powders with a three layer MWNT sheet strip host using filtration-based guest precursor deposition on a two layer sheet stack, overcoating the guest powders with a third MWNT sheet strip, and inserting twist in a liquid (as described in Example 12).

One weight percent carbon nanotubes host held 99 wt % of these precursors for both twist insertion and later processing to produce the superconductor, despite the large diameter of the used B and Mg guest particles (<39 μm, which are like giant boulders compared with the ~50 nm thickness of a densified nanotube sheet). Conversion of this guest material to superconducting $MgB_2$ by exposure of the biscrolled yarn to the highly corrosive vapor of magnesium at high temperature (750° C. for 30 minutes in argon) indicated the ability of the nanotube host to function as yarn sacks in chemical and thermal environments where most materials degrade.

Four-probe electrical conductivity measurements versus temperature showed that the biscrolled yarn was superconducting, with a critical temperature ($T_c$) at the expected temperature (J. Nagamatsu et al., *Nature* 410, 63 (2001)) of about 39 K. This demonstration appears to be important because of the need for superconducting cables and the convenient applicability of biscrolling in the search for new bulk superconductors—providing a useful yarn configuration, accessibility of the superconducting guest to chemical and electrochemical doping, and the ability to easily include multiple nanoparticle/nanofiber components as guests that are in intimate contact for both achievement and modification of superconductivity through proximity effects and increase of dimensionality.

(b) Biscrolled Yarns for Energy Storage Application: High Performance Battery Electrodes The use of biscrolling to produce yarns that function as high performance battery electrodes might have special applications importance, since highly conducting scrolled carbon nanotube sheets can hold in nanoscale proximity poorly conducting guest redox materials that show high energy storage and high rate capabilities.

In some embodiments of the present invention, electrode material with at least two components was prepared, wherein the first component was a carbon nanotube sheet that provided electrical conductivity as well as mechanical support by constraining the second component, which contributed to the incorporation and release of ions like lithium ions. The electrode was prepared with the step of providing the first component, wherein the first component included a carbon-nanotubes sheet or sheet stacks of a variable number of carbon nanotubes sheet layers drawn from a forest or prepared by other method, and adding a second component with the composition $Li_xM_yPO_4$ and/or $C@Li_xM_yPO_4$ with M=Ti, V, Cr, Mn, Fe, Co, Ni dispersed in an aqueous solution. An additional layer of carbon nanotubes can optionally be placed on top of the second component.

In another step, twisting of the composite with 50-99 wt. % active material on top of the carbon nanotube sheet is performed yielding a self standing yarn-like electrode.

Example 14 demonstrates a method wherein biscrolled $LiFePO_4$@MWNT yarns can be fabricated for lithium battery application. The electrodes including $LiFePO_4$@MWNT were prepared by either wet filtration or dry powder deposition methods. For both approaches, the biscrolled $LiFePO_4$@MWNT yarns were then thermally treated at 600° C. for 6 hours in Argon flow environment. The specific capacities have been calculated for the total weight of the electrode. The total weight percentage of the active material in the electrode including current collector can be larger than 90% (typical loading in conventional $LiFePO_4$ electrodes is 70%). The charge and discharge curves at rates of 0.1 C-10 C showed that the material can deliver high specific capacities, about 115 mAh/g of total electrode, without addition of binder (typically 7.5 wt %. PVDF), and with just 1-5% wt. of CNT (compared with 10-15 wt %. of carbon black in conventional electrodes) and without the presence of metallic current collector (usually Al foil making an extra 20 wt. % contribution to the total cathode weight).

In some embodiments of the present invention, graphene@MWNT biscrolled material can be used for energy storage applications as the main part of an electrode material for supercapacitors and batteries. The high achievable gravimetric surface area for such biscrolled yarns is critically important for supercapacitor applications, and can provide high discharge rates for battery electrode applications.

Graphene nanoribbons@MWNT yarns produced as described in Example 13 can be used as anodes in lithium batteries. Because of the high surface area accessible in graphene nanoribbons for the intercalation of lithium ions and corner/edges that contribute to higher storage capacities, higher performance than that for the ordinary graphite ($LiC_6$: 372 mA h $g^{-1}$) have been reported. [E. Yoo et al., "Large reversible Li storage of graphene nanosheet families for use in rechargeable lithium ion batteries", *Nanoletters* 8, 2277-2282 (2008); S. M. Paek et al., "Enhanced Cyclic performance and Lithium storage capacity of $SnO_2$/graphene nanoporous electrodes with three-dimensionally delaminated flexible structure", *Nano Lett.* 9, 72-75 (2009)].

In some embodiments of the present invention (such as, for instance, a lithium ion battery electrode), methods are provided for producing the electrode, as well as the whole battery (by combining two biscrolled electrodes, anode and cathode, in the shape of, for example, a two ply yarn).

In some embodiments of the present invention, a device was obtained in which each electrode was prepared with a first step of biscrolling graphene nanoribbons or other material @MWNT as anode and biscrolling $Li_xM_yPO_4$ or other material@ MWNTs as cathode and a second step of positioning them close to each other, yet electronically insulated by a separator, and adding the electrolyte to form yarn battery.

(c) Biscrolled Yarns for Energy Storage Application: Supercapacitors

In some embodiments of the present invention, biscrolled nanotube sheets can be used to confine high-surface area materials for supercapacitor application. The electrode of biscrolled yarn with at least two components was prepared. The first component was a carbon nanotube sheet that provided electrical conductivity, as well as mechanical support, by constraining the second (guest) component, which had a high surface area for incorporation of the active species from the electrolyte to form an electrochemical double layer by charge injection.

The guest component can be graphene plates or graphene nanoribbons obtained by chemical unzipping CNTs [D. V. Kosynkin et al., *Nature* 458, 872-876 (2009)]. Suitable additional methods of fabricating graphene nanoribbons by CNT unzipping exist. High-quality graphene nanoribbons exhibiting low defect concentration and correspondingly improved electrical conductivity are obtained by using plasma etching of MWNTs [L. Jiao et al., *Nature* 458, 877-880 (2009)] or by using a combination a gas-phase oxidation step with mechanical sonication in organic solvents for MWNTs [L. Jiao et al., *Nature Nanotechnology* 5, 321-325 (2010)].

Another type of particularly useful guest material for biscrolled supercapacitor yarns is provided by the high surface area carbons obtained by reaction of carbides [J. Chmiola et al., *Science* 313, 1760-1763 (2006); Y. Gogotsi et al., *Nature Materials* 2, 591-594 (2003)].

Biscrolled graphene oxide nanoribbons or graphene nanoribbon yarns reduced chemically or thermally can be used as electrodes of supercapacitors. In one embodiment of the present invention, 2 wt % MWNTs host confined 98 wt % guest nanofibers were synthesized by unzipping solution-dispersed MWNTs using $KMnO_4$ in aqueous $H_2SO_4$ as oxidant (as described in Example 13).

Based on the complete disappearance of the ~3.4 Å x-ray diffraction peak for MWNTs after oxidation with a massive amount of $KMnO_4$ (~850 wt %, relative to MWNT weight), the guest nanofibers were largely graphene. Graphene nanofibers (obtained by reduction of the graphene oxide nanofibers) or the precursor graphene oxide nanofibers were deposited, for example, on two stacked layers of forest-drawn nanotube sheet that were supported by a cellulose nitrate filter paper. Filtration-based deposition of the solution-dispersed graphene or graphene oxide nanofibers on top of these host MWNT sheets led to a host-guest sheet stack, which (cut into ribbon form) could be twist spun in an acetone bath that dissolved the filter paper before the start of spinning.

Other highly conducting and high-surface area materials can also be useful for embodiments of the present invention. These materials can be nanoparticles, nanoscrolls, nanoribbons exhibiting good conductivity and high surface area for energy storage. For example, graphene flakes from simple exfoliation of graphite or any other sheet like material that could be scrolled are useful for being the guest material into the host MWNT conducting network.

Nanoparticles and nanofibers of electronically conducting organic polymers are also especially useful for embodiments of the present invention. Electron-acceptor doped nanofibers, nanoparticles and nanoscrolls made of polypyrrole, polyaniline and polythiophene are also especially useful for embodiments of the present invention for providing good flexibility, high output power and high energy storage capability.

Electrical energy storage of these biscrolled electrodes can be performed by using aqueous, organic, and ionic liquids as an electrolyte. In some embodiments of the present invention, an all-solid-state biscrolled yarn supercapacitor can be fabricated by plying two single biscrolled yarns as electrodes. Each biscrolled yarn can be coated with a gel-like solid electrolyte (such as phosphoric acid containing polyvinyl alcohol) to obtain a fiber shaped supercapacitor, like previously done for yarns made by coagulation-based solution processing [A. B. Dalton et al., *Nature*, 423, 703, (2003)]. These biscrolled supercapacitors yarns can be used in a wide range of energy capture and storage applications and are used either by themselves as the primary power source or in combination with batteries or fuel cells. These batteries and fuel cells can be also other biscrolled guest materials containing battery materials, like lithium iron phosphate, and electro-catalyst materials, like nitrogen-doped carbon nanotubes (see following section (d)).

(d) Biscrolled Yarns for Application as Catalytic Oxygen Electrodes

In some embodiments of the present invention, N-doped CNTs ($CN_x$) are used to make $CN_x$@MWNT biscrolled yarns that function catalytically as an oxygen electrode to provide improved performance for such applications as fuel cells. In Example 15, the electrochemical performance of these $CN_x$@MWNT biscrolled yarns in the oxygen reduction reaction (ORR) was tested by cyclic voltammetry (CV) in a three-electrode cell. Similar to the reported in literature [S. Kundu, et al.; *J. Phys. Chem. C* 113, 14302-14310 (2009) ("Kundu 2009")] for conventional electrode geometry, a displacement to more positive potentials (~0.3V) was found for the onset of the ORR for the $CN_x$@MWNT yarns when compared to the control of MWNT@CNT biscrolled yarn electrode.

As the nitrogen sites in $CN_x$ are responsible of this displacement in the reaction [Kundu 2009], this simple test verified the accessibility of the biscrolled $CN_x$ material to the oxygen in the surrounding electrolyte and the retention of catalytic activity. The difference in the absolute values of potential that were found compared with the result in Kundu 2009 is explained in early studies reporting the shift of the ORR peak potential by ±30 mV per 1 at % of N incorporated into the carbon lattice [Matheson et al., *J. Phys. Chem. B* 109, 4707-4716 (2005)]. However, later studies suggested that more than the total nitrogen percentage in the structure, the amount of pyridinic nitrogen is the one responsible for the high activity with respect to ORR. [Kundu 2009; Y Shao, *Applied Catalysis B: Environmental*, 79, 89-99 (2008)].

These biscrolled $CN_x$@MWNT yarns can be used for proton exchange membrane fuel cells (PEMFCs) or other electrochemical applications. The selection of a specific material for biscrolling makes this method usable for tuning the properties of flexible electrodes for specific electrochemical systems or for use in new kinds of galvanic cells (batteries).

(e) Biscrolled Yarns for Additional Applications as Catalyst

Biscrolling for confinement of catalyst particles in yarns that can be woven into textiles is another demonstrated application. Biscrolled yarn textiles can be deployed for maintaining high volumetric concentrations of catalyst in trapped, but highly active state, for liquid or gaseous state catalysis.

Example 20 demonstrates that biscrolled yarns with confined platinum black guest particles show catalytic activity by fast decomposition of hydrogen peroxide solution into water and oxygen. Biscrolled Pt nanoparticles@MWNT yarns were obtained by two methods, a) e-beam deposition of Pt on MWNT sheets placed over a cellulose nitrate substrate, and b) by electrostatic deposition of Pt black nanoparticles directly on MWNT sheets. The high catalytic response of these Pt nanoparticles@ MWNTs was shown by submerging the biscrolled yarn into a $H_2O_2$ solution (30 v %). A high decomposition rate of the $H_2O_2$ (into $H_2O$ and $O_2$) and increase in temperature of the solution was observed. Furthermore, high performance in this application has been demonstrated for Pt guest in scrolled MWNT sheets in which the MWNTs and MWNT bundles are coated with nano-size depositions of $Si_3N_4$ or $SiO_2$, as well as for biscrolled $Si_3N_4$ and $SiO_2$ sheet hosts (as described in Example 19).

(f) Application in Multi-Functional Textiles

The use of biscrolling for making yarns for textiles that are self-cleaning or protective against chemical or biological threats has also been demonstrated. For possible uses as yarns for woven textiles that serve as flexible electrodes, other functional materials were biscrolled into yarn using solid-state-drawn MWNT host. These included biscrolled yarn containing catalytic Pt for fuel cell electrodes and other catalysis needs, metal oxide powders for battery electrodes, and $TiO_2$ for Graetzel solar cells and self-cleaning clothing.

Example 16 demonstrates biscrolled yarns of $TiO_2$ for photocatalytic application. The most widely used photocatalyst is $TiO_2$ due to its high photocatalytic activity (converting photon energy into chemical energy by absorbing light), high stability and non-toxicity. The catalyzed photolysis of $TiO_2$ under ultraviolet (UV) irradiation generates electron-hole pairs that react with water to produce active oxygen and hydroxyl radicals that reacts with organic contaminants.

To test the catalyzed photolysis of the $TiO_2$@MWNT biscrolled yarn, a piece of cotton fabric was dyed by soaking in a solution of the methylene blue, and then dried in a vacuum oven overnight. A biscrolled $TiO_2$@MWNT yarn was then laid overtop the dyed cotton fabric and placed under a mercury UV lamp that provided 365 nm radiation. The intensity of the lamp was 64 $W/m^2$. It was noticed that after 4 hours of irradiation, a bleaching effect was visible even on the reverse side of the dyed fabric, which was neither in direct contact with the biscrolled yarn or exposed to the UV light.

The robustness of $TiO_2$@MWNT yarns for retaining $TiO_2$ during cleaning of textiles (for example using a washing machine) was also investigated using a model system. The robustness test was done on a biscrolled $TiO_2$@MWNT yarn in which the concentration of $TiO_2$ was nearly 93%. The weight of the yarn before washing was measured. The yarn was then immersed in 1% wt. SDS suspension, which was placed on a hot plate with a magnetic stirrer. The yarn was washed by stirring for 3 hours at 80° C. Then the yarn was taken out of the suspension and dried in vacuum overnight. The weight of the yarn was again measured. The percentage of weight loss of $TiO_2$ was less than 2%.

As shown in Example 16 and Example 17, the biscrolled $TiO_2$@MWNT yarns have robust mechanical properties and chemical stability, which are useful properties for exploiting the photo catalytic activity of $TiO_2$ for textile applications.

(g) Application in Biomedical Area

Figure 29:
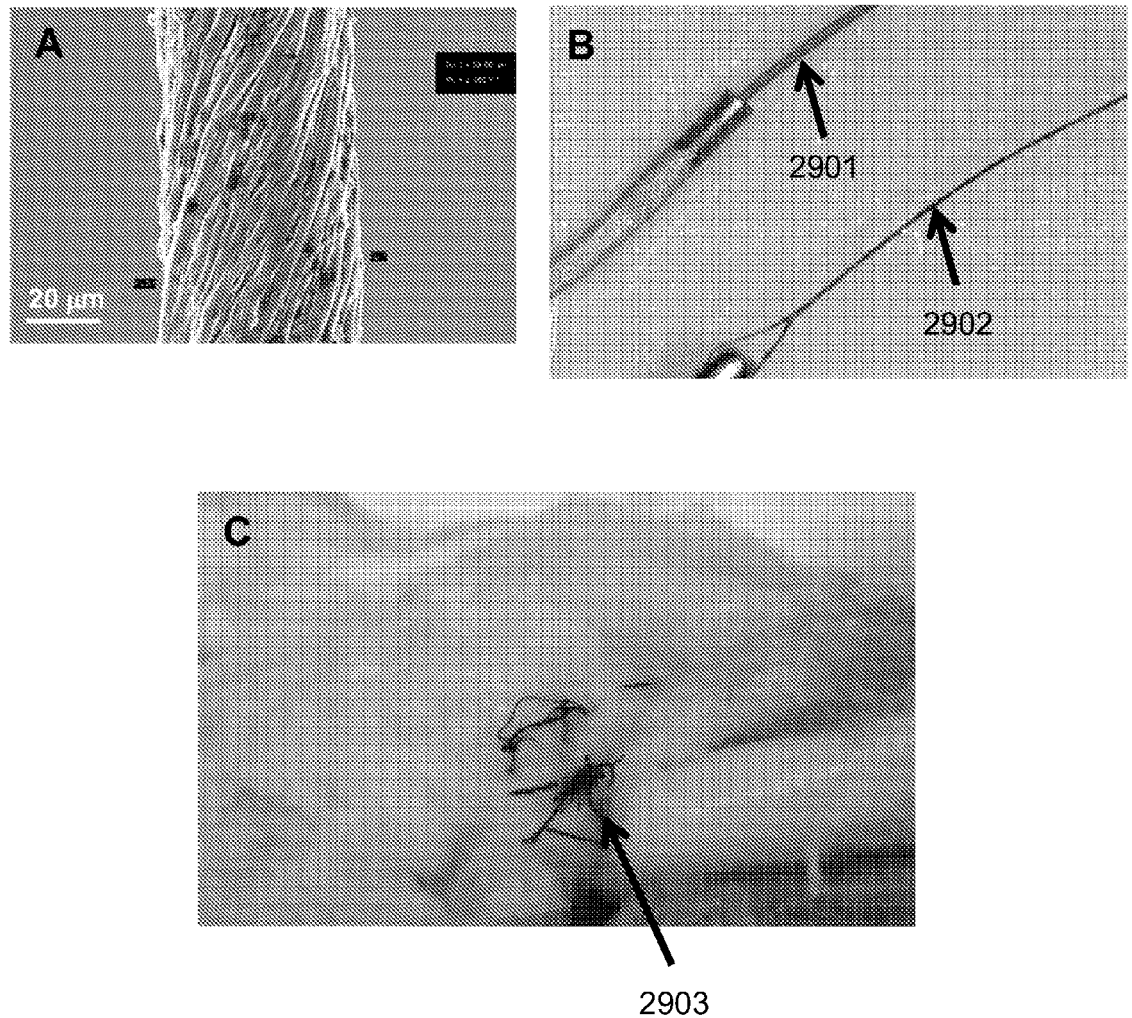
FIGS. 29A-29C show: (29A) a SEM image of a biscrolled antiseptic plus anti-inflammatory yarn with diameter of 53.66 µm, (29B) an image of Monofilament Vicryl 2-0 non-absorbable suture 2901 and an image of the biscrolled antibacterial yarn 2902 as cutaneous suture, and (29C) an image of the forefoot of a butchered pig that was sutured with the biscrolled yarn using simple interrupting stitch 2903.

Example 24 shows the use of biscrolling to confine high concentrations of biologically active agents as guests in yarns that are sufficiently strong to be sewn into muscle. Biscrolled yarns containing up to 95 wt. % biologically active guests were made for such potentials applications as removable sutures and compressive wound dressings. FIG. 29C shows a suture consisting of a single biscrolled yarn that was handmade by draw of a rectangular MWNT sheet from a nanotube forest, spreading 2-10 μm diameter lyophilized antibacterial powder on one side of the MWNT sheet, and then twisting the sheet bilayer.

Despite a high guest loading level of 83.6 wt. % and a small yarn diameter of 53.7 μm (which might reduce scarring), this biscrolled yarn provided useful mechanical performance as a suture.

Initial tests involved threading this biscrolled yarn into a ⅜ circle cutting edge suture needle and subsequent suturing of subcutaneous and cutaneous layers of a full thickness laceration that penetrated into subdermal layers of the foot of a butchered pig (purchased at a grocery store). Suture mechanical properties enabled convenient application of the interrupting suture technique for subcutaneous and cutaneous skin layers, as well as the horizontal mattress suture technique for cutaneous skin in areas of high tension and movement (where a single biscrolled yarn is stitched parallel to the wound edges). These sutures were easily quadruply knotted for closure using square knots.

Because of high strength, flexibility, porosity, and small achievable yarn diameters, biscrolling diverse powders can be used to provide biomedical functions, assuming that either carbon nanotubes are eventually found safe or this host is replaced by other host nanofibers. Biscrolling neuronal growth agents are useful for providing nanotube electronic interconnections to targeted nerve cell types, especially since nerve degeneration at metal wire contacts is a problem and since neurons appear to propagate normally on forest-drawn nanotube yarns and sheets.

Other applicable biomedical uses range from biometric sensors (implantable or external), hemostatic compressive dressings, hemostatic non-absorbable sutures (for fully heparinized patients or patients with multiple arterial anastomoses), drug delivery agents, and 3-dimensional tissue engineering in vitro and in viva (h) Application in Shape Memory Alloy Actuator When it is favorable to imbue the properties of a biscrolled guest@CNT composite to a core structure, or achieve a consistent Archimedean cross-sectional topology, guest@CNT material can be helically wrapped around a core, such as a fiber or a wire. This is achieved either by directly wrapping the sheet composite around the core, or by rotating the core in order to continuously draw MWNT sheet from CNT forest.

Such a configuration is particularly useful for fuel-driven actuation of shape memory actuators (SMA), wherein catalyst powder must be confined within thermal contact of the SMA surface.

As described in Example 22, biscrolling of catalytic Pt-black@MWNT sheet around nickel-titanium alloy SMA wires allows shape memory actuation, typically driven by electric current, to be powered by high energy density fuels such as hydrogen gas or methanol vapors. The Pt-black@MWNT sheet structure is ideal for this application as it enables good fuel-catalyst interaction, while providing a thermally conductive, flexible and temperature-stable structure for platinum black confinement.

EXAMPLE 1

Figure 5:
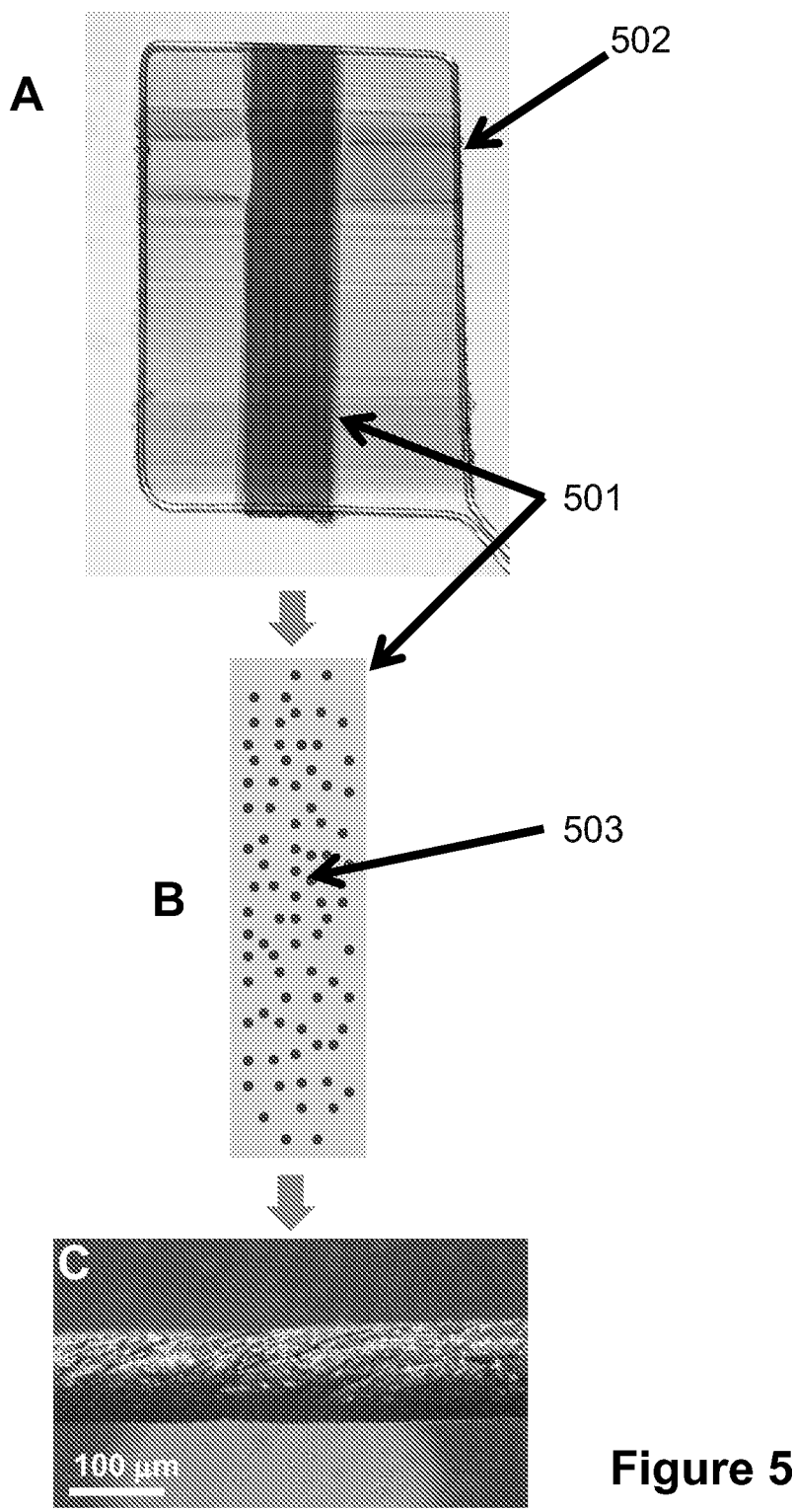
FIGS. 5A-5C illustrate the process of solution deposition: (5A) an image of free-standing MWNT sheet stack 501 on a wireframe 502; (5B) an illustration of deposited guest material 503 on MWNT sheet stack, and (5C) an optical image of a biscrolled MWNT yarn obtained by biscrolling the MWNT/guest stack of (5B).

This Example 1 demonstrates the biscrolling process using solution deposition of guest MWNTs on host CNT sheets that are orthogonal. Though the sheets comprise MWNTs, the sheet nanofibers of the host are called CNTs in this example in order to avoid confusion with the solution deposited guest MWNTs. As illustrated in FIG. 5A, to prepare the free-standing CNT sheet stack, CNT sheets 501 were placed onto a wireframe 502. To prevent collapse of the sheets during solution deposition of MWNT suspension, two layers of the host CNT sheets were placed in the orthogonal direction relative to other layers of host sheets. Suspension of MWNT powder was prepared in ethanol and then deposited onto CNT sheet stack using a pipette. FIG. 5B illustrates the deposited MWNT powder 503 on the CNT sheet stack. After evaporating the solvent, a thin layer of the guest MWNTs was formed on the host CNT sheet stack.

To increase the thickness of the guest MWNT layer, several layers of guest MWNTs were deposited. Solvent was evaporated before solution casting the next layer. After the solution deposition, a bilayer ribbon of MWNT guest and CNT sheet host was formed. To form the fiber, the ribbon was scrolled along the long sheet axis and twisted into a fiber, as shown in FIG. 5C. The MWNT guest powder weight percentage in the biscrolled fiber was more than 90 wt %, and the fiber is mechanically robust.

EXAMPLE 2

Figure 6:
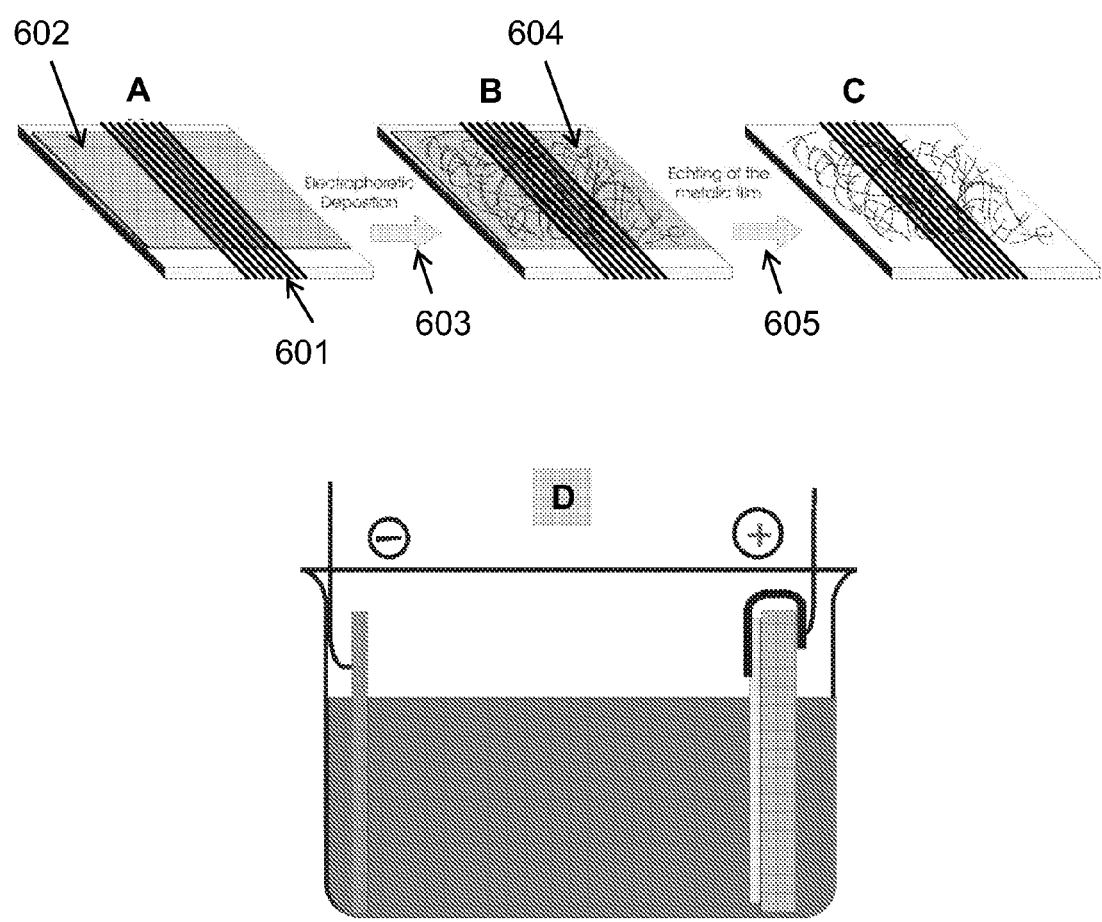
FIGS. 6A-6D schematically illustrate the process of electrophoretic deposition to produce a guest/host stack: (6A) a MWNT sheet or sheet stack 601 placed on a metallic layer 602, such as Al or Ti deposited by e-beam evaporation; (6B) electrophoretic deposition 603 of nanotubes 604 onto the MWNT sheet host and, in the case of an aluminium metallic layer, oxidation of the metallic layer; (6C) etching 605 of the metallic film (necessary when titanium is used as the metallic coating); and (6D) a schematic illustration of the electrophoretic deposition setup.

This Example 2 describes the biscrolling process using electrophoretic deposition (EPD), which can deposit a large variety of guest materials onto the solid-state-spun CNT sheets. FIG. 6 schematically illustrates such a process of electrophoretic deposition. Although the deposition of nanoparticles over metals through electrophoresis has already been studied [R. Krupke et al., *Adv. Mater.* 18, 1468 (2006); A. K. Pal et al., *Thin Solid Films* 476, 288-294 (2005); P. Poulin et al., *Carbon* 40 1741-1749 (2002); S. K. Kim et al., *J. Nanosci. Nanotechnol.* 6, 3614-3618 (2006); and A. R. Boccaccini et al., *Carbon* 44, 3149-3160 (2006)], it is believed that this is the first demonstration of electrodeposition of nanoscale material onto CNT sheets.

Utilizing the mechanical strength of the sheet, this process makes possible the fabrication of free-standing sheets or ribbons mostly consisting of nanoparticles that cannot be easily assembled into yarns. The technology also enables a continuous process of producing such yarns incorporating nanoparticles.

Substrates of borosilicate glass and poly(ethylene terephthalate) were coated with a 50-nm layer of aluminium or titanium by e-beam deposition. As illustrated in FIG. 6A, one or several forest-drawn MWNT sheets 601 were then deposited onto the glass substrate with metal coating 602. The MWNT-sheet-coated substrate was used as the positive electrode for the deposition of guest SWNTs 604 by electrophoresis. An electric field of 25 V/cm was used. Purified HiPco single-walled SWNTs (from Carbon Nanotechnologies, Inc., Houston) were dispersed in an aqueous solution using two approaches: (a) dispersing the SWNTs in a 0.1% sodium dodecyl sulphate (SDS) water solution; or (b) by functionalizing the SWNTs with $HNO_3/H_2SO_4$ (1:3) acid mixture to introduce —COOH groups on the surface of the tubes, and then dispersing the functionalized SWNTs in water. In both approaches, a probe ultrasonicator was used for dispersing the SWNTs. An ice bath was used to keep the temperature of the dispersion below 35° C. during the sonication.

The electrophoretic deposition 603 of SWNT transparent films took only a few seconds. A layer of evaporated metal acts (together with the host MWNT sheets) as an electrode during the deposition. The coated substrate was connected to the positive electrode. Both, the SWNTs wrapped with surfactant and the SWNTs functionalized with —COOH groups acquired a negative charge in water and were attracted to the positive electrode.

During the electrophoretic process, oxygen is also generated in the positive electrode. The aluminium or titanium coating was quickly oxidized to $Al_2O_3$ or $TiO_2$ and the metallic film over the substrate became transparent. The oxidation of the metallic film also absorbed the oxygen that was produced by the electrolysis of water. Once the oxidation of the metallic layer was complete, the electrical current through the cell stabilized to a very low value, interrupting the SWNT deposition.

After deposition, the substrate with the SWNTs deposited on the MWNT sheet was removed from the electrolyte and dried. Then, the substrate was washed with a proper solvent to remove any remaining surfactant.

The MWNT sheet coated with SWNTs formed a bilayered structure and could be easily separated from the substrate by immersing the substrate in a proper solvent. After separation from the substrate, the free-standing bilayered ribbon maintained its shape in solvent, and can therefore be collected as a sheet on another substrate as shown in FIG. 7A.

Figure 7:
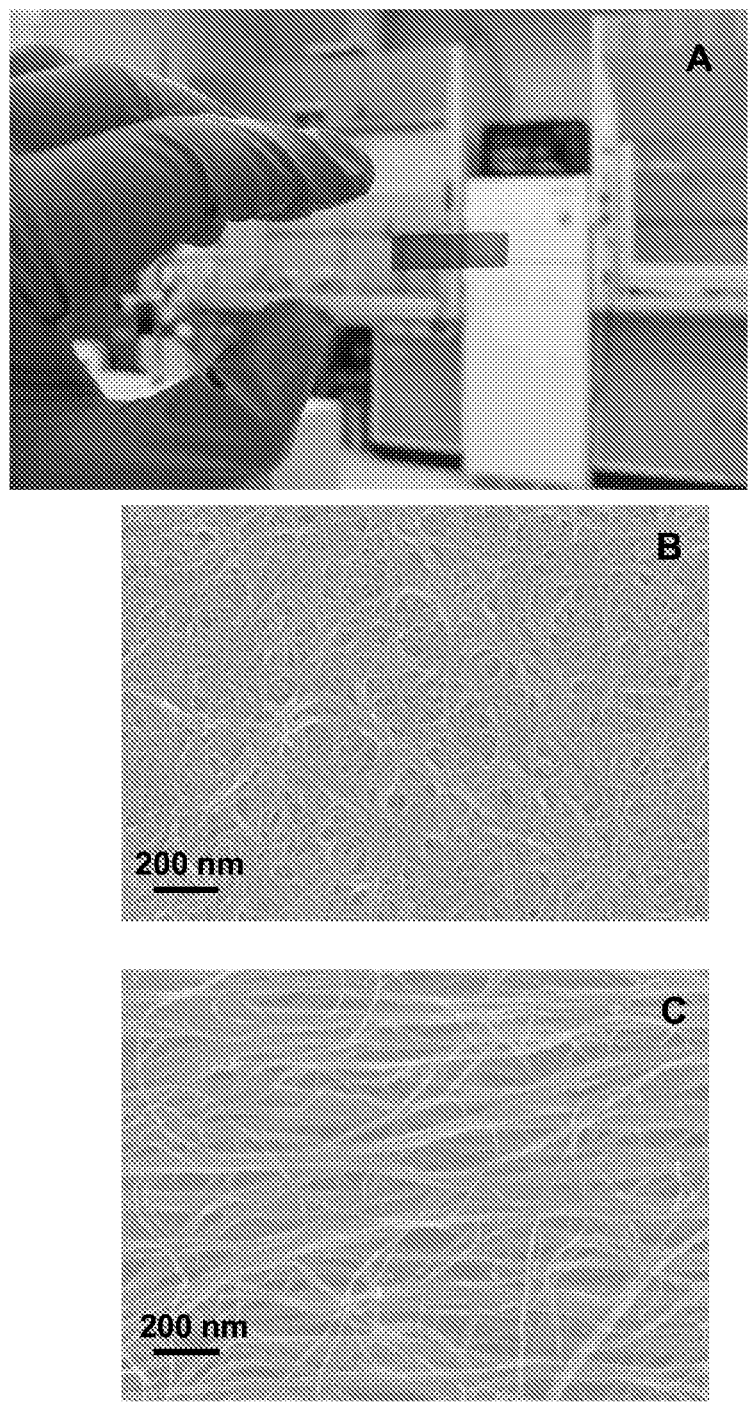
FIGS. 7A-7C show: (7A) a transparent SWNTs@MWNT bilayered stack on a glass substrate, which was made by electrophoretic deposition process; (7B) a SEM image of the SWNT layer deposited on MWNT sheet by electrophoretic deposition; (7C) a SEM image of the MWNT sheet before electrophoretic deposition.

As shown in FIG. 7B, the deposited SWNTs formed a randomly oriented network on top of the aligned MWNT sheet. The ratio of optical absorbance in the MWNT sheet-draw direction and the perpendicular direction after and before SWNT deposition are 1.04 and 2.4, respectively. This indicated that randomly oriented guest SWNT provide most of the mass of the bilayered structure.

From optical density measurement, the deposited SWNT layer accounted for 80 wt % of the total mass in the bilayered structure. The bilayered CNT sheet had an areal density of 10 $\mu g/cm^2$, as compared with 2.2 $\mu g/cm^2$ for the MWNT sheets. The specific conductivity of the SWNT/MWNT bilayered structure increased from 329 S·cm$^2$/g for the MWNT sheets (two in stack) to 1263 S·cm$^2$/g with SWNT addition, a factor of ~4.

EXAMPLE 3

This Example 3 describes the biscrolling process using filtration-based deposition. In this process, the guest material to be deposited was dispersed in a suitable liquid medium using ultrasonication. Surfactants are sometimes used as the dispersing medium apart from the most commonly used mediums viz. de-ionized water and isopropanol. The filter for filtration deposition was a stack of MWNT sheets placed on a cellulose nitrate filtration membrane (Whatman, pore size was 0.45 μm, approximate thickness of 120 micrometers). Multiple layers of the MWNT sheets, typically one to three layers, were placed on the filter membrane, and then densified by wetting with isopropanolError! Reference source not found. The suspension of the guest material was then deposited onto the MWNT sheets/membrane through filtration. The filtration deposition of well dispersed suspensions formed a homogenous layer of the guest material on top of the membrane. After the filtration, the guest/MWNTsheet/filter trilayer stack was then dried. In some cases, an extra layer of MWNT sheet was applied on top of the deposited guest material in case that the guest material had poor adhesion to the MWNT sheets. After completely drying the membrane, strips of the membrane were cut along the length of the MWNT sheets for yarn spinning as described in Example 11.

Figure 8:
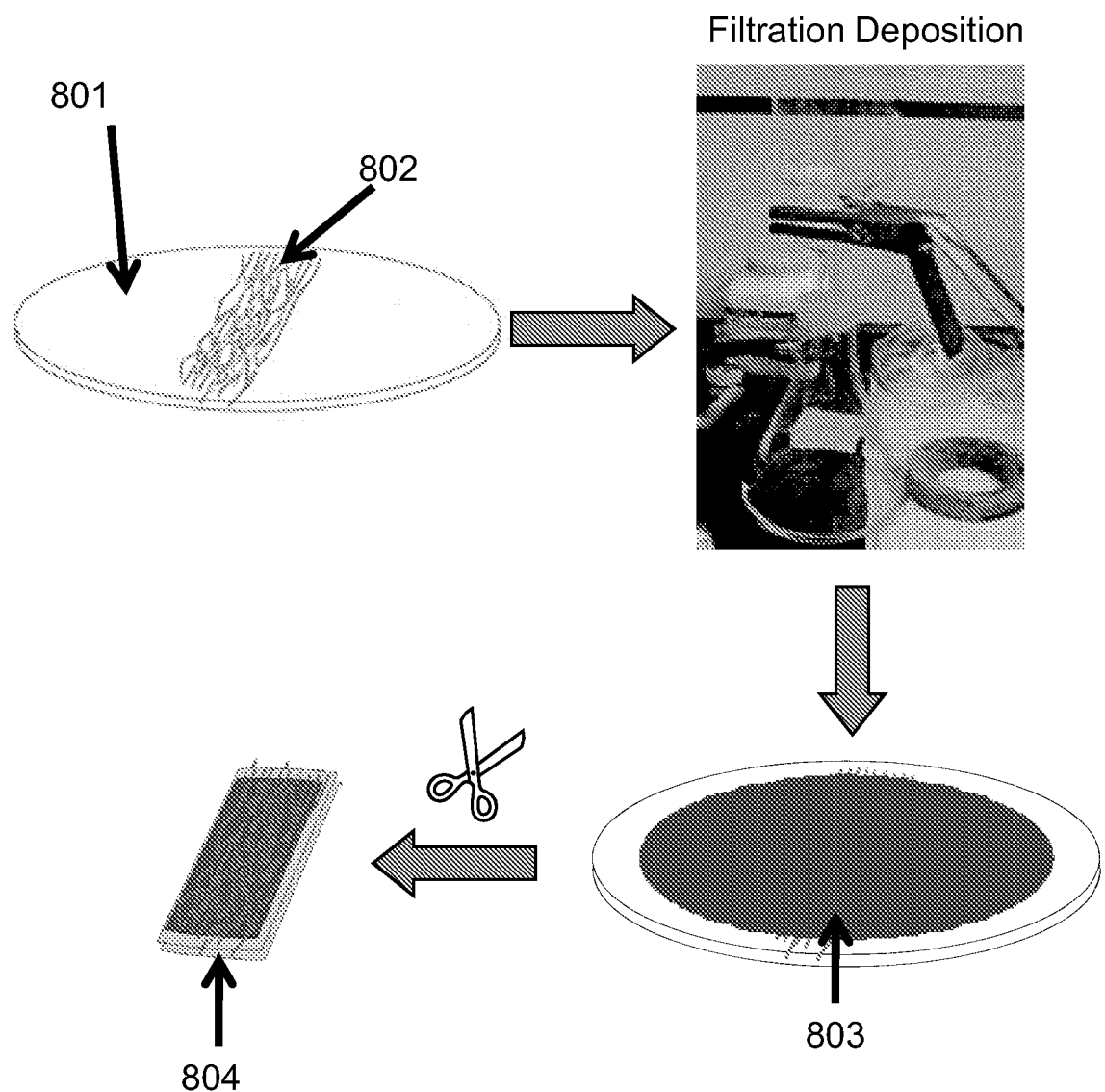
FIG. 8 schematically illustrates the process of filtration deposition of guest, which includes placing two to three layers of MWNT sheets 802 onto a cellulose nitrate filter membrane 801, filtration-based deposition of the liquid-dispersed guest material onto the sheet/membrane filter, drying the guest/host/filter stack 803, and then cutting the filter with attached guest/host stack into a strip for biscrolling 804.

The biscrolling process of filtration-deposition is illustrated in FIG. 8.

1. Two to three layers of solid-state spun MWNT aerogel sheet 802 were placed onto a cellulose nitrate filter membrane 801.
2. Dispersed solid solution was then filtered through sheet/filter membrane conferring powder onto MWNT sheet platform in a layer of generally consistent thickness.
3. The powder/MWNTsheet/filter tri-layer stack 803 was then dried and manually cut into a 5-10 mm×47 mm piece 804.

Figure 9:
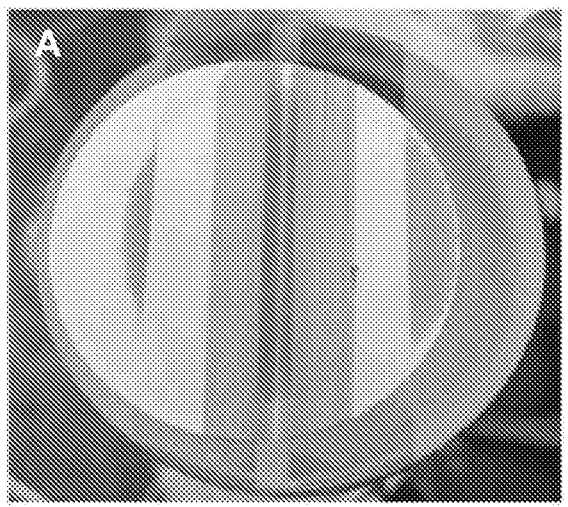
FIGS. 9A-9B show: (9A) the formation of strip pattern of $TiO_2$ guest material on MWNT sheet stack; and (9B) a cross-section of the biscrolled yarn spun from the patterned strip of (9A).
Figure 9:
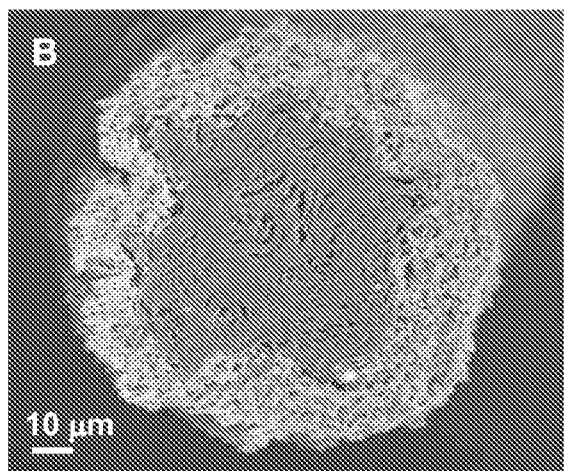
Figure 10:
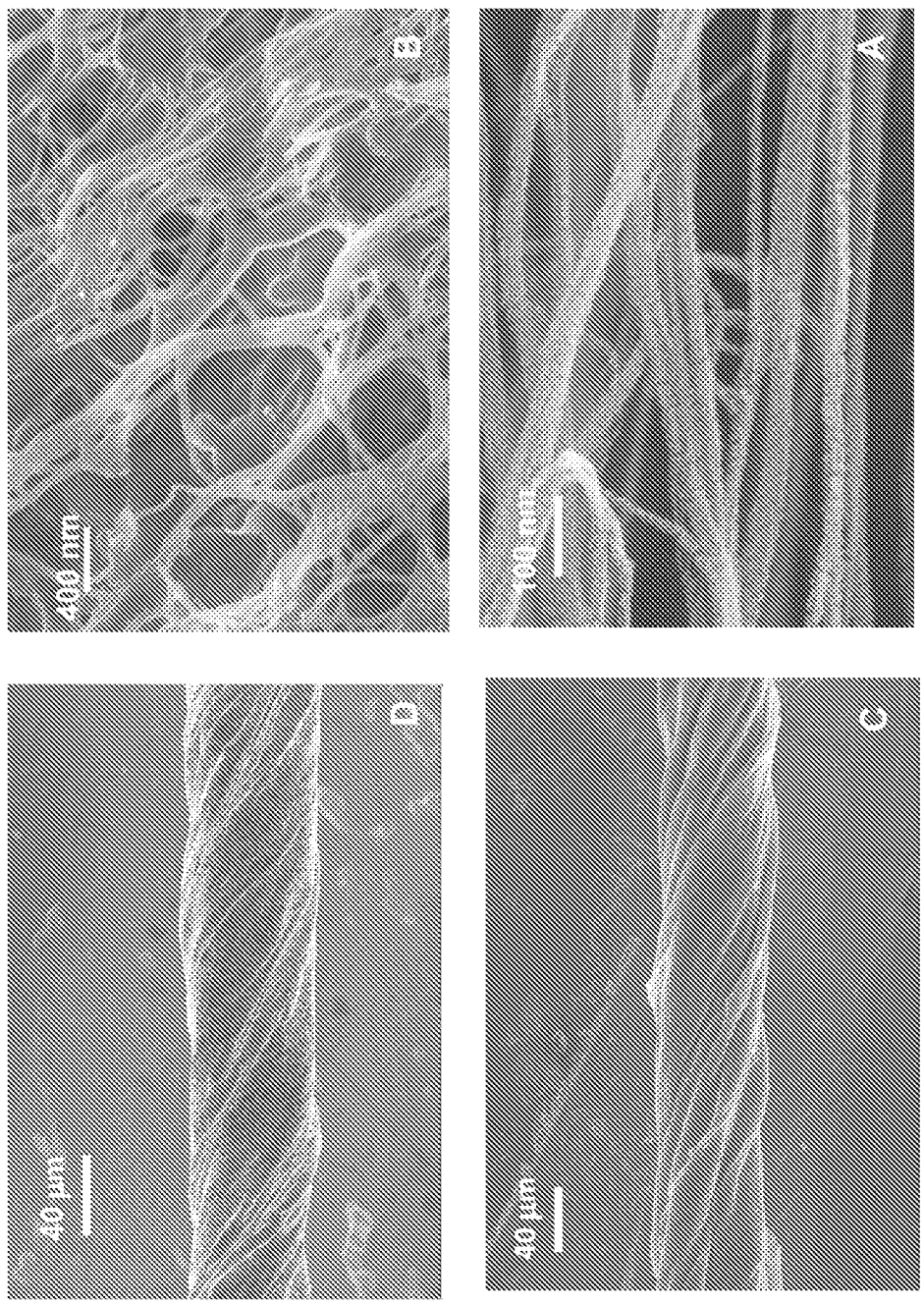
FIGS. 10A-10D show SEM images: (10A) a MWNT sheet coated with platinum by electron beam evaporation (EBE); (10B) a MWNT sheet coated with 25-nm thick titanium by EBE; (10C) an $Al_2O_3$@MWNT biscrolled yarn made by EBE deposition; and (10D) an aluminum@MWNT biscrolled yarn prepared using EBE to produce the guest/host stack.

A modified filtration method was developed to deposit the guest material with strip pattern on the MWNT sheets. Strips of Kapton tape were affixed on the frit of Erlenmeyer flask. As described above, layers of MWNT sheets were placed on the cellulose nitrate membrane. The membrane was then placed on top of the frit in such a way that the tape strips below the membrane blocked the vacuum in desired areas of the membrane. The suspension was deposited onto the area that was open to the vacuum. This led to the formation of a strip pattern of the guest material on the CNT sheet stack. FIG. 9A shows this formation of strip pattern of $TiO_2$ guest material on MWNT sheet stack. FIG. 9B shows the cross-section of the biscrolled yarn spun from the patterned strip of FIG. 9A into an Archimedean scroll. The darker inner area is MWNTs and lighter outer area is $TiO_2$/MWNTs.

EXAMPLE 4

This Example 4 demonstrates the biscrolling process using electron beam evaporation (EBE) of guest, which can deposit a large variety of metals and ceramics onto the solid-state-spun CNT sheets. In this example, deposition of Ti, Cu, Al, $Al_2O_3$, and Pt onto CNT sheets was demonstrated. FIGS. 10A-10D show SEM images of these depositions and biscrolled yarns.

For EBE deposition, one or several CNT sheets (either free standing or placed over cellulose nitrate membrane) of different shapes were prepared. The thicknesses of the EBE-deposited layers of titanium (Ti), copper (Cu), aluminum (Al) and aluminum oxide ($Al_2O_3$) ranged from 1 to 25 nm. The coated sheet stack on cellulose nitrate membranes were then submerged in acetone ($CH_3COCH_3$) that dissolved the cellulose nitrate membrane. Alternatively, any other proper solvent that dissolves the cellulose nitrate membrane could be used.

One end of the stack was attached to a ferromagnetic wire rod while the other end was attached to thin metal rod crossbar. The stack was then suspended by the crossbar into a beaker of acetone until the cellulose nitrate filter membrane completely dissolved and only the powder/MWNT sheet stack remained. Twist was then initiated via a magnetic stirrer plate until the biscrolled yarn reached uniform diameter. The resulting biscrolled yarn was then washed with deionized water and allowed to air-dry.

EXAMPLE 5

This Example 5 demonstrates biscrolling process to continuously produce biscrolled yarns of SWNTs deposited by air spray process onto forest-drawn MWNT sheets.

Suspension of SWNTs dispersed in methanol, acetone, or any other compatible solvents was sprayed using an air-gun onto the free-standing MWNT sheet (or ribbon or wedge) that was continuously drawn from the forest. The MWNT sheet can be heated during the spraying process in order to aid the evaporation of the solvent used for the SWNT suspension. The bilayered SWNTs@MWNT ribbon can be simultaneously twisted into biscrolled yarn.

EXAMPLE 6

This Example 6 demonstrates yarn formation using plasma enhanced chemical vapor deposition (PECVD), which can deposit a large variety of materials onto the solid-state-spun CNT sheets. In this Example 6, deposition of $SiO_2$ and $Si_3N_4$ onto CNT sheets was demonstrated.

Figure 11:
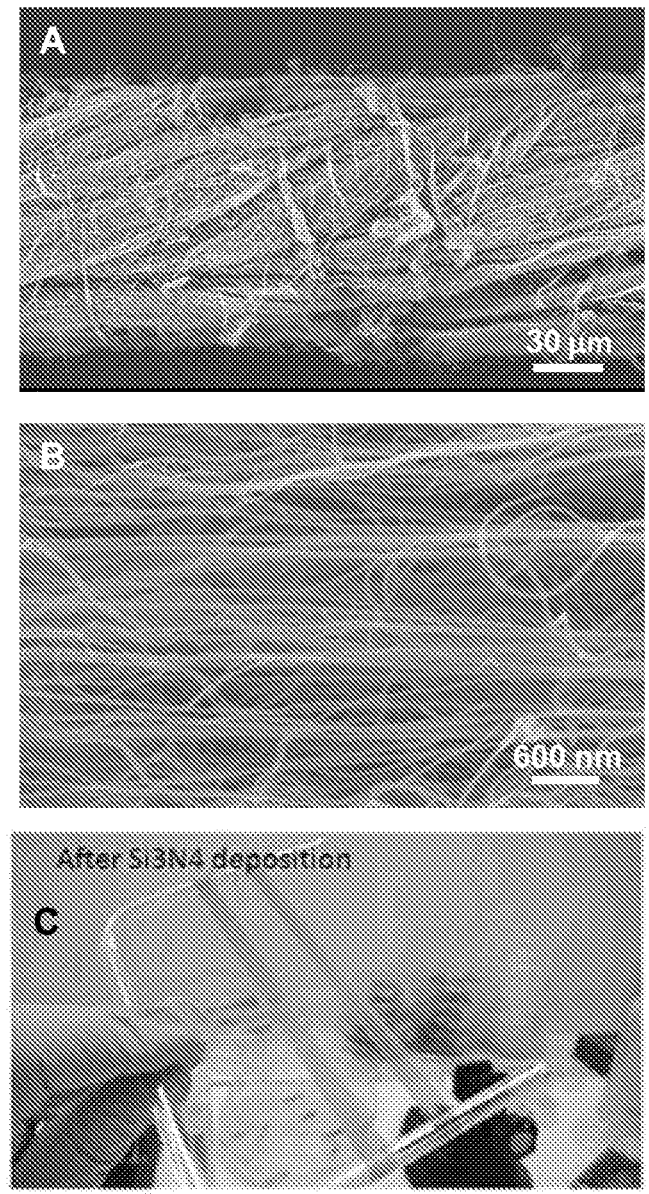
FIGS. 11A-11C show: (11A) a SEM image of a $SiO_2$/MWNT composite yarn made by a plasma enhanced chemical vapor deposition (PECVD) process; (11B) a SEM image of a MWNT sheet coated with $Si_3N_4$ prepared by the PECVD process; and (11C) an image of a MWNT sheet coated with $Si_3N_4$ by PECVD, which is suspended between two end supports.

For $SiO_2$ deposition by PECVD, one or several free-standing CNT sheets were heated up to 200° C. in inert atmosphere in the plasma reactor chamber, and then exposed to plasma generated by using RF power in the presence of a mixture of silane ($SiH_4$) and nitrous oxide ($N_2O$). This procedure generated a homogenous amorphous $SiO_2$ coating around individual nanotubes and individual nanotube bundles. After the plasma deposition, the $SiO_2$/CNT sheets were placed over cellulose nitrate membrane and twisted into yarn as described in Example 11. See FIG. 11A, which is a SEM image of a $SiO_2$/MWNT yarn made by a PECVD process. This yarn is not biscrolled, since the guest is uniformly deposited on the host sheet.

For $Si_3N_4$ deposition by PECVD, one or several free-standing CNT sheets were heated up to 250° C. in $N_2$ inert atmosphere in the plasma reactor chamber, and then applied to plasma using RF power in the presence of a mixture of silane ($SiH_4$) and ammonia ($NH_3$). This procedure generated a homogenous $Si_3N_4$ coating around individual nanotubes and individual nanotube bundles. See FIG. 11B, which is a SEM image of a MWNT sheet coated with $Si_3N_4$ prepared by the PECVD process; and FIG. 11C, which is an image of a MWNT sheet coated with $Si_3N_4$ by the PECVD suspended between two end supports. After the plasma deposition, the $Si_3N_4$ coated CNT sheets were placed over cellulose nitrate membrane and twisted yarn as described in Example 11.

EXAMPLE 7

This Example 7 demonstrates the biscrolling process using guest deposition by ink jet printing. Using conventional ink jet printing technology, suspended powder material serves as a "printing ink" that can be continuously deposited as guest onto an aerogel single-layer MWNT sheet prior to or during twist insertion to produce biscrolled yarn. Since the free-standing CNT aerogel has very low areal and volumetric density it is easily damaged. Hence, ink jet printing provides an excellent way of depositing material onto the spinning wedge without disrupting the spinning process. Patterning of the deposited layer is also possible using this technology. In this demonstration, a Canon Ip 1800 Standard Ink-Jet Printer was modified as follows:

1. The outer cover and paper feeding apparatus were fully removed from printer.
2. The ink jet ink reservoir cartridge was disassembled manually to fully remove existing ink.
3. The ink jet reservoir cartridge was then filled with same suspended powder solutions as was used for the filtration-based deposition method but at a higher concentration of 10 wt % powder in 1% aqueous SDS (sodium dodecyl sulfate) and re-assembled.
4. The Cartridge was then re-introduced into the ink jet printer.

Figure 12:
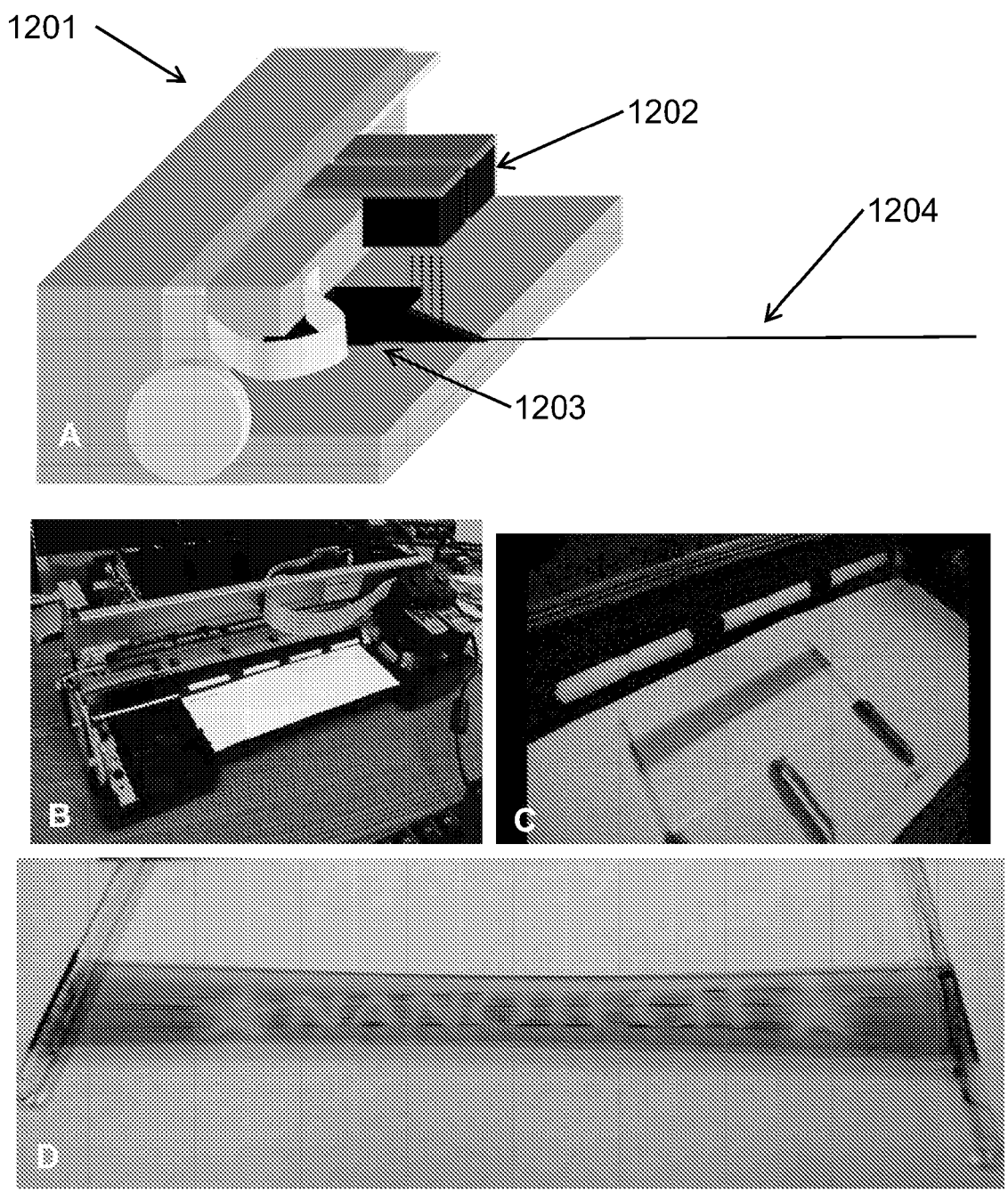
FIGS. 12A-12D show the process of guest deposition by ink jet printing: (12A) a schematic illustration of ink jet printer 1201 (having a modified printer cartridge 1202 filled with a powder dispersion) in which the printer can perform the process of ink jet deposition onto a web formation area 1203 while simultaneous spinning is used to provide the spun material 1204; (12B) a picture of the modified ink jet printer 1201; (12C) a MWNT sheet ribbon mounted on a U-frame for printing; and (12D) a printed pattern of TiO$_2$ guest material on MWNT sheet.

FIG. 12A is a schematic illustration of the ink jet printer 1201 (having the modified printer cartridge 1202 as described above). FIG. 12B is a picture of the modified ink jet printer 1201.

For ink jet deposition onto MWNT sheet, a MWNT sheet ~11 cm long by 3 cm wide was suspended between two end supports comprised of 2 fixed position glass rods attached to a common base. FIG. 12C shows a MWNT sheet ribbon mounted on a U-frame for printing. The sheet assembly was then placed under the targeted ink jet position. Ink jet printing was then initiated with a calculated droplet size of ~3 picoliters/droplet. The printed pattern of $TiO_2$ is shown in FIG. 12D. FIG. 12A further shows a schematic diagram for continuous deposition onto aerogel CNT sheet 1203 during standard fiber spinning process to provide the biscrolled yarn 1204.

EXAMPLE 8

Figure 13:
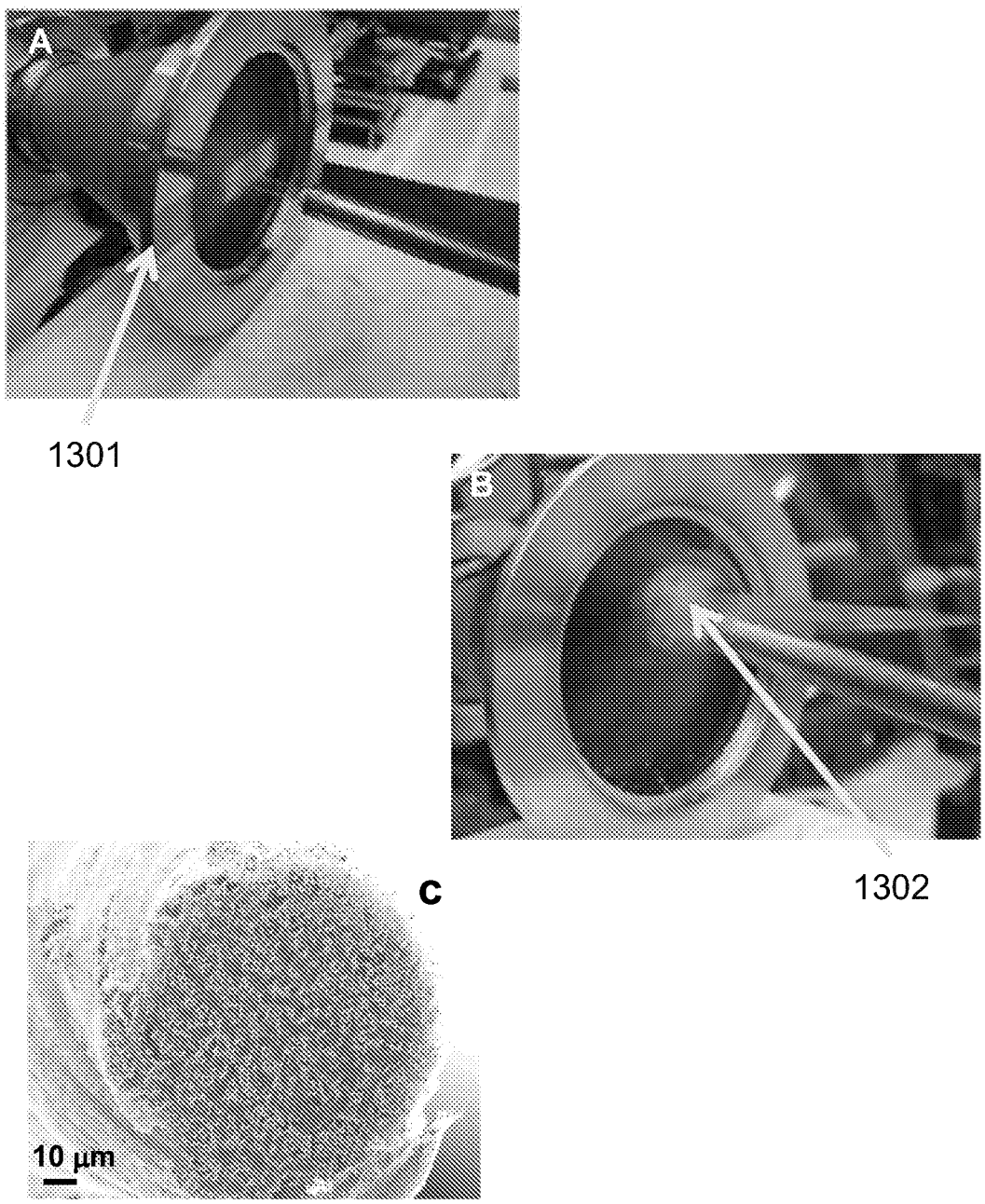
FIGS. 13A-13C show a process in which guest is deposited from an aerosol: (13A) and (13B) show a continuous deposition of TiO$_2$ aerosol 1302 onto MWNT sheet 1301; and (13C) a cross-section of the biscrolled TiO$_2$ yarn showing uniform distribution of the deposited material.

This Example 8 demonstrates the biscrolling process using aerosol-based deposition of the guest, where the aerosol was produced by gas phase reaction immediately prior to deposition on a MWNT host. In this approach, multiple layers of nondensified CNT sheets were placed on a quartz frame that was then placed close to a hot plate to avoid densification during the deposition process. The guest material deposited on these sheets was in the aerosol phase. FIGS. 13A-13B show the deposition of titanium dioxide ($TiO_2$) in the aerosol phase 1302 on a MWNT sheet 1301. This aerosol was produced by the hydrolysis of titanium tetrachloride ($TiCl_4$). $TiCl_4$ is a highly volatile metal halide which when exposed to water produces opaque clouds of $TiO_2$ and hydrogen chloride as by-products. FIG. 13C shows a SEM image of a cross section of a biscrolled $TiO_2$@MWNT yarn produced by this deposition method.

EXAMPLE 9

This Example 9 demonstrates a biscrolling process using deposition of the guest on a MWNT sheet stack using an airbrush. In conventional use, the airbrush is used as a mini-sandblaster and/or an etching tool. In the present application the airbrush delivers a dry guest powder to a host MWNT sheet, for the purpose of forming bilayer sheet strip stacks used for biscrolling. A Paasche brand airbrush AEC Air Eraser (steel tip with carbide insert) was used, together with a X-Air Compressor with regulator (Model #80-8, operated at ~6-8 psi). The particulate size of deposited guest materials ranged from 0.1 to 10 μm in diameter, depending upon the specific guest material.

EXAMPLE 10

This Example 10 demonstrates the biscrolling process using electrostatic deposition of guest nano/micro particles onto the nanotube web (i.e., a sheet or sheet wedge) from a carrier gas (conventionally air or nitrogen) using a conventional electrostatic powder gun. A commercially available powder coating gun was used wherein the particles were charged with 15 KV DC and 15 μA. Controlling the distance between gun tip and the target web (as well as the carrier gas pressure) can be used to provide desired deposition conditions.

Figure 14:
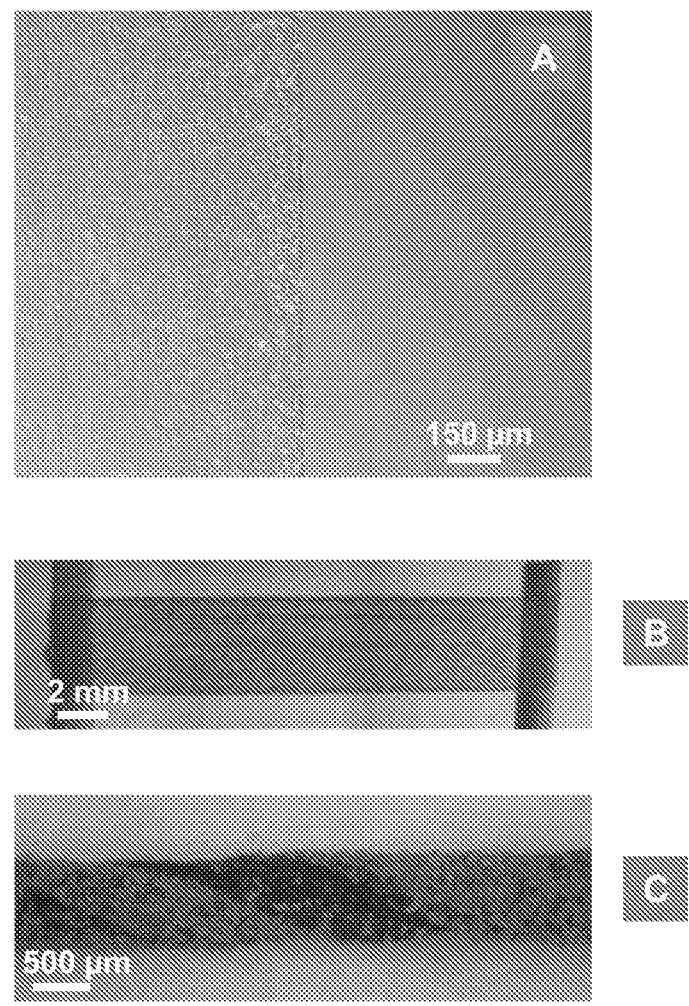
FIGS. 14A-14C show a process for the electrostatic deposition of guest: (14A) TiO$_2$ deposited on MWNT sheets using electrostatic deposition; (14B) red pigment deposited on MWNT sheet stack using electrostatic deposition; and (14C) biscrolled yarn of the pigment of (14B).

FIG. 14A shows $TiO_2$ guest particles deposited on a MWNT host sheet using electrostatic deposition. FIG. 14B shows red pigments deposited on MWNT sheet stack using electrostatic deposition. FIG. 14C shows biscrolled yarn of the pigment of FIG. 14B. This biscrolled yarn was made by twist of the rectangular bilayered sheet strip in FIG. 14B, which resulted in a double Archimedean scroll. For one of these scrolls the red pigment is exterior to the MWNT scroll surface and for the other scroll the red pigment is exterior to the MWNT scroll (though in both cases the red pigment is volumetrically included in the corridors of the scrolls). Wrapping these two scrolls together in the final stage of twist-based yarn spinning creates the barber pole effect seen in FIG. 14C.

This approach was fast and controllable—attraction between charged guest particles and the grounded or oppositely charged target web helped create a uniformly deposited layer of guest particles over the deposition area. Highly charged particles repulsed each other, aiding de-agglomeration and eventually providing a well dispersed particles layer on the nanotube sheet surface.

EXAMPLE 11

Figure 15:
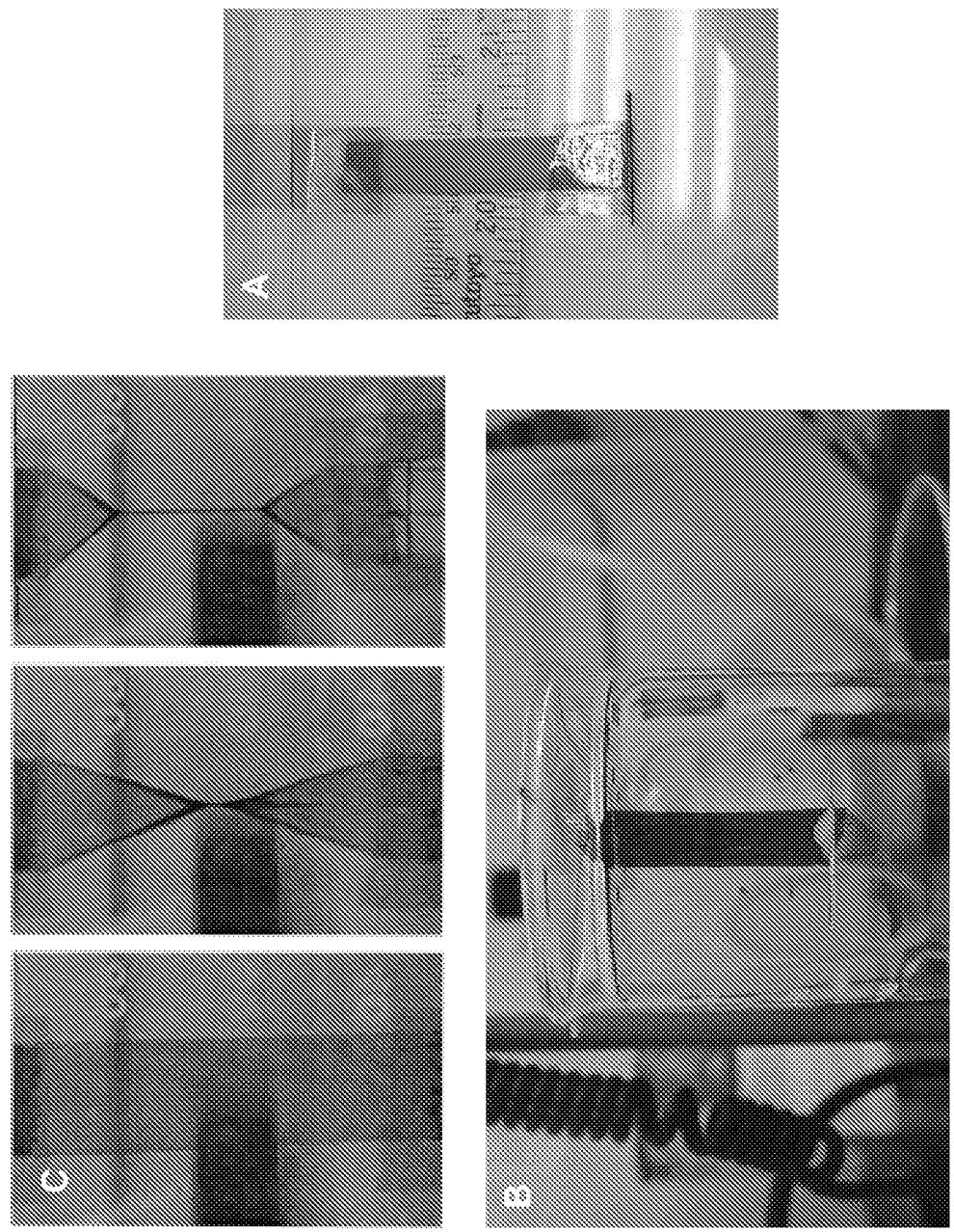
FIGS. 15A-15C show the process of twist insertion in liquid: (15A) a ribbon of guest/MWNT sheet/filter stack attached to an iron wire rod at one end; (15B) the tri-layered ribbon suspended by the crossbar into a 250 mL beaker of acetone; and (15C) images of converting the ribbon into yarn by twisting using a magnetic stirrer.

This Example 11 demonstrates converting a rectangular bilayered ribbon into biscrolled yarn by twisting in liquid. As shown in the FIG. 15A, a steel wire rod was attached to one end of the bilayered ribbon using epoxy glue and the opposite end was attached to Kapton tape as an end support. The bilayered ribbon stack was then suspended in liquid (250 mL beaker of acetone), as shown in FIG. 15B, and the filter membrane was dissolved by the solvent.

For cellulose nitrate membrane filters, the dissolution of the filtration membrane usually took about 1 to about 5 minutes in acetone. The beaker was then placed onto a magnetic stirrer. Using magnetic force between the stirrer and the steel rod attached to the bilayered ribbon, twist was introduced, converting the ribbon into a biscrolled yarn, as shown in the images of FIG. 15C.

This method allowed controlling of twist speed without applying large axial stress to the CNT sheet. As the sheet was twisted into a yarn, it got shorter. After the desired number of twists was applied to the CNT ribbon with the guest material, the process was stopped and the yarn was removed from the acetone bath. To assure the complete removal of the membrane, the biscrolled yarn was immersed in a fresh acetone bath for another 30 minutes.

EXAMPLE 12

This Example 12 demonstrates producing superconducting yarn of $MgB_2$@MWNT using the biscrolling method. Superconducting yarns were produced by depositing a layer of $MgB_2$ precursors on the CNT sheet. The Mg and B powders (Alfa Aesar) were uniformly dispersed in isopropanol by ultrasonication and then were deposited onto MWNT sheet using filtration deposition described in Example 3.

Figure 16:
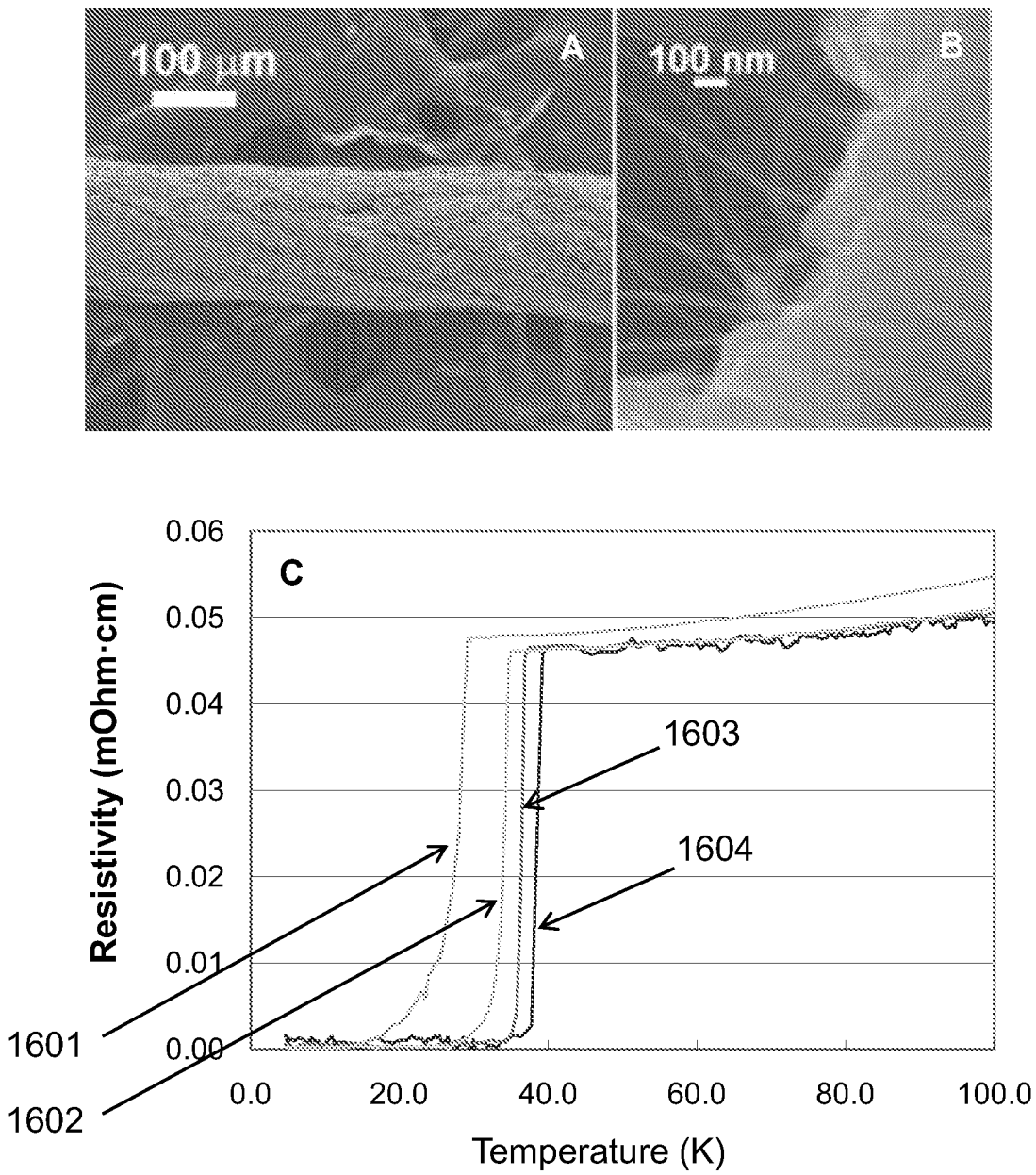
FIGS. 16A-16C show: (16A) a SEM image of a biscrolled MgB$_2$@MWNT yarn; (16B) a SEM image of the fracture surface of the yarn of (16A); and (16C) a graph plotting resistivity versus temperature for the biscrolled MgB$_2$ yarn recorded for different applied electrical current (curves 1601-1604).

The $MgB_2$@MWNT ribbon was twisted into a biscrolled yarn, as described in Example 11. The CNT sheet was robust enough to hold Mg and B powders producing yarns that contain 99 wt % of Mg and B powder. After twisting, the yarn was sintered at 750° C. for 30 min in an argon atmosphere with excess of Mg vapor, so that magnesium and boron reacts forming the $MgB_2$ superconductive phase. FIG. 16A is a SEM image of the biscrolled $MgB_2$@MWNT yarn. FIG. 16B is a SEM image of the fracture surface of the yarn of FIG. 16A.

For DC electrical measurements, the yarn sample was mounted to a four-point probe fixture using silver paint (Dotite D-550). The temperature dependence of yarn electrical resistance was recorded in the temperature range from about 4.2K to about 300K using a home-made test probe. Resistance values were measured with a Keithley 2602 Sourcemeter. The superconducting transition of the electrical resistance is shown in FIG. 16C. FIG. 16C is a graph plotting resistivity versus temperature for the biscrolled $MgB_2$@MWNT yarn for different values of electrical current. These electrical current values in FIG. 16C are 50 mA (1604), 100 mA (1603), 200 mA (1602), and 400 mA (1601), respectively. The onset of the sharp superconducting transition observed at I=50 mA was about 39 K. The onset shifts to lower temperatures with increasing measurement current.

EXAMPLE 13

This Example 13 demonstrates making biscrolled graphene nanoribbon yarns for energy storage and other applications. These results are obtained by biscrolling graphene nanoribbon guest (or the precursor graphene oxide nanoribbons) in a MWNT sheet host by using filtration-based deposition of these guests on MWNT sheets.

First, graphene nanoribbons were obtained by cutting about 300 μm long MWNTs along their longitudinal axes. These MWNTS were obtained by chemical vapor deposition of acetylene gas on top of a catalytic bed of iron nanoparticles (<10 nm). [See Zhang 2005, at 1215-1219].

The cutting process (unzipping) was chemically driven by an oxidizing system consisting of $KMnO_4$ and $H_2SO_4$ at the temperature of 55-70° C. [D. V. Kosinkyn et al., *Nature* 458, 872-877 (2009)]. Between 800 and 900 weight percent of oxidant, $KMnO_4$, with respect to the initial amount of carbon nanotubes, was optimum for unzipping the long, narrow MWNTs produced by the inventors (diameters 5-15 nm, 6-12 walls and lengths of about 300 μm) and used in this Example 13. For much higher content of $KMnO_4$, the MWNT were totally dissolved because of the extremely oxidative conditions.

Figure 17:
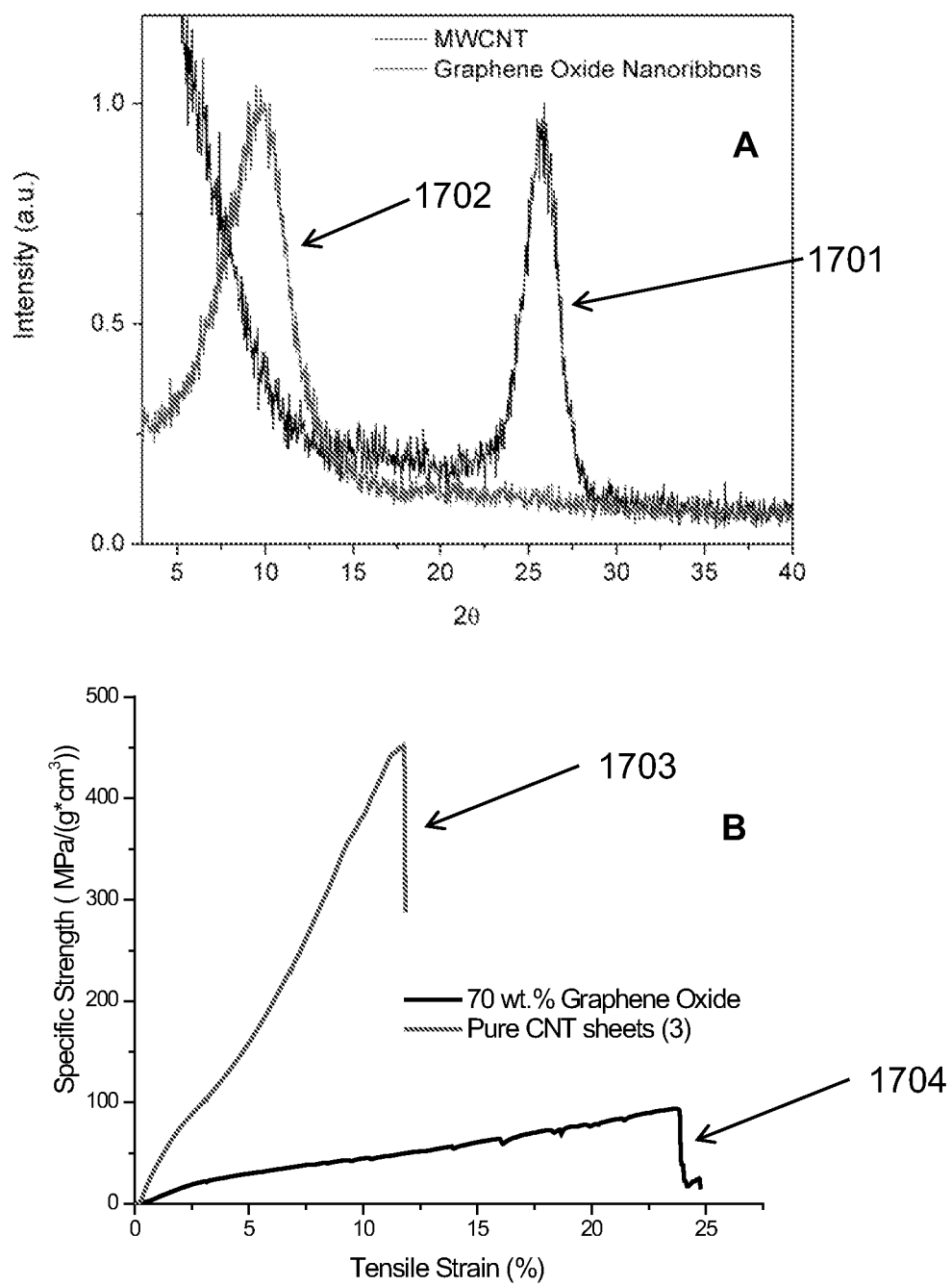
FIGS. 17A-17B show: (17A) a graph illustrating X-ray diffraction of the original MWNT material (curve 1701) and the graphene oxide nanoribbons (curve 1702); and (17B) a graph plotting specific stress versus strain curves for the twist-spun MWNT yarn (curve 1703) and biscrolled graphene oxide nanoribbon yarn (curve 1704) (with 70 wt. % graphene oxide nanoribbons and three layers of MWNT sheets).

Powder x-ray diffraction data were collected on a Rigaku Ultima-III diffractometer using Cu—$K_\alpha$ radiation ($\lambda$=1.5418 Å). FIG. 17A shows the X-ray diffraction spectra of the original MWNT material (curve 1701) and the graphene oxide nanoribbons (curve 1702). The samples oxidized with 850 wt % of $KMnO_4$ did not show the diffraction peak corresponding to the carbon nanotube inter-wall distance, 3.4 Å, but a new peak emerged at $2\Theta$=9.7° corresponding to a d spacing of 9.1 Å, the (002) reflection of intercalated graphene oxide nanoribbons.

Biscrolled graphene nanoribbons yarns were first prepared by chemical and thermal treatment of the graphene oxide nanofibers before being incorporated as a guest into the MWNT host.

For the chemical reduction of graphene oxide nanoribbons, hydrazine monohydrate (1 μL/3 mg graphene oxide nanoribbons) was used (12 h at 80° C. in DMF). The graphene oxide nanoribbons were thermally reduced by employing two different conditions.

In one case a "soft" thermal treatment was applied (annealing in argon gas at 150° C. for two hours) and in another case more extreme thermal reducing treatment was applied at 800° C. (annealing in argon:hydrogen (95:5) for 5 hours). After either of those treatments, the basal distance between sheet layers returns to ~3.4 Å.

Strong, multifunctional biscrolled graphene oxide nanoribbons@MWNT yarns and biscrolled graphene nanoribbon@MWNT yarns were prepared by filtration method (Example 3) and twisted in liquid medium (Example 11). An aqueous solution (10 mg/liter) of graphene oxide nanoribbons or reduced graphene oxide nanoribbons dispersed in 1 wt % SDS was prepared by probe sonication. After biscrolling and drying, usually more than 90 wt. % in the composite fiber was graphene or graphene oxide nanoribbons.

FIG. 17B shows specific stress versus strain curves for the twist-spun MWNT yarn (curve 1703) and biscrolled graphene oxide nanoribbon yarn (curve 1704) (with 70 wt. % graphene oxide nanoribbons and three layers of MWNT sheets). The biscrolled graphene oxide yarn was mechanically tough, having strengths as high as 95 MPa/(g/cm$^3$) and strains as large as 23%. The failure strain decreased when chemical and/or thermal treatments were performed to reduce the graphene oxide nanoribbons.

EXAMPLE 14

This Example 14 demonstrates making nanostructured $LiFePO_4$@MWNT biscrolled yarns for lithium battery application. Commercially available carbon-coated $LiFePO_4$ was used. Biscrolled $LiFePO_4$@MWNT yarn electrodes were prepared by a similar wet filtration method as described in Example 3, which involved ultrasonic dispersion of 2-10 mg of $LiFePO_4$ in isopropanol, filtration-based deposition of the solution dispersed $LiFePO_4$ guest on the host MWNT sheets, and then twist insertion, as described in Example 11. In the present example, the $LiFePO_4$@MWNT biscrolled yarn was subjected to a thermal treatment at 600° C. for 6 hours in argon flow. As prepared, 1 cm to 2.5 cm long cathode fibers were deployed as a whole cathode without the need of using a metal current collector along the length of the yarn.

Figure 18:
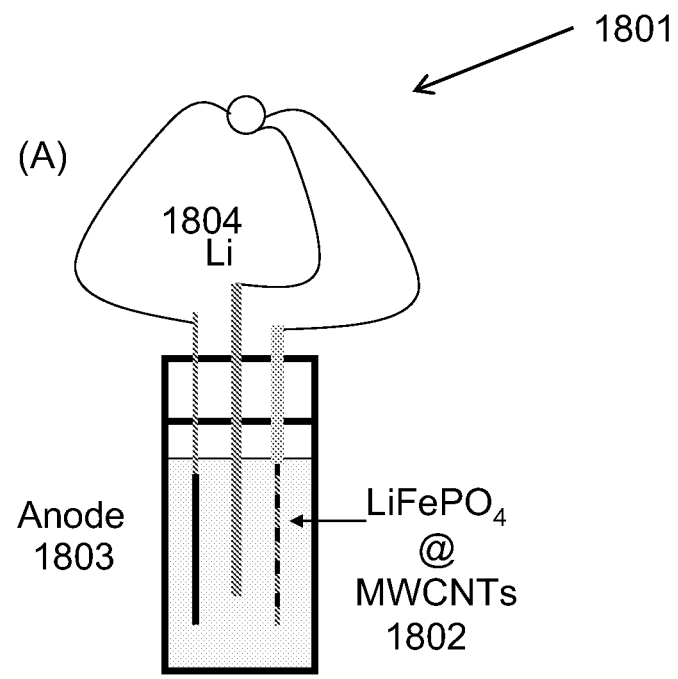
FIGS. 18A-18B show: (18A) a schematic of the glass vial cell 1801 used for electrochemical performance measurements of the biscrolled LiFePO$_4$@MWNT 1802 as cathode material; and (18B) a cyclic voltammogram of the biscrolled LiFePO$_4$ yarn at 0.1 mV/s in the 2.5-4.2 volts range.
Figure 18:
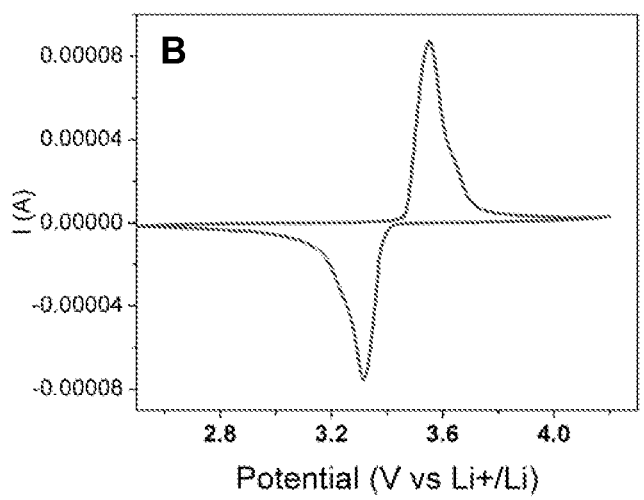

The electrochemical performance of the $LiFePO_4$ biscrolled yarns as cathode was tested inside an argon-filled glove box using a three electrode cell in a glass vial 1801, as shown in FIG. 18A. Before putting the yarns inside the glove box, the yarns were clamped on one end with wrapped aluminum foil holders and then dried for at least 30 minutes at 120° C. in air.

For testing $LiFePO_4$@MWNT yarns 1802, graphite was used as the counter electrode and lithium foil was used as the reference electrode and 1M $LiPF_6$ in ethylene carbonate:dimethyl carbonate (1:1 v/v) was used as the electrolyte. Cyclic voltammetry was carried out at a scanning rate of 0.1 mV/s between 2.5 and 4.2V (versus Li/Li$^+$). FIG. 18B shows the cyclic voltammogram. The cells were galvanostatically charged and discharged over a voltage range of 2.5-4.2 V at different rates.

Specific capacities have been calculated for the total weight of electrode. The total weight percentage of active material in the electrode including current collector is always larger than 90 wt %, versus a typical loading of 70 wt % in conventional $LiFePO_4$ electrodes.

Figure 19:
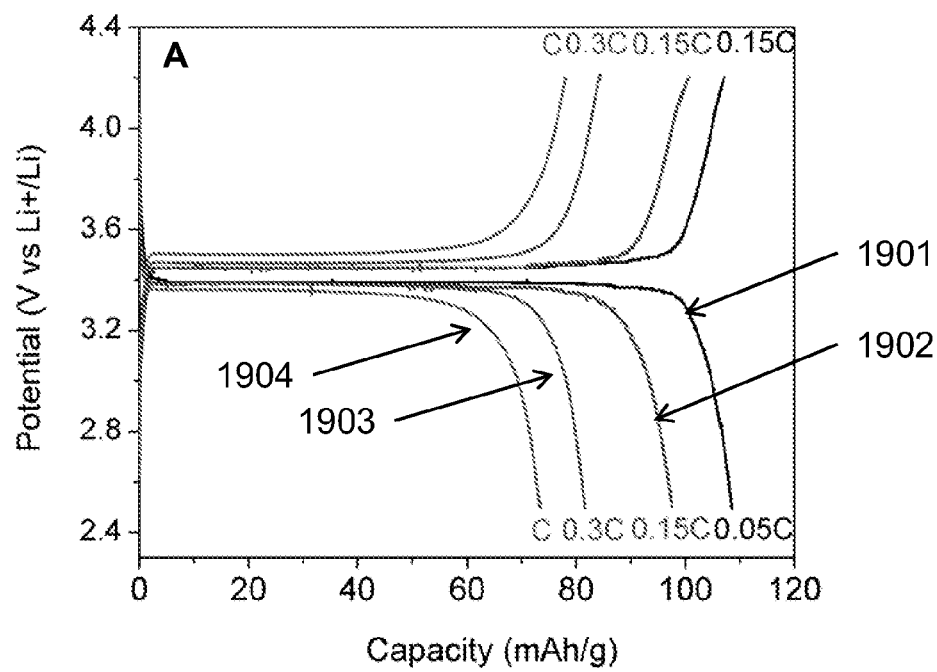
FIGS. 19A-19C show: (19A) a graph of galvanostatic charge and discharge curves (curves 1901-1904, at rates of 0.05 C, 0.15 C, 030 C, and 1.0 C, respectively) showing the voltage versus the specific capacity per total weight of electrode for the biscrolled LiFePO$_4$@MWNT yarn; (19B) a SEM image of the biscrolled LiFePO$_4$@MWNT yarn showing a homogeneous diameter along the length, and (C) a high magnification SEM of the biscrolled LiFePO$_4$@MWNT yarn showing good contact between the CNT network and the active LiFePO$_4$ nanoparticles.
Figure 19:
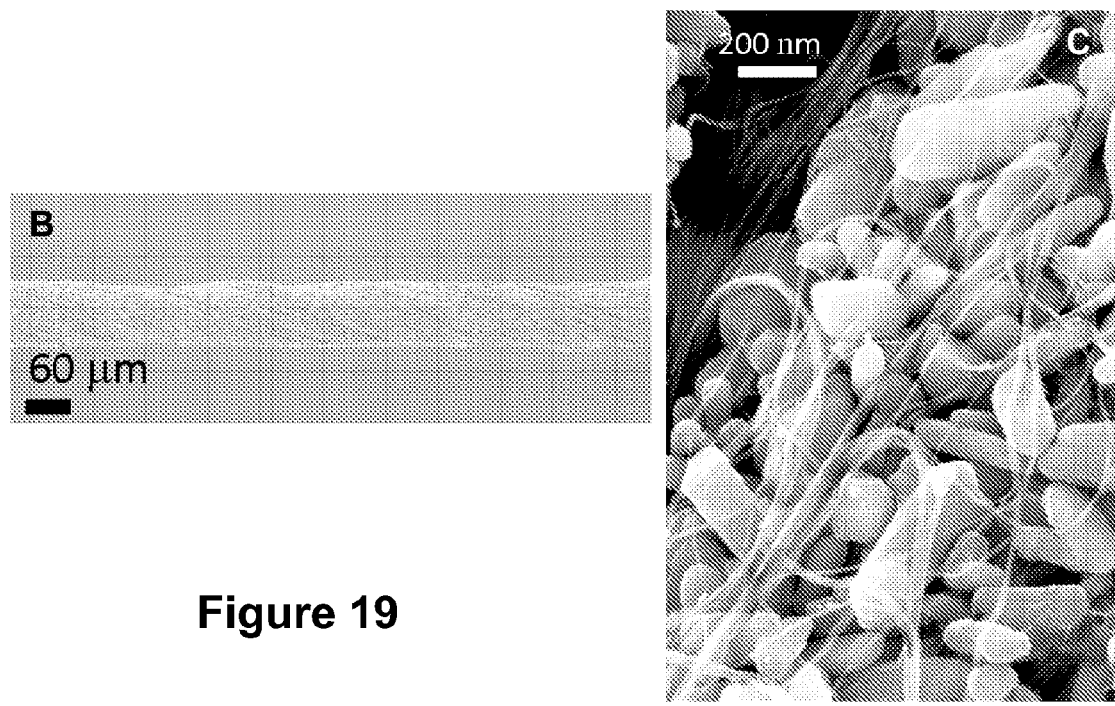

As shown in FIG. 19A, charge and discharge curves at rates of 0.05 C, 0.15 C, 030 C, and 1.0 C (curves 1901-1904, respectively) show that the material can deliver high specific capacities, about 115 mAh/g of total electrode, without the addition of a binder (typically 7.5 wt %. PVDF), with just 1-10% wt. of CNT (instead of the 10-15 wt %. of carbon black typically used) and without the presence of a metallic current collector (usually Al foil with an extra weight of 20 wt % of the total cathode).

FIG. 19B is the SEM image of the biscrolled $LiFePO_4$@MWNT yarn showing a homogeneous diameter along the length. FIG. 19C is a high magnification SEM image showing the connectivity between MWNT host and $LiFePO_4$ guest.

EXAMPLE 15

This Example 15 demonstrates biscrolling nitrogen-doped carbon nanotube guest in a MWNT host. N-doped MWNTs ($CN_x$) were prepared by floating catalyst CVD method described elsewhere [M. Terrones et al., *Chem. Commun.* 23, 2335 (2000)] using benzilamine ($C_6H_5CH_2NH_2$) and ferrocene ($\eta^5$-Fe($C_5H_5$)$_2$) as C/N and iron source respectively. Purification was carried out by reflux in a mixture of HCl and $CH_3COOH$ (7:2 vol) for 16 h to remove all the iron impurities; these "purified" $CN_x$ MWNTs were dispersed in an aqueous solution (0.1% wt of SDS). An aliquot of this dispersion was used as feeding medium for preparing biscrolled yarns with a linear density of 15 μg/cm by the filtration method described in Example 3 (using one host MWNT sheet as support).

Figure 20:
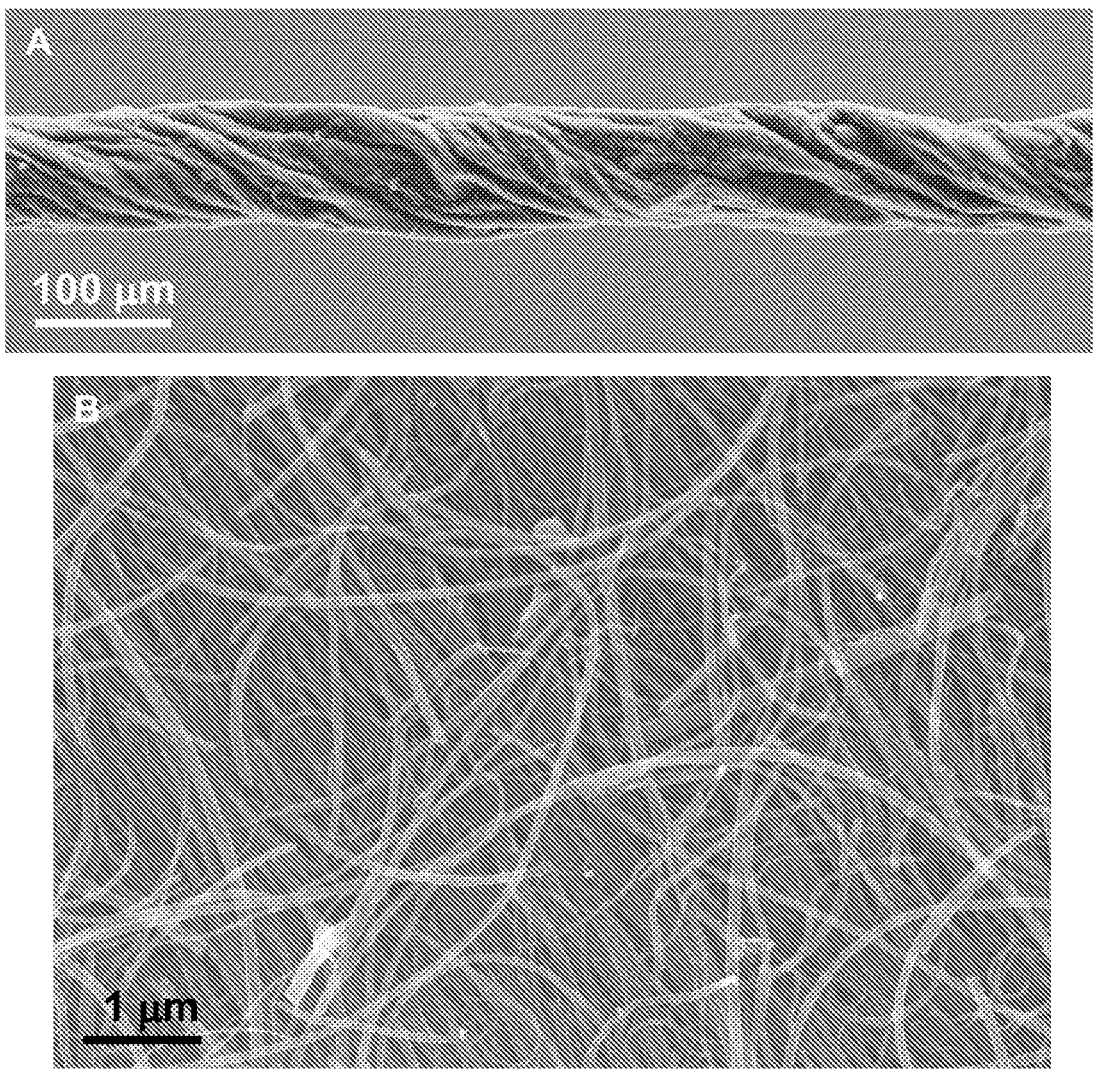
FIGS. 20A-20C show: (20A) a SEM image of a biscrolled N-doped CNT (CN$_x$)@MWNT yarn; (20B) a higher magnification SEM showing the surface of the yarn of (20A); and (20C) a graph plotting the tensile stress-strain curve of the biscrolled CN$_x$@MWNT yarn.
Figure 20:
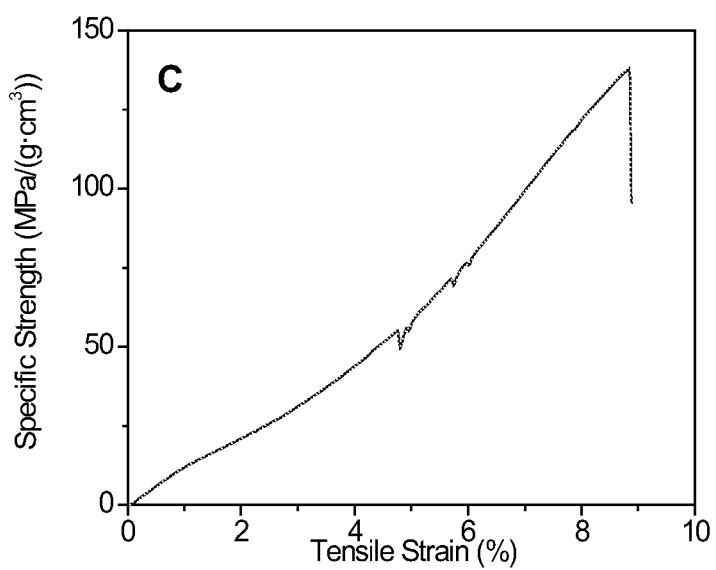

FIG. 20A shows a SEM image of the biscrolled $CN_x$@MWNT yarn. FIG. 20B provides a higher magnification SEM image showing the surface of the yarn of FIG. 20A. FIG. 20C shows tensile stress-strain curve of the biscrolled $CN_x$@MWNT yarn.

Figure 21:
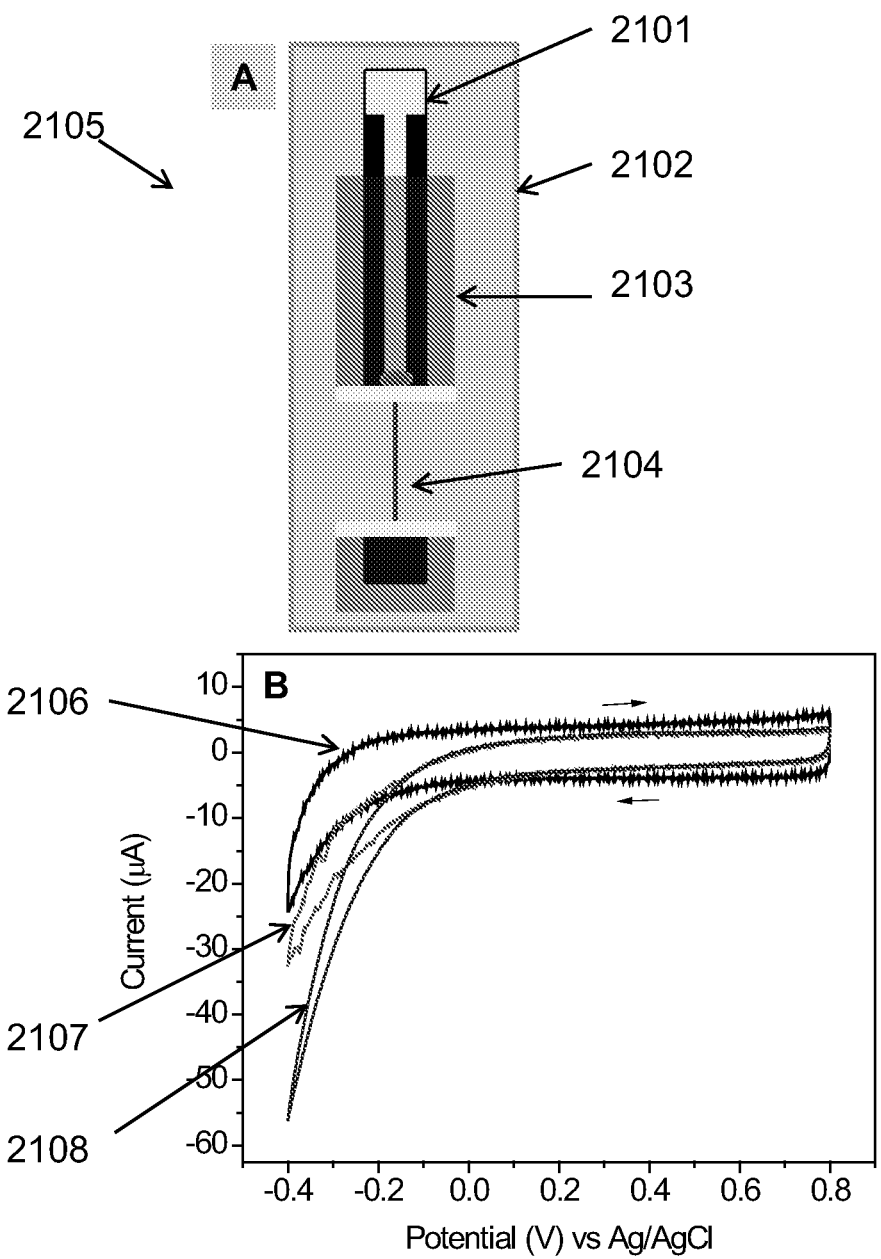
FIGS. 21A-21B show: (21A) an electrode holder 2105 for the electrochemical measurements of yarn 2104 and sheets; and (21B) the cyclic voltammetry response of the CN$_x$@MWNT yarns and other materials in aerated 0.5 M H$_2$SO$_4$ at the scan rate of 25 mV/s. The curves presented are for pure MWNT yarn (curve 2106), biscrolled CN$_x$@MWNT yarn (curve 2107), and CN$_x$ deposited on MWNT sheet (curve 2108). The samples have linear density around 14±1 µg/cm. The oxygen reduction current onset is shifted toward +0.3 V for both samples containing CN$_x$ as guest.

The electrochemical performance of these biscrolled $CN_x$@MWNT yarns in the oxygen reduction reaction (ORR) was tested by cyclic voltammetry (CV) in a 3 electrode cell. For electrochemical measurements, rigid holders (such as electrode holder 2105, as shown in FIG. 21A) were prepared in order to submerge these yarns in an aqueous solution (0.5 M $H_2SO_4$) saturated with $O_2$ by bubbling air in the solution. As show in FIG. 21A, electrode holder 2105 includes aluminum foil 2101, glass slide 2102, and insulation layer 2103.

A Pt mesh was used as a counter electrode, while Ag/AgCl/ 3M NaCl served as reference electrode. Cyclic voltammograms (CVs) were obtained at 5 mV/s for the voltage range +0.8 V to −0.4 V after the voltammogram shape was reproducible for each test. Voltammograms obtained for at a scan rate of 25 mV/s in aerated 0.5 M $H_2SO_4$ are compared in FIG. 21B for pure MWNT yarn (curve 2106), biscrolled $CN_x$@MWNT yarn (curve 2107), and $CN_x$ deposited on a MWNT sheet (curve 2108). Similar to the reported in literature [S. Kundu, et al.; J. Phys. Chem C, 113, 14302-14310 (2009) ("Kundu 2009")] for conventional electrode geometry, a displacement to more positive potentials (~0.3V) was found for the onset of the ORR for the $CN_x$@MWNT yarns when compared to the control pure MWNT yarn.

Because of this performance, these biscrolled $CN_x$@MWNT yarns can be utilized as the oxygen electrode in proton exchange membrane fuel cells (PEMFCs) and for other electrochemical applications.

EXAMPLE 16

This Example 16 demonstrates application of biscrolled yarns containing guest $TiO_2$ as a photo catalyst. $TiO_2$ powder was suspended in 1% SDS aqueous solution and filtration-deposited on a MWNT sheet stack (Example 3). Then an additional layer of MWNT sheet was placed on top of the $TiO_2$ layer to confine the guest. Twist was inserted as described in Example 11.

Figure 22:
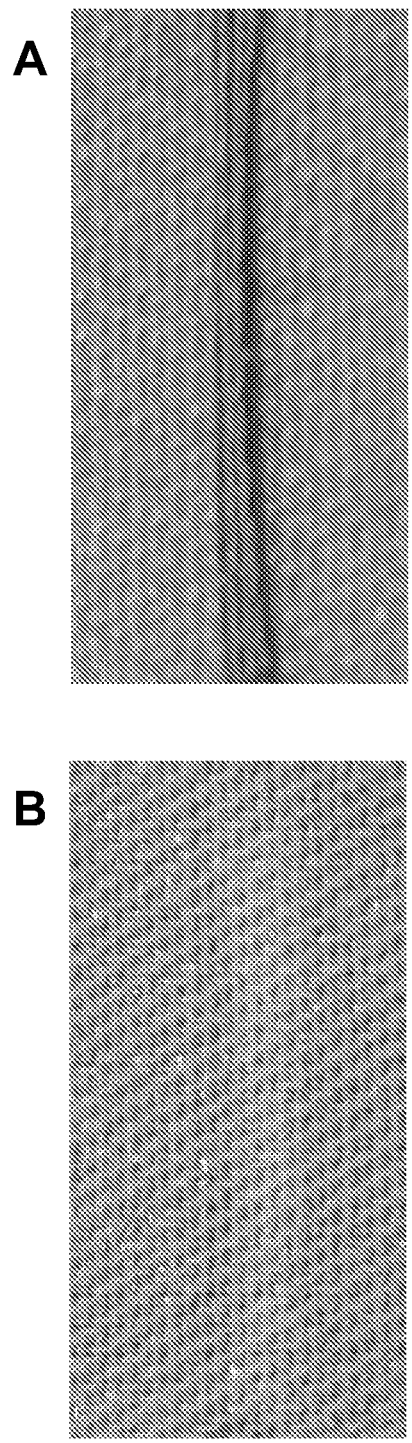
FIGS. 22A-22B show: (22A) a photograph of a dyed fabric (with an overlaid TiO$_2$@MWNT biscrolled yarn taken before the photo-catalytic action of the biscrolled TiO$_2$ yarn for bleaching the dye; and (22B) a photograph of the reverse side of the fabric taken after UV irradiation on the surface containing the TiO$_2$@MWNT biscrolled yarn.

To test catalyzed photolysis caused by the biscrolled $TiO_2$@MWNT yarn, a piece of cotton fabric (3 cm×4 cm) was dyed by soaking in a solution of methylene blue, and then dried overnight in a vacuum oven. A biscrolled $TiO_2$@MWNT yarn was then laid overtop the dyed cotton fabric and placed under a mercury UV lamp that provided 365 nm radiation. The intensity of the lamp was 64 W/m². It was noticed that after 4 hours of irradiation, a bleaching effect was visible even on the reverse side of the dyed fabric, which was neither in direct contact with the biscrolled yarn or exposed to the UV light. FIG. 22A shows a photograph of a dyed fabric (with an overlaid $TiO_2$@MWNT biscrolled yarn) taken before the photo-catalytic action of the biscrolled $TiO_2$ yarn for bleaching the dye. FIG. 22B shows a photograph of the reverse side of the fabric taken after UV irradiation on the surface containing the $TiO_2$@MWNT biscrolled yarn. This shows that the active oxygen produced by the biscrolled yarn is able to penetrate though the dyed textile to cause bleaching of the dye on the fabric surface that was neither in direct contact with the biscrolled yarn or UV irradiated. The photographs of FIG. 22A and FIG. 22B have been modified to increase the clarity of the message.

The robustness of $TiO_2$@MWNT yarns for retaining $TiO_2$ during the cleaning of textiles (for example using a washing machine) was investigated using a model system. The robustness test was done on a biscrolled $TiO_2$@MWNT yarn in which the concentration of $TiO_2$ was nearly 93%. The weight of the yarn before washing was measured. The yarn was then immersed in 1 wt % SDS suspension, which was placed on a hot plate with a magnetic stirrer. The yarn was washed by stirring for 3 hours at 80° C. Then the yarn was taken out of the suspension and dried in vacuum overnight. The weight of the yarn was again measured. The percentage of weight loss of $TiO_2$ was less than 2%.

EXAMPLE 17

This Example 17 compares the guest concentration dependence of yarn mechanical properties of the biscrolled $TiO_2$@MWNT yarn made by $TiO_2$ deposition from an aerosol (as described in Example 8) with that for the biscrolled $TiO_2$@MWNT yarn made by filtration-based deposition of the $TiO_2$. Though the $TiO_2$-free yarn used to provide a baseline for these two different measurement sequences had very different specific strengths, biscrolled yarns made using aerosol-deposition and filtration-deposition provide similar dependencies of specific strength on $TiO_2$ concentration. The weight of the biscrolled yarn was measured using a microbalance. Specific mechanical properties were determined from measurements of force versus strain at 4%/minute strain rate using a mechanical tester (Favimat 37617).

FIG. 4A shows a graph plotting specific yarn breaking strengths versus $TiO_2$ weight concentration for $TiO_2$ deposited by the filtration-based process. The guest-free nanotube yarn has a specific strength of 273 MPa/(g/cm³). As the $TiO_2$ concentration increases, the specific breaking strength of the $TiO_2$@MWNT biscrolled yarn decreases approximately proportionally. This suggests that the guest component ($TiO_2$) did not contribute to the mechanical strength of the biscrolled $TiO_2$@MWNT yarn, which is expected because of the powder nature of the $TiO_2$.

More surprisingly, even high concentrations of $TiO_2$ did not dramatically degrade the nanotube contribution to biscrolled yarn specific strength. This is indicated in FIG. 4B, which is a graph in which the yarn breaking force normalized to MWNT mass/length (rather than total yarn mass/length) was plotted versus $TiO_2$ concentration. Since the MWNT-normalized specific breaking strengths showed small dependency on $TiO_2$ concentration, this confirmed that the contribution of the scrolled MWNT network to yarn strength was little effected by even high $TiO_2$ concentrations.

Figure 23:
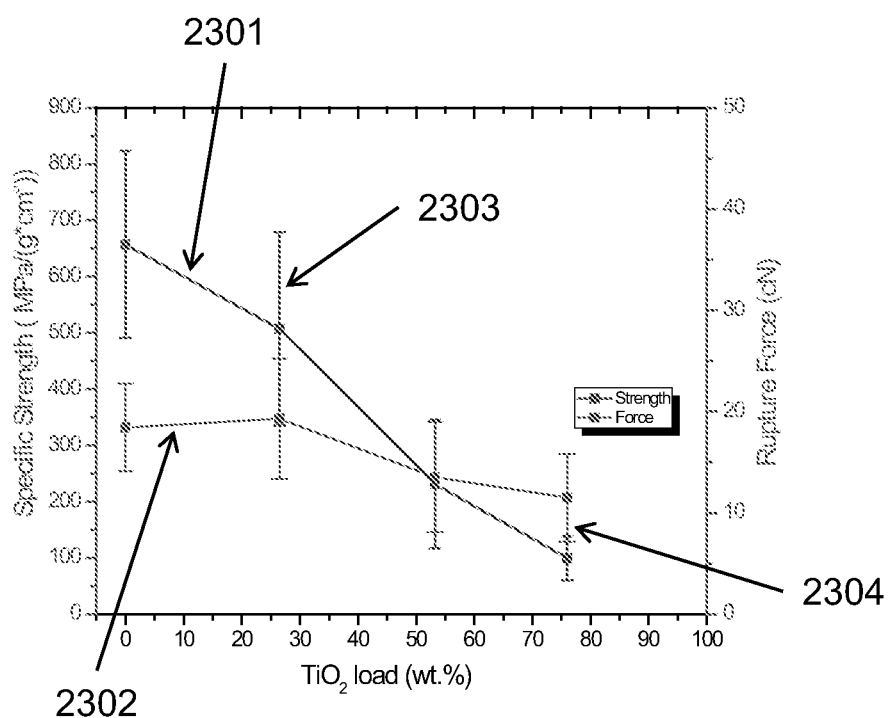
FIG. 23 is a graph that shows the specific mechanical strength (curve 2301) and breaking force (curve 2302) for biscrolled TiO$_2$ yarns prepared using deposition of from an aerosol, as described in Example 8. Error bars 2303 and 2304 show ±2σ. At least 5 samples were tested for each measurement.

FIG. 23 shows the specific mechanical strength and rupture force of $TiO_2$@MWNT biscrolled yarns made by aerosol deposition as a function of $TiO_2$ (curves 2301 and 2302, respectively). The guest-free nanotube yarn in this case had a specific strength of 650 MPa/(g/cm³). As the $TiO_2$ concentration increased, the specific strength of the biscrolled $TiO_2$@MWNT yarn decreased approximately proportionally, as for the $TiO_2$@MWNT biscrolled yarn made using filtration-based deposition.

EXAMPLE 18

This Example 18 describes microscopic study of the biscrolled yarn structure using SEM images. For microscopic analysis of the biscrolled yarn cross-sections, a focused ion-beam was used to cut the yarns. The yarn was placed on a substrate, and an ion-beams of various current values, typically above 1 nA, were used to make a clean cut on the yarn. After the cutting, different stages of polishing were performed on the cutting surfaces by ion-beams of lower energies until a smooth surface structure was obtained on the yarn cross-section.

Figure 24:
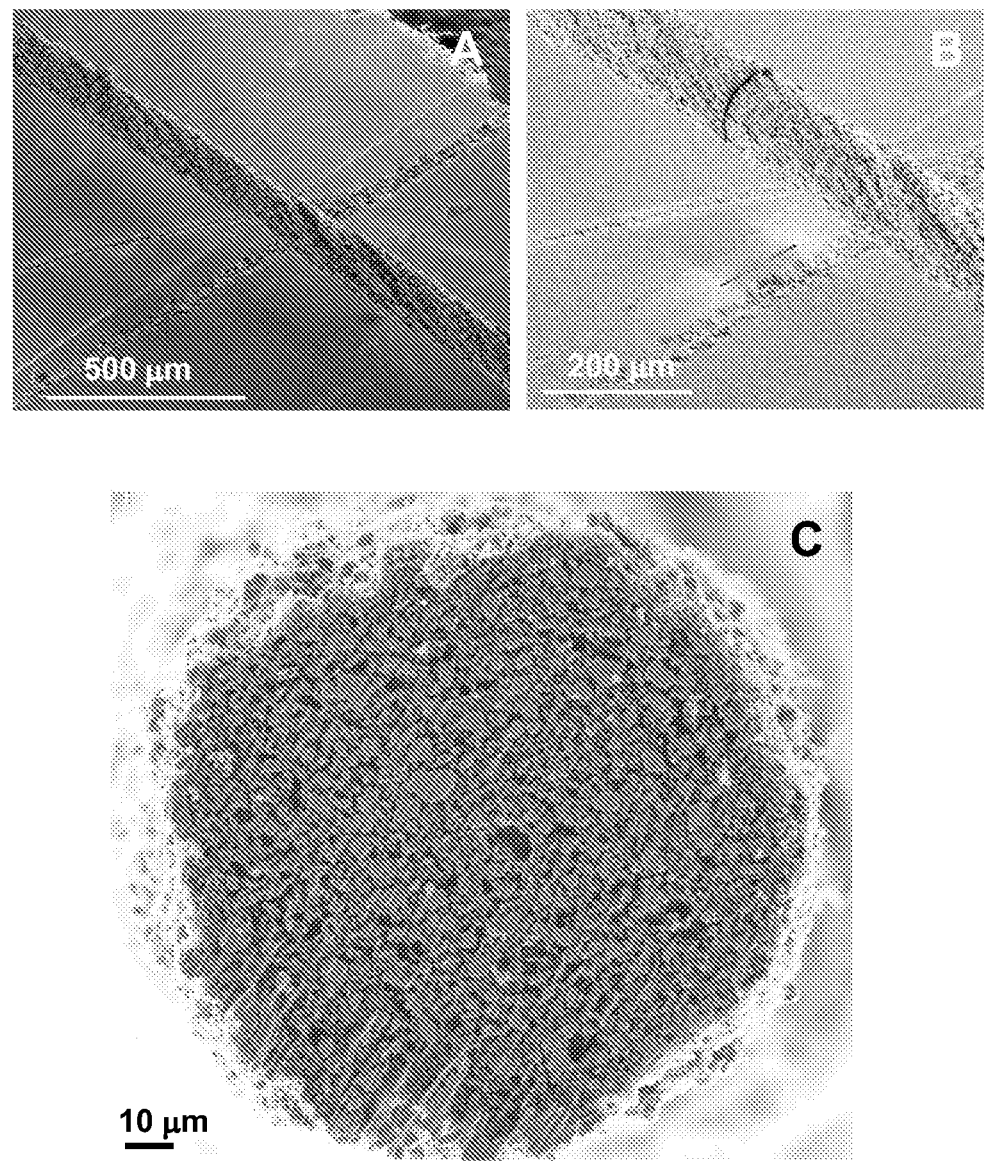
FIGS. 24A-24C show: (24A) a SEM image of a TiO$_2$ biscrolled yarn before FIB cutting; (24B) a SEM image of the biscrolled yarn after FIB cutting; and (24C) a SEM image of the cross-section of the biscrolled yarn after ion-beam-based polishing.

FIG. 24A shows a SEM image of a $TiO_2$ biscrolled yarn before FIB cutting. FIG. 24B shows a SEM image of the biscrolled yarn after FIB cutting. FIG. 24C shows a SEM image of the cross-section of the biscrolled yarn after ion-beam-based polishing.

EXAMPLE 19

This Example 19 demonstrates extension of biscrolling to electrically insulating hosts: arrays of hollow $SiO_2$ and $Si_3N_4$ nanotubes. Individual carbon nanotubes and nanotube bundles in free-standing, forest-drawn MWNT sheets were conformably coated with ~10 nm thickness of $SiO_2$ or $Si_3N_4$ produced by plasma-enhanced CVD (as described in Example 6).

Figure 25:
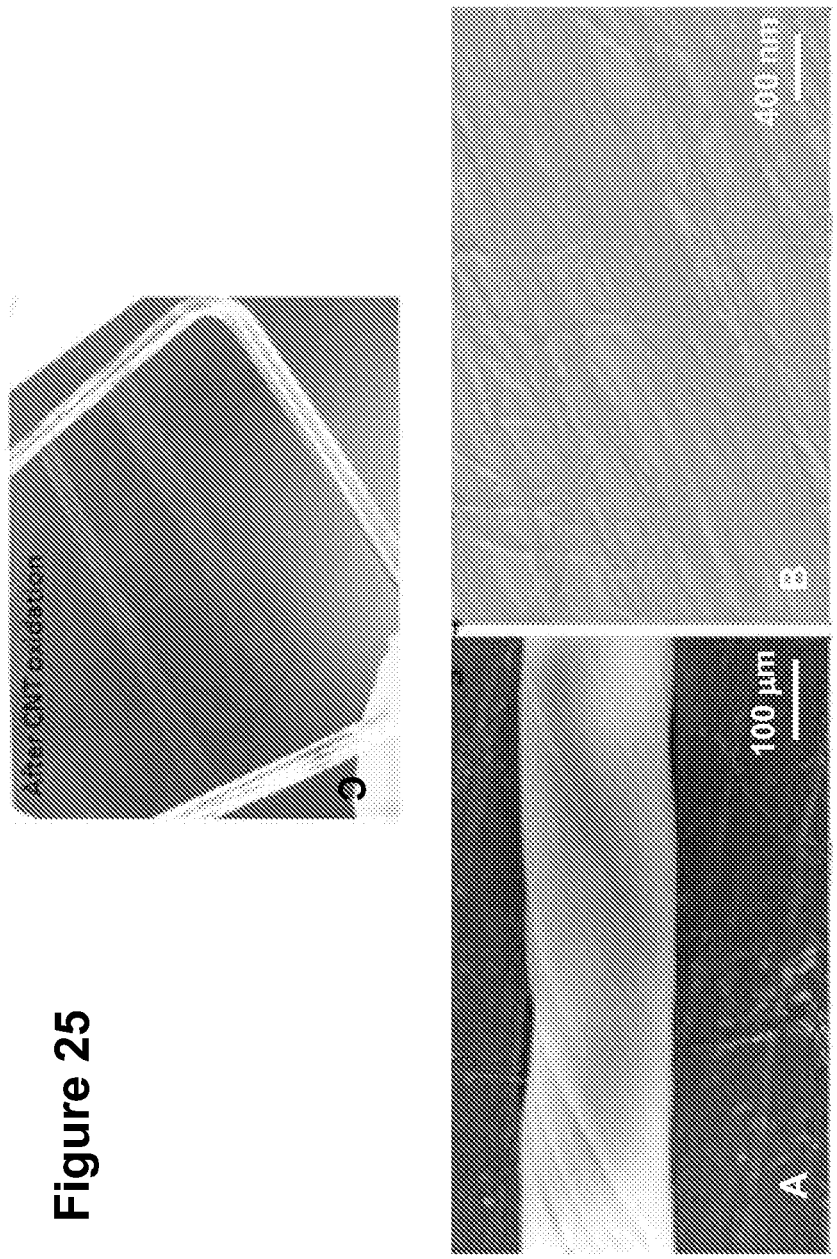
FIGS. 25A-25C show: (25A) a SEM image of a twist-spun Si$_3$N$_4$ yarn from the derived arrays of hollow ceramic nanofibers; (25B) a higher magnification SEM of (25A) showing the surface of the yarn; and (25C) a suspended sheet of arrays of hollow Si$_3$N$_4$ ceramic nanotubes obtained by removing the carbon nanotube cores.

Free standing nanotube sheets were subsequently obtained by removing the carbon nanotube cores (by combustion in air at high temperature or in ozone at room temperature). FIG. 25C shows a suspended sheet of arrays of hollow $Si_3N_4$ ceramic nanotubes obtained by removing the carbon nanotube cores. Both the ceramic coated carbon nanotube sheets and the thereby derived ceramic nanotube sheets could be twist spun to make a yarn (as shown in FIGS. 25A-25B), and both could be overlaid with other functional materials to enable the spinning of biscrolled yarns. As an example, $Si_3N_4$ coated carbon nanotube sheet was biscrolled with 3.7 wt. % Pt nanoparticles (deposited by e-beam evaporation) to make a mechanically robust yarn.

Relevant for application of the ceramic-coated carbon nanotubes as host for biscrolled yarn, conformally coating the carbon nanotubes with ~10 nm thickness of $SiO_2$ did not significantly affect in-plane sheet conductance or the conductance of twisted yarns.

EXAMPLE 20

This Example 20 describes the catalytic activity of biscrolled yarn containing platinum black powder as guest, when the biscrolled yarn was immersed in hydrogen peroxide solution. Platinum black powder is a well known catalytic material that decomposes hydrogen peroxide into water and oxygen. This decomposition is an exothermic process and the resulting increase of temperature per unit time can be used as an index of decomposition rate. In this experiment the decomposition of hydrogen peroxide in the presence of biscrolled yarn (with platinum black) was studied and compared with the performance of the performance of the same quantity (20 µg) of free platinum black powder.

Figure 26:
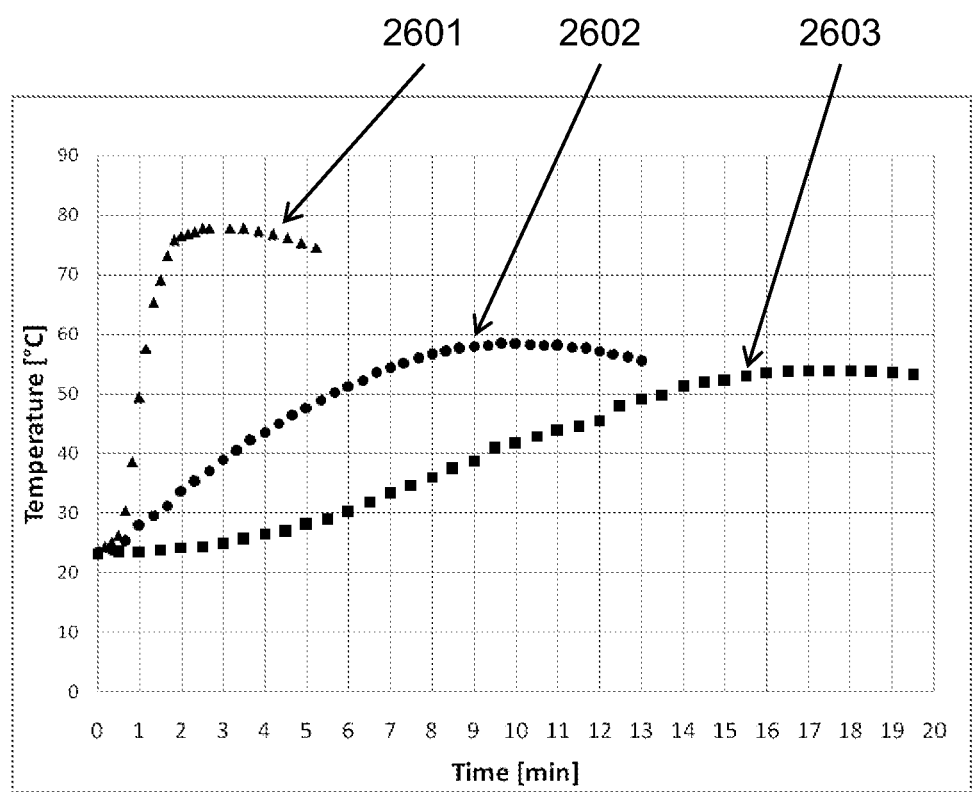
FIG. 26 compares the temperature increase due to catalytic decomposition of hydrogen peroxide by 20 µg of free platinum black powder (triangular line 2601) with that due to the same amount of Pt black powder that is confined inside a biscrolled yarn at 83 wt % loading level (round line 2602) or 64.4 wt % loading level (square line 2603).

FIG. 26, curve 2601 (triangle data points), shows the increase of temperature due to exothermic decomposition of hydrogen peroxide (32% concentration) in the presence free platinum black powder. Curves 2602 (circle data points) and 2603 (square data points) show similar measurement when the equivalent amount of powder was confined inside biscrolled yarn at 83.0 wt % and 64.4 wt % concentrations, respectively.

Though the reaction rate was decreased because of Pt black confinement in a biscrolled yarn, as is expected, it is noteworthy that the biscrolled Pt black retained catalytic activity.

EXAMPLE 21

Figure 27:
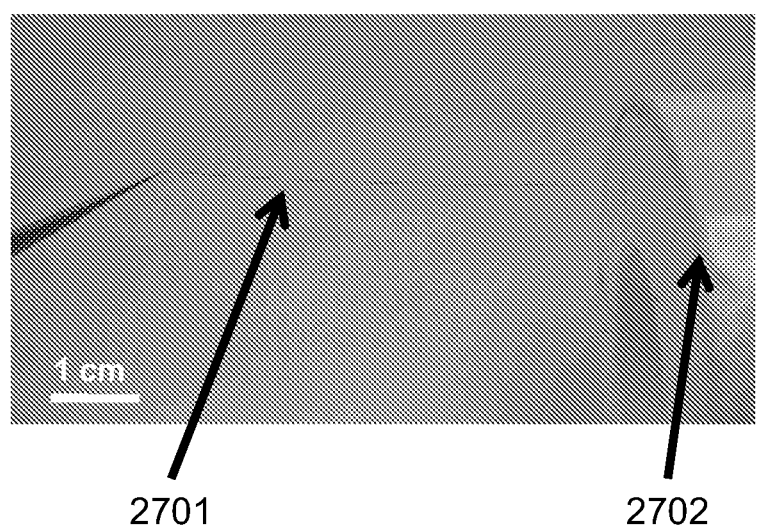
FIG. 27 shows a biscrolled magnetic wire containing nickel particles 2701 responding in the presence of a permanent magnet 2702.

This Example 21 demonstrates making biscrolled yarn containing nickel powder guest for magnetic wire application. Nickel powder (3 µm average diameter) was deposited on MWNT sheet by using the electrostatic spray method, and then the resulting bilayer stack was biscrolled. FIG. 27 shows that the Ni@MWNT yarn (2701) was highly magnetic, as indicated by its attraction to the pictured magnet (2702).

EXAMPLE 22

This Example 22 demonstrates the use of a scrolled MWNT sheet strip for confining Pt black on a nickel-titanium (NiTi) alloy shape memory alloy (SMA) actuator wire for application as a fuel-driven actuator. [V. E. Ebron et al., Science 311, 1580-1583 (2006)].

Figure 28:
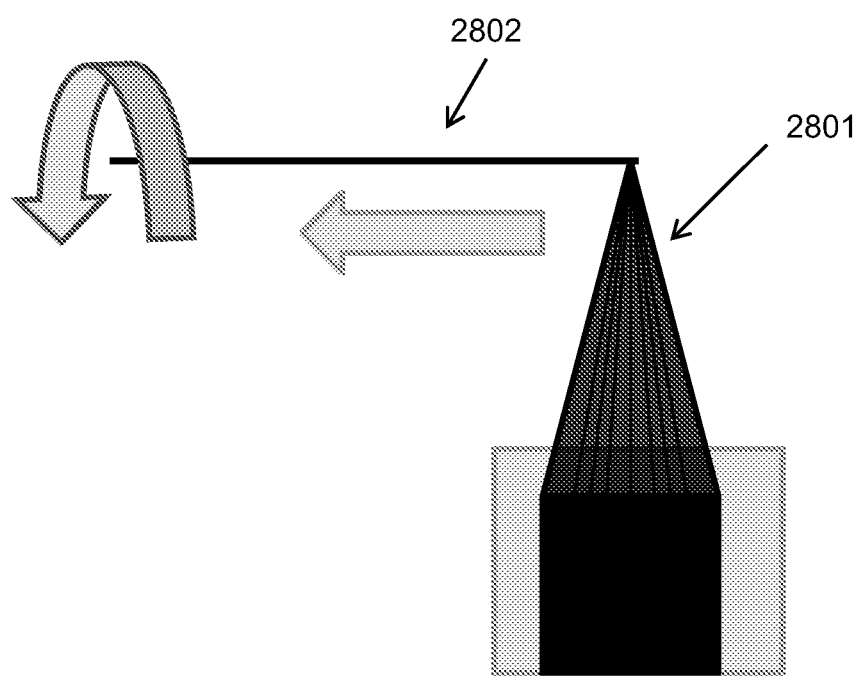
FIG. 28 schematically illustrates continuous wrapping of Pt-black@MWNT sheet 2801 onto a spinning core (shape memory wire 2802) by translation of the sheet along the length of the wire 2802, resulting in a helically biscrolled structure around the NiTi wire having highly catalytic properties and high cycle life needed for fuel powered artificial muscles.

FIG. 28 schematically illustrates continuous wrapping of Pt-black@MWNT sheet 2801 onto a spinning core (shape memory wire 2802) by translation of the sheet along the length of the wire 2802, resulting in a helically biscrolled structure around the NiTi wire having highly catalytic properties and high cycle life needed for fuel powered artificial muscles. Various diameters of commercially-purchased SMA wires were rotated about their axis in order to continuously draw from a MWNT forest. Simultaneous solid-state deposition of Pt-black catalyst was performed on the MWNT sheet in order to produce a Pt-black@MWNT composite ribbon. Translation of the sheet along the length of the wire during this process results in a helically biscrolled structure around the NiTi wire with highly catalytic properties.

Upon application of hydrogen gas or methanol vapors to these catalytic NiTi SMA wires, room-temperature combustion of the fuel heats the SMA wire, resulting in actuation comparable to that of electrically-driven SMA. The Pt-black@MWNT wrap provides an ideal structure for this interaction as it is simultaneously: highly porous for fuel-catalyst interaction, thermally conductive for heat transfer between catalyst particles and the wire, thermally stable across a wide temperature range and flexible to withstand the ~4% dimensional change associated with actuation. By regulation of cyclical delivery of a hydrogen-oxygen fuel, such biscrolled wires have been tested to perform in excess of 50,000 cycles without showing any noticeable degradation.

EXAMPLE 23

This Example 23 describes methods for the fabrication of biscrolled MWNT yarn that contains guest growth factors that may be useful for the selective directional growth of tissue, such as liver tissue. Tissues express or contain factors that guide regeneration and proliferation of new tissue growth. Growth factors can determine tissue growth by providing a gradient of diffusible factors.

Deposition of lyophylized growth factors onto a MWNT sheet strip or wedge and then biscrolling to form biscrolled yarns may provide regenerative scaffolds for in vitro 3-dimensional tissue bioengineering of tissue types from single or co-cultures. Dry deposition of powder forms of growth factor via manual or airbrush technique can be utilized.

EXAMPLE 24

This Example 24 demonstrates the use of biscrolling to confine high concentrations of biologically active agents as guests in yarns that are sufficiently strong to be sewn into muscle. Biscrolled MWNT yarn (FIG. 29A) was prepared by first depositing biological agents, particularly a powder mixture of anti-inflammatory and antiseptic agents, onto a 3 layer MWNT sheet. The antiseptic agent (benzalkonium chloride) was mist sprayed 4 times with a simple commercial spray gun, followed by hand spread of approximately 0.5 mg of steroid powder (synthetic corticosteroid tablet, crushed to 2-10 micron diameter particles). The bilayered structure was then twisted manually into yarn and threaded for use as a suture thread into a ⅜ circle cutting edge suture needle (FIG. 29B, where 2901 is a conventional suture thread and 2902 is a suture thread that is a biscrolled yarn).

Subcutaneous and cutaneous layers of a full thickness laceration in the forefoot of a butchered pig (purchased at a grocery store) were sutured with this biscrolled yarn (FIG. 29C). The sutures proved resilient and resistant to breakage and strain failure after passing through the tough, rigid epidermal and dermal layers of the pig forefoot. Simple interrupted and horizontal mattress technique was demonstrated using the biscrolled yarn suture. Horizontal mattress technique is a particularly useful method of suturing for areas where sutures are under high tension and movement. Subsequently, these biscrolled yarn sutures were easily quadruply knotted using square knots for closure.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

What is claimed is:

1. A method comprising the steps of:
   a. forming a nanofiber sheet or nanofiber sheet stack as a sheet platform for particle material deposition;
   b. depositing particle material onto the sheet platform to form a bilayered sheet structure; and
   c. scrolling the bilayered sheet structure into a biscrolled yarn.

2. The method of claim 1, further comprising densifying the biscrolled yarn using liquid absorption and subsequent evaporation.

3. The method of claim 1, further comprising introducing a twist during formation of the biscrolled yarn.

4. The method of claim 3, wherein the sheet platform comprises carbon nanotubes.

5. The method of claim 1, wherein the biscrolled yarn has a specific strength at least about 50 MPa/(g/cm$^3$).

6. The method of claim 4, wherein the carbon nanotubes in the sheet platform are predominately oriented in the same in-plane direction.

7. The method of claim 4, wherein the carbon nanotube sheet platform is selected from the group consisting of (a) a carbon nanotube sheet wedge that results from direct twist-based spinning from a carbon nanotube forest and (b) a self-suspended nanotube sheet or sheet stack obtained by sheet draw from a carbon nanotube forest.

8. The method of claim 1, wherein the particle material comprises at least about 50 weight percent of the biscrolled yarn.

9. The method of claim 1, wherein the particle material comprise nanoparticles.

10. The method claim 9, wherein the nanoparticles comprise nanofibers.

11. The method of claim 10, wherein the nanofibers comprise nitrogen doped nanotubes or graphene ribbons.

12. The method of claim 1, wherein the particle material comprises a superconductor or components that can be converted to a superconductor by processing the biscrolled yarn.

13. The method of claim 1, wherein the particle material comprises a catalyst.

14. The method of claim 1, wherein the particle material comprise a biologically active material.

15. The method of claim 1, wherein the particle material comprises $TiO_2$.

16. The method of claim 1, further comprising
   a. using particle material that can be liquid dispersed, and
   b. depositing the particle material from a liquid dispersed state.

17. The method of claim 1, wherein the step of depositing the particle material comprises a liquid-free deposition method.

18. The method of claim 17, wherein the liquid-free deposition method is selected from the group consisting of: electrostatic deposition, electron beam evaporation, sputtering, chemical vapor deposition (CVD), dry powder airbrush deposition, deposition of gas-dispersed guest nanoparticles immediately after their formation by reaction of gases, and combinations thereof.

19. The method of claim 1, wherein the step of depositing particle material comprises profiling distribution of the particle material.

20. The method of claim 19, wherein
   (a) the step of profiling the distribution of the particle material comprises preferentially positioning the particle material on one side of the sheet platform; and
   (b) the step of preferentially positioning the particle material results in preferential distribution of the particle material in either the core or shell of the biscrolled yarn.

* * * * *